United States Patent
Cantor et al.

(10) Patent No.: US 11,591,403 B2
(45) Date of Patent: Feb. 28, 2023

(54) IL-23R ANTAGONISTS TO REPROGRAM INTRATUMORAL T REGULATORY CELLS INTO EFFECTOR CELLS

(71) Applicant: Dana-Farber Cancer Institute, Inc., Boston, MA (US)

(72) Inventors: Harvey Cantor, Boston, MA (US); Hye-Jung Kim, Brookline, MA (US); Jessica M. Sido, Ayer, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/609,918

(22) PCT Filed: May 2, 2018

(86) PCT No.: PCT/US2018/030636
§ 371 (c)(1),
(2) Date: Oct. 31, 2019

(87) PCT Pub. No.: WO2018/204489
PCT Pub. Date: Nov. 8, 2018

(65) Prior Publication Data
US 2020/0055945 A1 Feb. 20, 2020
US 2021/0040220 A9 Feb. 11, 2021

Related U.S. Application Data

(60) Provisional application No. 62/500,443, filed on May 2, 2017.

(51) Int. Cl.
| | | |
|---|---|---|
| *A61K 39/395* | (2006.01) | |
| *C07K 16/28* | (2006.01) | |
| *A61K 45/06* | (2006.01) | |
| *A61P 35/00* | (2006.01) | |
| *C12N 5/0783* | (2010.01) | |
| *G01N 33/50* | (2006.01) | |
| *A61K 39/00* | (2006.01) | |

(52) U.S. Cl.
CPC ...... *C07K 16/2866* (2013.01); *A61K 39/3955* (2013.01); *A61K 45/06* (2013.01); *A61P 35/00* (2018.01); *C12N 5/0637* (2013.01); *G01N 33/505* (2013.01); *A61K 2039/505* (2013.01); *C07K 2317/21* (2013.01); *C07K 2317/24* (2013.01); *C07K 2317/33* (2013.01); *C07K 2317/92* (2013.01); *C12N 2501/2302* (2013.01); *C12N 2501/2304* (2013.01); *C12N 2501/998* (2013.01); *C12N 2506/11* (2013.01)

(58) Field of Classification Search
CPC ........................ A61K 39/3955; C07K 16/2866
See application file for complete search history.

(56) References Cited

U.S. PATENT DOCUMENTS

| | | | |
|---|---|---|---|
| 5,500,362 A | 3/1996 | Robinson et al. | |
| 2006/0235208 A1* | 10/2006 | Lazar ................. | C07K 16/2893 530/388.22 |
| 2009/0088329 A1 | 4/2009 | Brennan et al. | |
| 2010/0166767 A1* | 7/2010 | Presta ....................... | A61P 1/14 424/158.1 |
| 2013/0035365 A1 | 2/2013 | Gallagher et al. | |
| 2013/0309250 A1* | 11/2013 | Cogswell ......... | G01N 33/57492 424/172.1 |

FOREIGN PATENT DOCUMENTS

| | | |
|---|---|---|
| EP | 2821416 A1 | 1/2015 |
| WO | WO 2014/180577 A1 | 11/2014 |
| WO | WO 2016/196912 A1 | 12/2016 |

OTHER PUBLICATIONS

Nair et al., J. Immunol., 2002, vol. 168(5):2371-2382.*
Lu et al., J. Immunol., 2004, vol. 173(6):3972-3978.*
Kalliolias et al., Nat. Rev. Rheumatol., Jan. 2016., vol. 12(1):49-62.*
Egberts et al., Cancer Res., 2008, vol. 68(5):1443-1450.*
Kortylewski et al., Cancer Cell, 2009, vol. 15:114-123.*
Suzuki et al., Oncol. Lett., 2012, vol. 4(2):199-204.*
Extended European Search Report for Application No. 18793923.6, datd Apr. 23, 2021.
Partial European Search Report for Application No. 18793923.6, dated Jan. 22, 2021.
Kortylewski et al. Regulation of the IL-23 and IL-12 balance by Stat3 signaling in the tumor microenvironment. Cancer Cell. Feb. 3, 2009; 15(2):114-23.
Langowski et al., IL-23 promotes tumour incidence and growth. Nature. Jul. 27, 2006;442(7101):461-5. doi: 10.1038/nature04808. Epub May 10, 2006. PMID: 16688182.
International Preliminary Report on Patentability for Application No. PCT/US2018/030636, dated Nov. 14, 2019.
International Search Report and Written Opinion for Application No. PCT/US2018/030636, dated Jul. 19, 2018.
Armour et al., Recombinant human IgG molecules lacking Fcγ receptor I binding and monocyte triggering activities. Eur. J. Immunol. Aug. 1999; 29(8):2613-24.
Barbi et al., Treg functional stability and its responsiveness to the microenvironment. Immunol Rev. May 2014; 259(1):115-39.
Bautista et al., Intraclonal competition limits the fate determination of regulatory T cells in the thymus. Nature immunology. Jun. 2009; 10(6): 610-7.
Beyer et al., Regulatory T cells in cancer. Blood. Aug. 1, 2006; 108(3): 804-11.
Bovenschen et al., Foxp3+ Regulatory T Cells of Psoriasis Patients Easily Differentiate into IL-17A-Producing Cells and Are Found in Lesional Skin. Journal of Investigative Dermatology. Sep. 1, 2011; 131(9): 1853-60.

(Continued)

*Primary Examiner* — Xiaozhen Xie
(74) *Attorney, Agent, or Firm* — Baker Donelson

(57) ABSTRACT

Provided by the disclosure are compositions and methods for modulating differentiation of regulatory T cells. In some embodiments, methods include selectively decreasing IL-23R activity and/or IL-23R expression without significantly decreasing IL-12Rβ activity and/or IL-12Rβ expression.

15 Claims, 53 Drawing Sheets

Specification includes a Sequence Listing.

(56) References Cited

OTHER PUBLICATIONS

Bloch et al., Structural Activation of Pro-inflammatory Human Cytokine IL-23 by Cognate IL-23 Receptor Enables Recruitment of the Shared Receptor IL-12Rβ1. Immunity. Jan. 16, 2018;48(1):45-58.e6. doi: 10.1016/j.immuni.2017.12.008. Epub Dec. 26, 2017.
Carell et al., A Novel Procedure for the Synthesis of Libraries Containing Small Organic Molecules. Angew Chem. Int. Ed. Engl. Nov. 2, 1994; 33(20): 2059-61.
Carell et al., A Solution-Phase Screening Procedure for the Isolation of Active Compounds from a Library of Molecules. Angew Chem. Int. Ed. Engl. Nov. 2, 1994; 33(20):2061-4.
Cho et al., An unnatural biopolymer. Science. Sep. 3, 1993;261(5126):1303-5.
Collison et al., In vitro Treg suppression assays. Methods in molecular biology. 2011; 707: 21-37.
Cua et al. Interleukin-23 rather than interleukin-12 is the critical cytokine for autoimmune inflammation of the brain. Nature. 2003;421(6924):744-748. doi:10.1038/nature01355.
Cull et al., Screening for receptor ligands using large libraries of peptides linked to the C terminus of the lac repressor. Proceedings of the National Academy of Sciences. Mar. 1, 1992;89(5):1865-9.
Cwirla et al., Peptides on phage: a vast library of peptides for identifying ligands. Proceedings of the National Academy of Sciences. Aug. 1, 1990;87(16):6378-82.
Dallas et al., Interleukins-12 and -23 do not alter expression or activity of multiple cytochrome P450 enzymes in cryopreserved human hepatocytes. Drug Metabolism and Disposition. Apr. 1, 2013;41(4):689-93.
Dewitt et al., Diversomers: An approach to nonpeptide, nonoligomeric chemical diversity. Proceedings of the National Academy of Sciences. Aug. 1, 1993;90(15):6909-13.
Dipaolo et al., CD4+ T-cell development in a mouse expressing a transgenic TCR derived from a Treg. European journal of immunology. Jan. 2009; 39(1): 234-40.
Dougan et al., Transnuclear TRP1-specific CD8 T cells with high or low affinity TCRs show equivalent antitumor activity. Cancer immunology research. Aug. 1, 2013; 1(2): 99-111.
Erb et al., Recursive deconvolution of combinatorial chemical libraries. Proceedings of the National Academy of Sciences. Nov. 22, 1994;91(24):11422-6.
Facciabene et al., T-regulatory cells: key players in tumor immune escape and angiogenesis. Cancer research. May 1, 2012; 72(9): 2162-71.
Felici et al., Selection of antibody ligands from a large library of oligopeptides expressed on a multivalent exposition vector. Journal of molecular biology. Nov. 20, 1991;222(2):301-10.
Feng et al., Control of the inheritance of regulatory T cell identity by a cis element in the Foxp3 locus. Cell. Aug. 14, 2014; 158(4): 749-63.
Fodor et al., Multiplexed biochemical assays with biological chips. Nature. Aug. 5, 1993;364(6437):555-6.
Gallop et al., Applications of combinatorial technologies to drug discovery. 1. Background and peptide combinatorial libraries. Journal of medicinal chemistry. Apr. 1994;37(9):1233-51.
Ha, The role of regulatory T cells in cancer. Immune network. Dec. 2009; 9(6): 209-35.
Hirschhorn-Cymerman et al., Induction of tumoricidal function in CD4+ T cells is associated with concomitant memory and terminally differentiated phenotype. J experimental medicine. Oct. 22, 2012; 209(11): 2113-26.
Houghten et al., The use of synthetic peptide combinatorial libraries for the identification of bioactive peptides. Biotechniques. Sep. 1992;13(3):412-21.
Ito et al., Two functional subsets of FOXP3+ regulatory T cells in human thymus and periphery. Immunity. Jun. 13, 2008; 28(6): 870-80.

Jones et al., Replacing the complementarity-determining regions in a human antibody with those from a mouse. Nature. May 1986;321(6069):522-5.
Josefowicz et al. (2012). Regulatory T cells: mechanisms of differentiation and function. Annu Rev Immunol. Apr. 23, 2012; 30: 531-64.
Kannan et al., IL-23 induces regulatory T cell plasticity with implications for inflammatory skin diseases. J Immunology. 2019;9:17675.
Kim et al., Stable inhibitory activity of regulatory T cells requires the transcription factor Helios. Science. Oct. 16, 2015;350(6258):334-9.
Komminoth et al., Evaluation of methods for hepatitis C virus detection in archival liver biopsies: comparison of histology, immunohistochemistry, in-situ hybridization, reverse transcriptase polymerase chain reaction (RT-PCR) and in-situ RT-PCR. Pathology-Research and Practice. Nov. 1, 1994;190(11):1017-25.
Kuczma et al., Intratumoral convergence of the TCR repertoires of effector and Foxp3+ CD4+ T cells. PloS one. Oct. 26, 2010; 5(10): e13623.
Lam et al., A new type of synthetic peptide library for identifying ligand-binding activity. Nature. Nov. 1991;354(6348):82-4.
Lam, Mini-review. Application of combinatorial library methods in cancer research and drug discovery. Anti-cancer drug design. Apr. 1, 1997;12(3):145-67.
Li et al., Function of a Foxp3 cis-element in protecting regulatory T cell identity. Cell. Aug. 14, 2014; 158(4): 734-48.
Mahoney et al., Combination cancer immunotherapy and new immunomodulatory targets. Nature reviews Drug discovery. Aug. 2015;14(8):561-84.
Malandro et al., Clonal Abundance of Tumor-Specific CD4(+) T Cells Potentiates Efficacy and Alters Susceptibility to Exhaustion. Immunity. Jan. 19, 2016; 44(1): 179-93.
Malchow et al., Aire-dependent thymic development of tumor-associated regulatory T cells. Science. Mar. 8, 2013; 339(6124): 1219-24.
Mougiakakos et al., Regulatory T cells in cancer. Advances in cancer research. Jan. 2010; 107: 57-117.
Nakagawa et al., Instability of Helios-deficient Tregs is associated with conversion to a T-effector phenotype and enhanced antitumor immunity. Proceedings National Academy Sciences. May 31, 2016;113(22):6248-53.
Nishikawa et al., Regulatory T cells in cancer immunotherapy. Current opinion in immunology. Apr. 2014; 27: 1-7.
Nuovo et al., Intracellular localization of polymerase chain reaction (PCR)-amplified hepatitis C cDNA. The American journal of surgical pathology. Jul. 1993;17(7):683-90.
Oleinika et al., Suppression, subversion and escape: the role of regulatory T cells in cancer progression. Clinical and experimental immunology. Jan. 2013; 171(1): 36-45.
Piconese et al., OX40 triggering blocks suppression by regulatory T cells and facilitates tumor rejection. The Journal of experimental medicine. Apr. 14, 2008; 205(4): 825-39.
Presta, Antibody engineering. Curr. Op. Struct. Biol. Aug. 1992; 2(4):593-6.
Quezada et al., Tumor-reactive CD4(+) T cells develop cytotoxic activity and eradicate large established melanoma after transfer into lymphopenic hosts. The Journal of experimental medicine. Mar. 15, 2010; 207(3): 637-50.
Reddy et al., Modulation of CLA, IL-12R, CD40L, and IL-2Rα expression and inhibition of IL-12- and IL-23-induced cytokine secretion by CNTO 1275. Cell Immunol. May 2007; 247(1):1-11.
Riechmann et al., Reshaping human antibodies for therapy. Nature. Mar. 1988;332(6162):323-9.
Sakaguchi, Naturally arising Foxp3-expressing CD25+CD4+ regulatory T cells in immunological tolerance to self and non-self. Nature immunology. Apr. 2005; 6(4): 345-52.
Scott et al., Searching for peptide ligands with an epitope library. Science. Jul. 27, 1990;249(4967):386-90.
Shimizu et al., Induction of tumor immunity by removing CD25+ CD4+ T cells: a common basis between tumor immunity and autoimmunity. Journal of immunology. Nov. 15, 1999; 163(10): 5211-8.

(56) References Cited

OTHER PUBLICATIONS

Takahashi et al., SOCS1 is essential for regulatory T cell functions by preventing loss of Foxp3 expression as well as IFN-{gamma} and IL-17A production. J Ex Med. Sep. 26, 2011; 208(10): 2055-67.
Von Scheidt et al., Combined anti-CD40 and anti-IL-23 monoclonal antibody therapy effectively suppresses tumor growth and metastases. Cancer Res. May 1, 2014; 74(9): 2412-21.
Xu et al., Molecular mechanisms regulating TGF-beta-induced Foxp3 expression. Mucosal immunology. May 2010; 3(3): 230-8.
Zhou et al., Plasticity of CD4+ FoxP3+ T cells. Curr Opin Immunol. Jun. 2009; 21(3):281-5.
Zuckermann et al., Discovery of nanomolar ligands for 7-transmembrane G-protein-coupled receptors from a diverse N-(substituted) glycine peptoid library. Journal of medicinal chemistry. Aug. 1, 1994;37(17):2678-85.

\* cited by examiner

SEQ ID NO: 6

SEQUENCE LISTING

```
<160> NUMBER OF SEQ ID NOS: 33

<210> SEQ ID NO 1
<211> LENGTH: 600
<212> TYPE: PRT
<213> ORGANISM: Homo sapiens

<400> SEQUENCE: 1

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
            35                  40                  45

Ser Ile Tyr Cys Gln Ala Ala Ile Lys Asn Cys Gln Pro Arg Lys Leu
        50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
            115                 120                 125

Asp Glu Val Thr Cys Val Ile Tyr Glu Tyr Ser Gly Asn Met Thr Cys
        130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
            245                 250                 255

Tyr Lys Ala Thr Thr Asn Gln Thr Trp Asn Val Lys Glu Phe Asp Thr
        260                 265                 270

Asn Phe Thr Tyr Val Gln Gln Ser Glu Phe Tyr Leu Glu Pro Asn Ile
            275                 280                 285

Lys Tyr Val Phe Gln Val Arg Cys Gln Glu Thr Gly Lys Arg Tyr Trp
        290                 295                 300
```

```
Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
            325                 330                 335

Thr Val Ala Ser Ile Ser Thr Gly His Leu Thr Ser Asp Asn Arg Gly
        340                 345                 350

Asp Ile Gly Leu Leu Leu Gly Met Ile Val Phe Ala Val Met Leu Ser
            355                 360                 365

Ile Leu Ser Leu Ile Gly Ile Phe Asn Arg Ser Phe Arg Thr Gly Ile
370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
                485                 490                 495

His Leu Ser Asn Asn Asn Glu Ile Thr Ser Leu Thr Leu Lys Pro Pro
            500                 505                 510

Val Asp Ser Leu Asp Ser Gly Asn Asn Pro Arg Leu Gln Lys His Pro
        515                 520                 525

Asn Phe Ala Phe Ser Val Ser Ser Val Asn Ser Leu Ser Asn Thr Ile
    530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Thr Thr Met Leu Leu Glu
                565                 570                 575

Asn Asp Ser Pro Ser Glu Thr Ile Pro Glu Gln Thr Leu Leu Pro Asp
            580                 585                 590

Glu Phe Val Ser Cys Leu Gly Ile
            595                 600

<210> SEQ ID NO 2
<211> LENGTH: 659
<212> TYPE: PRT
<213> ORGANISM: Mus musculus

<400> SEQUENCE: 2

Met Lys Arg Glu Arg Glu Met Arg Gly Phe Tyr Tyr Ile Trp Asp Met
1               5                   10                  15

Ser His Leu Thr Leu Gln Leu His Val Val Ile Ala Leu Tyr Val Leu
            20                  25                  30

Phe Arg Trp Cys His Gly Gly Ile Thr Ser Ile Asn Cys Ser Gly Asp
        35                  40                  45

Met Trp Val Glu Pro Gly Glu Ile Phe Gln Met Gly Met Asn Val Ser
    50                  55                  60

Ile Tyr Cys Gln Glu Ala Leu Lys His Cys Arg Pro Arg Asn Leu Tyr
```

-continued

```
                65                  70                  75                  80
        Phe Tyr Lys Asn Gly Phe Lys Glu Glu Phe Asp Ile Thr Arg Ile Asn
                        85                  90                  95

Arg Thr Thr Ala Arg Ile Trp Tyr Lys Gly Phe Ser Glu Pro His Ala
                        100                 105                 110

Tyr Met His Cys Thr Ala Glu Cys Pro Gly His Phe Gln Glu Thr Leu
                        115                 120                 125

Ile Cys Gly Lys Asp Ile Ser Ser Gly His Pro Pro Asp Ala Pro Ser
                        130                 135                 140

Asn Leu Thr Cys Val Ile Tyr Glu Tyr Ser Gly Asn Met Thr Cys Thr
        145                 150                 155                 160

Trp Asn Thr Gly Lys Pro Thr Tyr Ile Asp Thr Lys Tyr Ile Val His
                        165                 170                 175

Val Lys Ser Leu Glu Thr Glu Glu Gln Gln Tyr Leu Ala Ser Ser
                        180                 185                 190

Tyr Val Lys Ile Ser Thr Asp Ser Leu Gln Gly Ser Arg Lys Tyr Leu
                        195                 200                 205

Val Trp Val Gln Ala Val Asn Ser Leu Gly Met Glu Asn Ser Gln Gln
                        210                 215                 220

Leu His Val His Leu Asp Asp Ile Val Ile Pro Ser Ala Ser Ile Ile
        225                 230                 235                 240

Ser Arg Ala Glu Thr Thr Asn Asp Thr Val Pro Lys Thr Ile Val Tyr
                        245                 250                 255

Trp Lys Ser Lys Thr Met Ile Glu Lys Val Phe Cys Glu Met Arg Tyr
                        260                 265                 270

Lys Thr Thr Thr Asn Gln Thr Trp Ser Val Lys Glu Phe Asp Ala Asn
                        275                 280                 285

Phe Thr Tyr Val Gln Gln Ser Glu Phe Tyr Leu Glu Pro Asp Ser Lys
                        290                 295                 300

Tyr Val Phe Gln Val Arg Cys Gln Glu Thr Gly Lys Arg Asn Trp Gln
        305                 310                 315                 320

Pro Trp Ser Ser Pro Phe Val His Gln Thr Ser Gln Glu Thr Gly Lys
                        325                 330                 335

Arg Asn Trp Gln Pro Trp Ser Ser Pro Phe Val His Gln Thr Ser Gln
                        340                 345                 350

Thr Val Ser Gln Val Thr Ala Lys Ser Ser His Glu Pro Gln Lys Met
                        355                 360                 365

Glu Met Leu Ser Ala Thr Ile Phe Arg Gly His Pro Ala Ser Gly Asn
                        370                 375                 380

His Gln Asp Ile Gly Leu Leu Ser Gly Met Val Phe Leu Ala Ile Met
        385                 390                 395                 400

Leu Pro Ile Phe Ser Leu Ile Gly Ile Phe Asn Arg Ser Leu Arg Ile
                        405                 410                 415

Gly Ile Lys Arg Lys Val Leu Leu Met Ile Pro Lys Trp Leu Tyr Glu
                        420                 425                 430

Asp Ile Pro Asn Met Glu Asn Ser Asn Val Ala Lys Leu Leu Gln Glu
                        435                 440                 445

Lys Ser Val Phe Glu Asn Asp Asn Ala Ser Gln Ala Leu Tyr Val
                        450                 455                 460

Asp Pro Val Leu Thr Glu Ile Ser Glu Ile Ser Pro Leu Glu His Lys
        465                 470                 475                 480

Pro Thr Asp Tyr Lys Glu Glu Arg Leu Thr Gly Leu Leu Glu Thr Arg
                        485                 490                 495
```

-continued

```
Asp Cys Pro Leu Gly Met Leu Ser Thr Ser Ser Val Val Tyr Ile
            500                 505                 510

Pro Asp Leu Asn Thr Gly Tyr Lys Pro Gln Val Ser Asn Val Pro Pro
        515                 520                 525

Gly Gly Asn Leu Phe Ile Asn Arg Asp Glu Arg Asp Pro Thr Ser Leu
530                 535                 540

Glu Thr Thr Asp Asp His Phe Ala Arg Leu Lys Thr Tyr Pro Asn Phe
545                 550                 555                 560

Gln Phe Ser Ala Ser Ser Met Ala Leu Leu Asn Lys Thr Leu Ile Leu
                565                 570                 575

Asp Glu Leu Cys Leu Val Leu Asn Gln Gly Phe Asn Ser Leu Asp
            580                 585                 590

Ile Lys Asn Ser Arg Gln Glu Glu Thr Ser Ile Val Leu Gln Ser Asp
                595                 600                 605

Ser Pro Ser Glu Thr Ile Pro Ala Gln Thr Leu Leu Ser Asp Glu Phe
        610                 615                 620

Val Ser Cys Leu Ala Ile Gly Asn Glu Asp Leu Pro Ser Ile Asn Ser
625                 630                 635                 640

Tyr Phe Pro Gln Asn Val Leu Glu Ser His Phe Ser Arg Ile Ser Leu
                645                 650                 655

Phe Gln Lys

<210> SEQ ID NO 3
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 3

Trp Asn Ala Gly Lys Leu Thr Tyr Ile Asp Thr Lys Tyr Val Val
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 4

Leu Thr Tyr Ile Asp Thr Lys Tyr Val Val His Val Lys Ser Leu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 5

Lys Tyr Leu Val Trp Val Gln Ala Ala Asn Ala Leu Gly Met Glu
1               5                   10                  15

<210> SEQ ID NO 6
<211> LENGTH: 326
<212> TYPE: DNA
<213> ORGANISM: Artificial Sequence
<220> FEATURE:
<223> OTHER INFORMATION: Synthetic polynucleotide
```

<400> SEQUENCE: 6

```
gtcctaaaaa tatgatggtg aatccagttc ccagggttta gagcggcccc tgtgatgatt    60
taccagcgat acaaaccact tcccttgtca gaatgtcacg aactgaaaac tgagctgccg   120
ggtcaataag cagagaagag catgcgcatg cgcggggtag gctgtctcca tgcgggtgga   180
ggagccgccc ggtggctgga ttgaccatgg gtacagggcc ggtgggggcc cccccactta   240
cacctgtgtg cacaatgttt cctggtgagt gtggagagtt ctgacaggca tgggagaaaa   300
gcactaacca gaccacaggt cttgag                                        326
```

<210> SEQ ID NO 7
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 7

```
Gly Ile Thr Asn Ile Asn Cys Ser Gly His Ile Trp Val Glu Pro Ala
1               5                   10                  15

Thr Ile Phe Lys Met Gly Met Asn Ile Ser Ile Tyr Cys Gln Ala Ala
            20                  25                  30

Ile Lys Asn Cys Gln Pro Arg Lys Leu His Phe Tyr Lys Asn Gly Ile
        35                  40                  45
```

<210> SEQ ID NO 8
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 8

```
Gly Ile Thr Ser Ile Asn Cys Ser Gly Asp Met Trp Val Glu Pro Gly
1               5                   10                  15

Glu Ile Phe Gln Met Gly Met Asn Val Ser Ile Tyr Cys Gln Glu Ala
            20                  25                  30

Leu Lys His Cys Arg Pro Arg Asn Leu Tyr Phe Tyr Lys Asn Gly Phe
        35                  40                  45
```

<210> SEQ ID NO 9
<211> LENGTH: 54
<212> TYPE: PRT
<213> ORGANISM: Artificial Sequence
<220> FEATURE:
<223> OTHER INFORMATION: Synthetic polypeptide

<400> SEQUENCE: 9

```
Lys Glu Arg Phe Gln Ile Thr Arg Ile Asn Lys Thr Thr Ala Arg Leu
1               5                   10                  15

Trp Tyr Lys Asn Phe Leu Glu Pro His Ala Ser Met Tyr Cys Thr Ala
            20                  25                  30

Glu Cys Pro Lys His Phe Gln Glu Thr Leu Ile Cys Gly Lys Asp Ile
        35                  40                  45

Ser Ser Gly Tyr Pro Pro
    50
```

<210> SEQ ID NO 10
<211> LENGTH: 54
<212> TYPE: PRT

<213> ORGANISM: Artificial Sequence
<220> FEATURE:
<223> OTHER INFORMATION: Synthetic polypeptide

<400> SEQUENCE: 10

Lys Glu Glu Phe Asp Ile Thr Arg Ile Asn Arg Thr Thr Ala Arg Ile
1               5                   10                  15

Trp Tyr Lys Gly Phe Ser Glu Pro His Ala Tyr Met His Cys Thr Ala
            20                  25                  30

Glu Cys Pro Gly His Phe Gln Glu Thr Leu Ile Cys Gly Lys Asp Ile
        35                  40                  45

Ser Ser Gly His Pro Pro
    50

<210> SEQ ID NO 11
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 11

Asp Ile Pro Asp Glu Val Thr Cys Val Ile Tyr Glu Tyr Ser Gly Asn
1               5                   10                  15

Met Thr Cys Thr Trp Asn Ala Gly Lys Leu Thr Tyr Ile Asp Thr Lys
            20                  25                  30

Tyr Val Val His Val Lys Ser Leu Glu Thr Glu Glu Gln Gln Tyr
        35                  40                  45

Leu Thr Ser Ser Tyr Ile Asn Ile Ser Thr Asp Ser Leu Gln Gly Gly
    50                  55                  60

Lys
65

<210> SEQ ID NO 12
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 12

Asp Ala Pro Ser Asn Leu Thr Cys Val Ile Tyr Glu Tyr Ser Gly Asn
1               5                   10                  15

Met Thr Cys Thr Trp Asn Thr Gly Lys Pro Thr Tyr Ile Asp Thr Lys
            20                  25                  30

Tyr Ile Val His Val Lys Ser Leu Glu Thr Glu Glu Gln Gln Tyr
        35                  40                  45

Leu Ala Ser Ser Tyr Val Lys Ile Ser Thr Asp Ser Leu Gln Gly Ser
    50                  55                  60

Arg
65

<210> SEQ ID NO 13
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 13

Lys Tyr Leu Val Trp Val Gln Ala Ala Asn Ala Leu Gly Met Glu Glu

```
                1               5                  10                 15
Ser Lys Gln Leu Gln Ile His Leu Asp Asp Ile Val Ile Pro Ser Ala
                   20                  25                 30

Ala Val Ile Ser Arg Ala Glu Thr Ile Asn Ala Thr Val Pro Lys Thr
           35                  40                 45

Ile Ile Tyr Trp Asp Ser Gln Thr Thr Ile Glu Lys Val Ser Cys
       50                  55                 60

<210> SEQ ID NO 14
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 14

Lys Tyr Leu Val Trp Val Gln Ala Val Asn Ser Leu Gly Met Glu Asn
1               5                  10                 15

Ser Gln Gln Leu His Val His Leu Asp Asp Ile Val Ile Pro Ser Ala
                   20                  25                 30

Ser Ile Ile Ser Arg Ala Glu Thr Thr Asn Asp Thr Val Pro Lys Thr
           35                  40                 45

Ile Val Tyr Trp Lys Ser Lys Thr Met Ile Glu Lys Val Phe Cys
       50                  55                 60

<210> SEQ ID NO 15
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 15

Glu Met Arg Tyr Lys Ala Thr Thr Asn Gln Thr Trp Asn Val Lys Glu
1               5                  10                 15

Phe Asp Thr Asn Phe Thr Tyr Val Gln Gln Ser Glu Phe Tyr Leu Glu
                   20                  25                 30

Pro Asn Ile Lys Tyr Val Phe Gln Val Arg Cys Gln Glu Thr Gly Lys
           35                  40                 45

Arg Tyr Trp Gln Pro Trp Ser Ser Leu Phe
       50                  55

<210> SEQ ID NO 16
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 16

Glu Met Arg Tyr Lys Thr Thr Thr Asn Gln Thr Trp Ser Val Lys Glu
1               5                  10                 15

Phe Asp Ala Asn Phe Thr Tyr Val Gln Gln Ser Glu Phe Tyr Leu Glu
                   20                  25                 30

Pro Asp Ser Lys Tyr Val Phe Gln Val Arg Cys Gln Glu Thr Gly Lys
           35                  40                 45

Arg Asn Trp Gln Pro Trp Ser Ser Pro Phe
       50                  55

<210> SEQ ID NO 17
```

```
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 17

Phe His Lys Thr Pro Glu Thr Val Pro Gln Val Thr Ser Lys Ala Phe
1               5                   10                  15

Gln His Asp Thr Trp Asn Ser Gly Leu Thr Val Ala Ser Ile Ser Thr
            20                  25                  30

Gly His Leu Thr Ser Asp Asn Arg Gly Asp Ile Gly
        35                  40

<210> SEQ ID NO 18
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 18

Val His Gln Thr Ser Gln Glu Thr Gly Lys Arg Asn Trp Gln Pro Trp
1               5                   10                  15

Ser Ser Pro Phe Val His Gln Thr Ser Gln Thr Val Ser Gln Val Thr
            20                  25                  30

Ala Lys Ser Ser His Glu Pro Gln Lys Met Glu Met Leu Ser Ala Thr
        35                  40                  45

Ile Phe Arg Gly His Pro Ala Ser Gly Asn His Gln Asp Ile Gly
    50                  55                  60

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19
gacctggaac gtgaaagaat t                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 20
gcaaagcgtt tcagcatgat a                                             21

<210> SEQ ID NO 21
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 21
gattccgaaa tggctgtatg a                                             21

<210> SEQ ID NO 22
<211> LENGTH: 21
<212> TYPE: DNA
```

<213> ORGANISM: Artificial Sequence
<220> FEATURE:
<223> OTHER INFORMATION: Synthetic polynucleotide

<400> SEQUENCE: 22
gaaatggctg tatgaagata t                                        21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
gcgaactgat gaacaacaac a                                        21

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24
ggtgtatatt ccggatctga a                                        21

<210> SEQ ID NO 25
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 25
ggatctgaac accggctata a                                        21

<210> SEQ ID NO 26
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 26
gcagccatct gagcaacaac a                                        21

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
gcagccatct gagcaacaac a                                        21

<210> SEQ ID NO 28
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 28
gcaacaacaa cgaaattacc a                                        21

<210> SEQ ID NO 29
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 29
gcgaactgag cctgattctg a                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 30
gggcattgtg aacgaagaac t                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 31
gccgagcatt aacacctatt t                                              21

<210> SEQ ID NO 32
<211> LENGTH: 76
<212> TYPE: PRT
<213> ORGANISM: Artificial Sequence
<220> FEATURE:
<223> OTHER INFORMATION: Synthetic polypeptide

<400> SEQUENCE: 32

Leu Asn Gln Gly Glu Cys Ser Ser Pro Asp Ile Gln Asn Ser Val Glu
1               5                   10                  15

Glu Glu Thr Thr Met Leu Leu Glu Asn Asp Ser Pro Ser Glu Thr Ile
            20                  25                  30

Pro Glu Gln Thr Leu Leu Pro Asp Glu Phe Val Ser Cys Leu Gly Ile
        35                  40                  45

Val Asn Glu Glu Leu Pro Ser Ile Asn Thr Tyr Phe Pro Gln Asn Ile
    50                  55                  60

Leu Glu Ser His Phe Asn Arg Ile Ser Leu Leu Glu
65                  70                  75

<210> SEQ ID NO 33
<211> LENGTH: 76
<212> TYPE: PRT
<213> ORGANISM: Homo sapiens

<400> SEQUENCE: 33

Leu Asn Gln Gly Glu Cys Ser Ser Pro Asp Ile Gln Asn Ser Val Glu
1               5                   10                  15

Glu Glu Thr Thr Met Leu Leu Glu Asn Asp Ser Pro Ser Glu Thr Ile
            20                  25                  30

Pro Glu Gln Thr Leu Leu Pro Asp Glu Phe Val Ser Cys Leu Gly Ile
        35                  40                  45

```
Val Asn Glu Glu Leu Pro Ser Ile Asn Thr Tyr Phe Pro Gln Asn Ile
    50                  55                  60

Leu Glu Ser His Phe Asn Arg Ile Ser Leu Leu Glu
65                  70              75
```

IL-23R ANTAGONISTS TO REPROGRAM INTRATUMORAL T REGULATORY CELLS INTO EFFECTOR CELLS

RELATED APPLICATIONS

This application is a national stage filing under 35 U.S.C. 371 of International Patent Application Serial No. PCT/US2018/030636, filed May 2, 2018, entitled "IL-23R ANTAGONISTS TO REPROGRAM INTRATUMORAL T REGULATORY CELLS INTO EFFECTOR CELLS", which claims the benefit under 35 U.S.C. § 119(e) of U.S. Provisional Patent Application No. 62/500,443, filed on May 2, 2017, entitled "IL-23R ANTAGONISTS TO REPROGRAM INTRATUMORAL T REGULATORY CELLS INTO EFFECTOR CELLS," the entire contents of each of which are incorporated by reference herein.

FEDERALLY SPONSORED RESEARCH

This invention was made with government support under grant number R01AI037562 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jul. 21, 2020, is named D050470127US01-SEQ-MAT and is 23 kilobytes in size.

BACKGROUND OF INVENTION

Regulatory T cells (Treg cells) are critically important for maintenance of a balanced immune system, in part because they help to dampen excessive immune responses and prevent autoimmunity. However, immune suppression exerted by Treg cells can impede anti-tumor immune responses and promote cancer growth. The efficacy of several successful immunotherapies has been associated with depletion or blockade of CD4 Treg cells (Mahoney et al., Nat Rev Drug Discov 14:561-584).

SUMMARY OF INVENTION

The disclosure relates to selective induction of Treg cell phenotypic instability and selective conversion of intratumoroal, but not systemic, Treg cells into T effector cells (Teff cells). The disclosure relates to compositions for modulating the differentiation of Treg cells. The disclosure is based, in part, on the surprising discovery that the IL-23R cytokine receptor subunit is expressed on Treg cells and that inhibition of IL-23R induces differentiation of Treg cells (e.g., to Teff cells). Inducing Treg cell differentiation is particularly useful, for example, in the context of treating cancer.

In one aspect, disclosed herein are methods for treating cancer in a human subject. The methods involve administering to a human subject in need thereof an agent that decreases IL-23R activity and does not decrease IL-12Rβ activity, in an amount effective to treat the cancer. In embodiments, the agent is a polypeptide, nucleic acid, or small molecule. In some embodiments, the agent binds the extracellular domain of IL-23R.

In some embodiments, the agent is a human or humanized monoclonal antibody. In some embodiments, the antibody binds IL-23R and does not bind IL-12Rβ. In some embodiments, the antibody has 100-fold, 1,000-fold, or 10,000-fold greater binding affinity for IL-23R than for IL-12Rβ. In some embodiments, the antibody is free of antibody-dependent cellular cytotoxicity (ADCC) activity. In some embodiments, the antibody has an IgG4 heavy chain immunoglobulin constant domain.

In some embodiments, the agent binds a nucleic acid coding for or expressing IL-23R.

In some embodiments, the methods further comprise administering to the human subject an immunomodulatory agent. In some embodiments, the immunomodulatory agent is an immune checkpoint inhibitor. In some embodiments, immune checkpoint inhibitor is an antagonist of a molecule selected from the group consisting of PD-1, TIM-3, TIGIT, VISTA, A2AR, B7-H3, B7-H4, BTLA, CTLA-4, IDO, KIR and LAG3. In some embodiments, the immunomodulatory agent in an antagonist of inhibitory macrophages and/or dendritic cells.

In some embodiments, the method further comprises administering an agent that inhibits cancer cell growth.

In another aspect, disclosed herein are methods for inducing differentiation of a Treg cell to a Teff cell. The methods involve contacting the Treg cell in vitro with an agent that decreases IL-23R activity and does not decrease IL-12Rβ activity. In some embodiments, the agent is a polypeptide, nucleic acid, or small molecule.

In some embodiments, the agent binds the extracellular domain of IL-23R. In some embodiments, the agent is a human or humanized monoclonal antibody. In some embodiments, the antibody binds IL-23R and does not bind IL-12Rβ. In some embodiments, the antibody has 100-fold, 1,000-fold, or 10,000-fold greater binding affinity for IL-23R than for IL-12Rβ. In some embodiments, the antibody is free of antibody-dependent cellular cytotoxicity (ADCC) activity. In some embodiments, the antibody has an IgG4 heavy chain immunoglobulin constant domain.

In some embodiments, the agent binds a nucleic acid coding for or expressing IL-23R.

In some embodiments, the Treg cell is a CD4+ Treg cell, a CD8+ Treg cell, a Helios+ Treg cell, or a CD25+ and FoxP3+ Treg cell.

In some embodiments, the method further comprises contacting the Treg cell in the presence of one or more inflammatory cytokines. In some embodiments, the one or more inflammatory cytokines is selected from the group consisting of IL-2, IL-4, and combination thereof.

In another aspect, disclosed herein are methods for identifying a compound that will convert a Treg cell into a Teff cell. The methods comprise:
 contacting a Treg cell with a test compound;
 measuring IL-23R activity in the cell; and
 measuring IL-12Rβ activity in the cell;
 wherein the test compound is a compound for converting a Treg cell into an effector cell if:
(i) the IL-23R activity is decreased relative to a control cell that has been treated with a compound known to not decrease IL-23R activity and IL-12Rβ activity; and
(ii) the IL-12Rβ activity is not decreased relative to the control cell.

In some embodiments, the methods further comprise measuring FoxP3 activity in the cell.

In some embodiments, the methods further comprise measuring an effector cytokine produced by the cell. In some embodiments, the effector cytokine is TNF-α, IFN-γ, IL-17, IL-10, or IL-2.

In some embodiments, the test compound is selected from the group consisting of a polypeptide, a nucleic acid and a small molecule.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows tumor volume (mm$^3$) of subcutaneously injected B16/F10 or MC38 cells. FIG. 1B shows intratumoral CD8 and IFN-γ expression. Representative FACS plots from triplicate experiments are shown. P value: *<0.05.

FIG. 2A shows the Helios binding site in the first intron of the STAT5b gene locus. FIG. 2B shows the Helios binding motifs from genome wide analysis of Helios binding sites.

FIG. 3A shows the B16/F10 tumor growth (volume mm$^3$) curve beginning with first appearance of tumor (day 10). FIG. 3B shows the proportion of splenic and tumor infiltrating nTregs positive for FoxP3 expression. FIG. 3C shows the proportion of splenic and tumor infiltrating nTregs positive for INF-γ expression. Representative FACS plots from triplicate experiments are shown.

FIG. 4A shows expression of FoxP3 and FIG. 4B shows expression of CD73$^{high}$FR4$^{high}$ cells. Both FIGS. 4A-4B show representative FACS plots from triplicate experiments. P value: *<0.05, **, <0.01.

FIG. 5A shows a loss of Helios expression upon addition of IL-4. FIG. 5B shows the dose dependent IL-4-mediated shift in Helios$^+$ TIGIT$^+$ nTreg proportion. The cells were gated on TCR$^+$CD4$^+$CD25$^+$FoxP3$^+$.

FIG. 10A shows tumor growth curves. Intratumoral and splenic Treg were assessed for IFN-γ (gated on FoxP3$^+$ cells) (FIG. 10B) and FoxP3 (gated on CD4$^+$CD25$^+$ cells) (FIG. 10C) expression. Student's T test: *** p≤0.001.

FIG. 11A shows the expression of FoxP3 by Treg (% reduction) and FIG. 11B shows the fold-increase IFN-γ$^+$ Treg cells after co-culture with IL-23 associated large molecules. Average±SEM-ANOVA: *p<0.001 *p<0.0001.

FIG. 25A shows the protocol for the in vivo experiment. FIGS. 25B-25C show tumor outgrowth curves. FIG. 25B shows the individual growth curves. The number in the bottom corner indicates how many mice developed tumors/total sample size (day 21). FIG. 25C illustrates the mean tumor outgrowth±SD. Student's T Test (day 21). FIG. 25D shows that anti-IL-23R antibody treatment delays tumor outgrowth. Tumor outgrowth in isotype antibody and anti-IL-23R antibody treated mice is shown. Treatment (100 mg/mouse using an intraperitoneal injection) isotype (n=3) anti-IL-23R (n=3) was given on day 8, 11, and 14 as indicated by the arrows (↓). The tumor volume ($mm^3$) is represented as an average (left) and as individual values (right). Student's T test (day 16 data points). FIG. 25E shows the tumor out growth curve treatment given intraperitoneally (100 μg/mouse) on day 8, 11 and 14.

FIG. 26A shows CD8 activity as shown by IFN-γ expression. (Representative FACs plots gated on $TCR^+CD8^+$ cells are shown. FIG. 26B shows intratumoral Treg conversion as indicated by IFN-γ expression Representative FACs plots gated on $TCR^+CD4^+CD25^+FoxP3^+$ cells are shown. ANOVA or Student's T test: * p<0.05 *p<0.001 **p<0.0001.

FIG. 34A shows percent change of FOXP3 expression. FIG. 34B shows percent change of IFN-gamma expression. Graphs show combined data from three experiments (mean±SEM ANOVA p<0.05 * p<0.01  p<0.001 * p<0.0001 ****).

FIG. 39A shows FoxP3 expression levels and FIG. 39B shows IFN-γ expression levels in IL-23R$^{KO}$ and C57BL/6 Tregs.

FIGS. 44A-44C show that treatment with anti-IL-23R antibody provides a reduction in the pSTAT5:pSTAT3 ratio compared to treatment with isotype. STAT5 expression is shown in FIG. 44A and STAT3 expression is shown in FIG. 44B. FIG. 44D shows that treatment with anti-IL-23R antibody decreases the numbers of CD25+ FoxP3+ Tregs, compared to treatment with isotype. FIGS. 44E-44F show that treatment with anti-IL-23R antibody increases IFN-γ expression and decreases IL-23R expression levels.

FIG. 46A shows that tumor growth, as assessed by tumor volume, progresses with delayed kinetic in STAT3$^{KO}$ Treg mice than it does in STAT3$^{WT}$ Treg mice. FIGS. 46B-46C show that STAT3$^{KO}$ Treg mice have increased expression levels of CD69 and IFN-γ compared to STAT3$^{WT}$Treg mice in CD8 TIL.

FIG. 47A shows that treatment of C57BL/6 mice with anti-IL-23R antibody reduces tumor volumes compared to C57BL/6 mice treated with isotype. FIG. 47B shows that treatment of Rag2$^{-/-}$ mice that have been injected with Tregs alone or in conjunction with CD8+ T cells with anti-IL-23R antibody reduces tumor volume compared to treatment with isotype.

DETAILED DESCRIPTION OF INVENTION

Figure 1A:
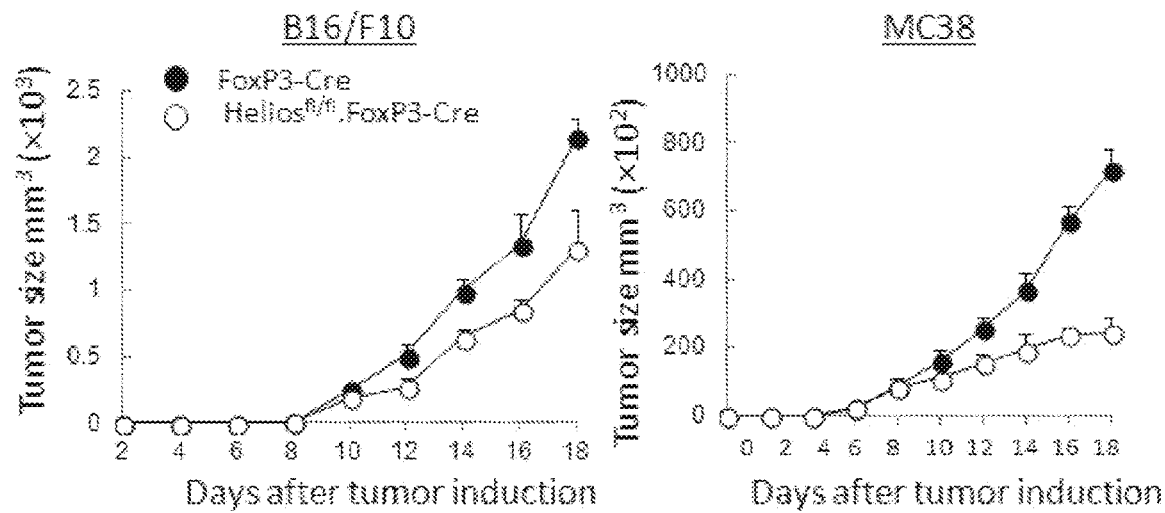
FIGS. 1A-1B show that Treg specific Helios$^{-/-}$ mice exhibit elevated antitumor immunity. Treg specific Helios and Helios$^{-/-}$ mice (Helios$^{WT}$ and Helios$^{KO}$ respectively) were inoculated with B16/F10 or MC38 cancer cell lines and assessed for tumor progression and cytotoxic T cell activity.

The present disclosure, in one aspect, relates to the surprising discovery that IL-23R modulates Treg differentiation, and in particular, that inhibition of IL-23R induces Treg differentiation. The IL-23R cytokine receptor subunit dimerizes with IL-12β1 to form the IL-23 receptor, which binds the IL-23 cytokine. It has surprisingly been found that IL-23R is expressed on Treg cells the and inhibition of IL-23R induces differentiation of these Treg cells (e.g., to Teff cells).

The present disclosure, in another aspect, relates to the surprising discovery that IL-23R modulates cancer. Regulatory T cells are critically important for maintenance of a balanced immune system, in part because they help to dampen excessive immune responses and prevent autoimmunity. However, immune suppression exerted by Treg can impede anti-tumor immune responses and promote cancer growth. Inducing differentiation of Treg via decreasing IL-23R activity has the capacity to slow cancer progression and agents that decrease IL-23R activity represent novel therapeutics for treating cancer.

Thus, in one aspect, the present disclosure provides agents for treating cancer by decreasing IL-23R activity. In another aspect, the present disclosure provides agents for inducing differentiation of a regulatory T (Treg) cell to an effector T cell by decreasing IL-23R activity. Such agents can include antibodies, polypeptides, nucleic acids, or small molecules. Interleukin-23 Receptor (IL-23R)

IL-23R mediates signaling by IL-23. Interleukin-23 (IL-23) is a heterodimeric cytokine comprised of two subunits, p19 which is unique to IL-23, and p40, which is shared with IL-12. IL-23 mediates signaling by binding to the heterodimeric IL-23 receptor, comprised of an IL-23R subunit and an IL-12Rβ1, which is shared by the IL-12 receptor. The p19 subunit of IL-23 interacts with the IL-23R subunit of the IL-23 receptor and the p40 subunit of IL-23 interacts with the IL-12Rβ1 subunit of the IL-23 receptor. IL-23 interacts with the IL-23 receptor at the extracellular region.

IL-23-R is a protein with isoforms ranging in size from 20 kDa to 43 kDa. The sequence of IL-23-R can be found at NCBI Ref. No. NM_144701.2.

IL-23R associates with Janus kinase 2 (Jak2) and in a ligand-dependent manner with Signal transducer and activator of transcription STAT3. IL-12Rβ1 interacts directly with Tyrosine kinase 2 (Tyk2).

IL-23 induced activation of STAT3 leads to direct binding of phosphorylated STAT3 to Interleukin-17 (IL-17) and Interleukin 17F (IL-17F) promoters. STAT3 up-regulates the expression of Retinoic Acid Receptor-Related Orphan Receptor Gamma-T (ROR-gamma), a Th17 specific transcriptional regulator that is critical for the expression of two members of Interleukin-17 family, IL-17A (IL-17) and IL-17F. IL-23 induced JAK2 activation triggers Phosphoinositide-3-kinase (PI3K)/RAC-alpha serine/threonine kinase (AKT) and Nuclear factor kappaB (NF-kB) pathways which are required for IL-17 production. PI3K/AKT pathway is involved in STAT3 phosphorylation through an undetermined mechanism.

In embodiments, an agent described herein decreases IL-23R activity. In general, a decrease means any statistically significant decrease in activity by any one or more measures. The measures of activity may be direct or indirect, using one or more of the measures described herein or otherwise known to those of ordinary skill in the art. The measure may be of a cell in a resting state or a cell contacted with exogenous ligand to IL-23R. The measure may be as illustrated in the examples. The measure typically will be carried out in vitro, to establish that the agent has the desired properties of decreasing IL-23R activity but not IL-12R activity. Such agents then can be administered in therapeutically effective amounts. Alternatively, the measure may be an improvement in the subject being treated, such as the slowing of progression of, the halting of the growth of, or the shrinkage of the cancer.

In some embodiments, IL-23R activity is decreased relative to a control at least 5%, 10%, 15%, 20%, 25%, 30%, 35%, 40%, 45%, 50%, 55%, 60%, 65%, 70%, 75%, and even more than 75%. In some embodiments, IL-23R activity is decreased 1%-5%, 1%-10%, 5%-10%, 5%-25%, 10%-50%, 20%-40%, 40%-60%, 50%-90%, 50%-70%, 60%-80%, 80%-90%, 90%-95%, 90%-99%, or 95%-99%.

In some embodiments, an agent described herein is administered to a subject and IL-23R activity is decreased in the subject. In some embodiments, the agent is administered to a subject and IL-23R activity is decreased relative to the level of IL-23R activity prior to administration of the agent. In some embodiments, the IL-23R activity is decreased relative to the level of IL-23R activity in the subject 30 minutes, 1 hour, 2 hours, 3 hours, 4 hours, 5 hours 6 hours 12 hours 24 hours, 2 days, 3 days, 4 days, 5 days 6 days, 1 week, 2 weeks, 3 weeks, or 4 weeks or more prior to administration of the agent. In some embodiments, multiple doses of the agent are administered to a subject and IL-23R activity is decreased relative to the level of IL-23R activity prior to the first administration of the agent, e.g., the beginning of treatment. In some embodiments, the IL-23R activity is decreased relative to the level of IL-23R activity in the subject 30 minutes, 1 hour, 2 hours, 3 hours, 4 hours, 5 hours, 6 hours 12 hours 24 hours, 2 days, 3 days, 4 days, 5 days 6 days, 1 week, 2 weeks, 3 weeks, or 4 weeks or more prior to the first administration of the agent. In some embodiments, multiple doses of the agent are administered to a subject and IL-23R activity is decreased relative to the level of IL-23R activity prior to the current administration of the agent. In some embodiments, the IL-23R activity is decreased relative to the level of IL-23R activity in the subject 30 minutes, 1 hour, 2 hours, 3 hours, 4 hours, 5 hours, 6 hours 12 hours 24 hours, 2 days, 3 days, 4 days, 5 days 6 days, 1 week, 2 weeks, 3 weeks, or 4 weeks or more prior to the current administration of the agent.

In some embodiments, the agent is administered to a subject and IL-23R activity is decreased relative to the level of IL-23R activity in a control subject who is not treated with the agent. In some embodiments, the control subject has the same or a similar type of cancer as the subject. In some embodiments, the control subject has the same or a similar severity of cancer as the subject. In some embodiments, the control subject does not have cancer. In some embodiments, the control subject is the same or a similar age as the subject. In some embodiments, the control subject is the same sex as the subject. In some embodiments, the control subject is related to the subject. In some embodiments, the control subject is a twin of the subject.

In some embodiments, the agent is administered to a subject in amounts effective to treat cancer in the subject. Effective amounts are described in greater detail below.

In some embodiments, Treg cells are contacted in vitro with an agent described herein and IL-23R activity is decreased. In some embodiments, IL-23R activity is decreased relative a control cell, e.g., a cell treated with a compound known to not decrease IL-23R activity and IL-12Rβ activity. In some embodiments, IL-23R activity is decreased relative a cell of the same clonal population, e.g., of the same culture, that are not administered the agent. In some embodiments, the IL-23R activity of the cell of the same clonal population is measured simultaneously or near simultaneously with the IL-23R activity of the Treg cell. In some embodiments, the IL-23R activity of the cell of the same clonal population is measured before or after the IL-23R activity of the Treg cell. In some embodiments, the IL-23R activity is decreased relative to cells of the same cell type, e.g., are derived from the same source, that are not administered the agent.

In some embodiments, a decrease in IL-23R activity comprises a decrease in expression of FoxP3, Helios, IL-17A, IL-17F, ROR-gamma, and/or IL-23. In some embodiments, expression of FoxP3, Helios, IL-17A, IL-17F, ROR-gamma, and/or IL-23 is decreased 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In some embodiments, expression of FoxP3, Helios, IL-17A, IL-17F, ROR-gamma, and/or IL-23 is decreased more than 1%, 5%, 10%, 15%, 20%, 25%, 30%, 35%, 40%, 45%, 50%, 55%, 60%, 65%, 70%, 75%, 80%, 85%, 90%. In some embodiments, expression of FoxP3, Helios, IL-17A, IL-17F, ROR-gamma, and/or IL-23 is decreased 1%-5%, 1%-10%, 5%-10%, 5%-25%, 10%-50%, 20%-40%, 40%-

60%, 50%-90%, 50%-70%, 60%-80%, 80%-90%, 90%-95%, 90%-99%, 90%-99%, or 95%-99%.

Gene expression can be measured at either the RNA or protein level. Assays for detecting RNA include, but are not limited to, Northern blot analysis, RT-PCR, sequencing technology, RNA in situ hybridization (using e.g., DNA or RNA probes to hybridize RNA molecules present in the sample), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer with addressable location, such as Affymetrix microarray (Affymetrix®, Santa Clara, Calif.)).

Assays for detecting protein levels include, but are not limited to, immunoassays (also referred to herein as immune-based or immuno-based assays, e.g., Western blot, ELISA, proximity extension assays, and ELISpot assays), Mass spectrometry, and multiplex bead-based assays. Other examples of protein detection and quantitation methods include multiplexed immunoassays as described for example in U.S. Pat. Nos. 6,939,720 and 8,148,171, and published U.S. Patent Application No. 2008/0255766, and protein microarrays as described for example in published U.S. Patent Application No. 2009/0088329.

In some embodiments, IL-23 activity can be measured by measuring IL-17 and/or interferon-gamma secretion following treatment of activated preipheral blood mononuclear cells (Dallas et al., Drug Metabolism and Disposition, 2013, 41:689-693). In some embodiments, IL-23 activity can be measured by measuring differentiation of CD4+ T cells to IL-17-producing pathogenic Th17 cells. (Reddy et al., Cell Immunol, 2007, 47:1-11).

In some embodiments, a decrease in IL-23R activity stimulates Teff development (i.e., Treg differentiation) as is described in further detail below.

Interleukin 12

Interleukin-12 (IL-12) is a heterodimeric molecule composed of p35 and p40 subunits. IL-12 plays a role in the differentiation of naïve T cells into T-helper type 1 CD4 lymphocytes that secrete IFNγ. IL-12 is also important for T cell dependent immune and inflammatory responses in vivo. The IL-12 receptor (IL-12Rβ) is composed of IL-12Rβ1 and IL-12Rβ2 subunits.

The main role of IL-12 is activation of interferon gamma production. Upon binding to its receptor, IL-12 activates Janus family kinases Tyrosine kinase 2 (Tyk2) and Janus kinase 2 (Jak2). Interleukin 12 receptor, beta 1 (IL-12Rβ1) binds Tyk2, whereas Interleukin 12 receptor, beta 2 (IL-12Rβ2) associates with Jak2. Jak2 phosphorylates the tyrosine residues of STAT3 and STAT4. They translocate to the nucleus and bind to the promoter site of IFN-gamma. STAT4 also induces transcription of IL-12Rβ2, IL18-Rβ1, Interferon regulatory factor 1 (IRF1), Interleukin 2 receptor, alpha (IL-2R), and GCNT1 glucosaminyl (N-acetyl) transferase 1 core 2 (GENT).

In embodiments, agents described herein do not appreciably decrease IL-12Rβ activity. It will be understood by one of ordinary skill in the art, that according to the invention, agents are employed that decrease IL-23R activity and do not decrease IL-12Rβ activity. In general, it is expected that such agents will not appreciably decrease IL-12Rβ activity because the agents do not interact directly with IL-12Rβ. The IL-12Rβ activity, therefore, will not vary more than would be expected in control cells.

In embodiments, the absence of a decrease in activity may be established by any one or more measures. The measures of activity may be direct or indirect, using one or more of the measures described herein or otherwise known to those of ordinary skill in the art. The measure may be of a cell in a resting state or a cell contacted with exogenous ligand to IL-12R. The measure may be as illustrated in the examples. The measure typically will be carried out in vitro, to establish that the agent has the desired properties of decreasing IL-23R activity but not IL-12Rβ activity. The measure typically will be carried out in vitro, to establish that the agent has the desired property of not decreasing IL-12Rβ activity. As used herein "does not decrease" means IL-12Rβ activity will decrease significantly less than the decrease observed in IL-23 activity. that the IL-12Rβ activity levels do not decrease in a statistically significant manner, relative to a control. Typically, the IL-12Rβ activity does not decrease in a statistically significant manner, relative to a control. In general, the decrease in IL-12Rβ activity, relative to a control, would be less than 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, or 0.1%. Typically, there would be no statistically significant decrease in IL-12Rβ activity.

In some embodiments, the agent is administered to a subject and IL-12Rβ activity is not decreased relative to the level of IL-12Rβ activity prior to administration of the agent. In some embodiments, the IL-12Rβ activity is not decreased relative to the level of IL-12Rβ activity in the subject 30 minutes, 1 hour, 2 hours, 3 hours, 4 hours, 5 hours, 6 hours 12 hours 24 hours, 2 days, 3 days, 4 days, 5 days 6 days, 1 week, 2 weeks, 3 weeks, or 4 weeks or more prior to administration of the agent. In some embodiments, multiple doses of the agent are administered to a subject and IL-12Rβ activity is not decreased relative to the level of IL-12Rβ activity prior to the first administration of the agent, e.g., the beginning of treatment. In some embodiments, the IL-12Rβ activity is not decreased relative to the level of IL-12Rβ activity in the subject 30 minutes, 1 hour, 2 hours, 3 hours, 4 hours, 5 hours, 6 hours 12 hours 24 hours, 2 days, 3 days, 4 days, 5 days 6 days, 1 week, 2 weeks, 3 weeks, or 4 weeks or more prior to the first administration of the agent. In some embodiments, multiple doses of the agent are administered to a subject and IL-12Rβ activity is not decreased relative to the level of IL-12Rβ activity prior to the current administration of the agent. In some embodiments, the IL-12Rβ activity is not decreased relative to the level of IL-12Rβ activity in the subject 30 minutes, 1 hour, 2 hours, 3 hours, 4 hours, 5 hours, 6 hours 12 hours, 24 hours, 2 days, 3 days, 4 days, 5 days 6 days, 1 week, 2 weeks, 3 weeks, or 4 weeks or more prior to the current administration of the agent.

In some embodiments, the agent is administered to a subject and IL-12Rβ activity is not decreased relative to the level of IL-12Rβ activity in a control subject who is not treated with the agent. In some embodiments, the control subject has the same or a similar type of cancer as the subject. In some embodiments, the control subject has the same or a similar severity of cancer as the subject. In some embodiments, the control subject does not have cancer. In some embodiments, the control subject is the same or a similar age as the subject. In some embodiments, the control subject is the same sex as the subject. In some embodiments, the control subject is related to the subject. In some embodiments, the control subject is a twin of the subject.

In some embodiments, the agent is administered to a Treg cell in vitro and IL-12Rβ activity is not decreased relative a cell of the same clonal population, e.g., of the same culture, that are not administered the agent. In some embodiments, the IL-12Rβ activity of the cell of the same clonal population is measured simultaneously or near simultaneously with the IL-12Rβ activity of the Treg cell. In some embodiments, the IL-12Rβ activity of the cell of the same clonal population is measured before or after the IL-12Rβ activity of the Treg cell. In some embodiments, the agent is administered to a Treg in vitro and IL-12Rβ activity is not decreased relative to cells of the same cell type, e.g., are derived from the same source, that are not administered the agent.

In some embodiments, IL-12Rβ activity comprises STAT4 phosphorylation. In some embodiments, STAT4 phosphorylation levels do not decrease by more than 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, or 0.1%.

In some embodiments, IL-12Rβ activity comprises a change in expression of IL-12Rβ2, IL18-Rβ1, IRF1, IL-2R, and/or G6NT. In some embodiments, expression of IL-12Rβ2, IL18-Rβ1, IRF1, IL-2R, and/or G6NT do not decrease by more than 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, or 0.1%.

In some embodiments, IL12 activity can be measured by measuring IL-17 and/or interferon-gamma secretion following treatment of activated peripheral blood mononuclear cells (Dallas et al., Drug Metabolism and Disposition, 2013, 41:689-693). In some embodiments, IL-23 activity can be measured by measuring differentiation of CD4+ T cells to interferon-gamma (IFN-gamma)-producing T helper 1 (Th1) cells. (Reddy et al., Cell Immunol, 2007, 47:1-11.)

Induction of Treg Differentiation

In some embodiments, the agents described herein are useful in a method of inducing differentiation of cells. In some embodiments, an agent described herein induces differentiation of a T cell. In some embodiments, an agent described herein induces differentiation of a regulatory T cell (i.e., a Treg). In some embodiments, an agent described herein induces differentiation of a Treg cell to a Teff cell.

In some embodiments, Treg cells are Helios+ Treg cells. In some embodiments, Treg cells are TIGIT+ Treg cells. In some embodiments, Treg cells are CD4$^+$ Treg cells. In some embodiments, the CD4+ Treg cells are CD4+CD25+ Treg cells. CD4+CD25+ regulatory T cells are thought to function as a regulator of autoimmunity by suppressing the proliferation and/or cytokine production of CD4+CD25− T cell responder cells at the site of inflammation. In some embodiments, the CD4+ Treg cells are CD4+FoxP3+ Treg cells. In some embodiments, the CD4+ Treg cells are CD4+FoxP3+ CD25+ Treg cells.

In some embodiments, Treg cells are CD8$^+$ Treg cells. In some embodiments, the CD8$^+$ Treg cells are CD8+CD28− Treg cells. In some embodiments, the CD8+ Treg is positive for Killer cell immunoglobulin like receptor (Kir+).

In some embodiments, Treg cells are Tr1 Treg cells. In some embodiments, Treg cells are Th3 Treg cells. In some embodiments, Treg cells are Qa-1 restricted Treg cells.

In some embodiments, Teff cells are marked by the expression of certain cytokines. Examples of effector cytokines expressed by Teff include tumor necrosis factor alpha (TNF-α), interferon-γ (IFN-γ), interleukin-17 (IL-17), interleukin-2 (IL-2), and Granzyme B. However, the skilled artisan appreciates that other effector cytokines may also be expressed by differentiated T effector cells.

In some embodiments, effector cells are CD4$^+$ effector T cells. As used herein the term "CD4 effector T cells" refers to a subset of T cells which are associated with cell-mediated immune response. They are characterized by the secretion of one or more effector cytokines such as, but not limited to, IFN-γ, TNF-α, IL-17, IL-2 and granzyme B.

In some embodiments, the effector cells are CD8$^+$ effector T cells. In some embodiments, CD8$^+$ effector T cells are cytotoxic T cells.

In some embodiments, when differentiation is induced, 0.01%-100% of the Treg, e.g., intratumoral Treg, are converted to Teff. In some embodiments, when differentiation is induced, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the Treg, e.g., intratumoral Treg, are converted to Teff. In some embodiments, when differentiation is induced, more than 0.01%, 0.05%, 0.1%, 0.5%, 1%, 5%, 10%, or 20% of the Treg, e.g., intratumoral Treg, are converted to Teff. In some embodiments, when differentiation is induced, 0.01%-1%, 0.1%-1%, 0.5%-2%, 1%-10%, 2%-15%, 5%-20%, 10%-30%, 20%-50%, 20%-70%, 40%-50%, 40%-60%, 50%-70%, 50%-80%, 60%-70%, 60%-90%, 70%-90%, 70%-99%, or 80%-99% of the Treg, e.g., intratumoral Treg, are converted to Teff.

In some embodiments, when differentiation is induced, 0.01%-100% of CD4+CD25+ cells, e.g., intratumoral CD4+CD25+ cells, are converted to CD8+ cells. In some embodiments, when differentiation is induced, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of CD4+CD25+ cells, e.g., intratumoral CD4+CD25+ cells, are converted to CD8+ cells. In some embodiments, when differentiation is induced, more than 0.01%, 0.05%, 0.1%, 0.5%, 1%, 5%, 10%, or 20% of CD4+CD25+ cells, e.g., intratumoral CD4+CD25+ cells, are converted to CD8+ cells. In some embodiments, when differentiation is induced, 0.01%-1%, 0.1%-1%, 0.5%-2%, 1%-10%, 2%-15%, 5%-20%, 10%-30%, 20%-50%, 20%-70%, 40%-50%, 40%-60%, 50%-70%, 50%-80%, 60%-70%, 60%-90%, 70%-90%, 70%-99%, or 80%-99% of CD4+CD25+ cells, e.g., intratumoral CD4+CD25+ cells, are converted to CD8+ cells.

In some embodiments, when differentiation is induced, 0.01%-100% of CD4+CD25+ cells, e.g., intratumoral CD4+CD25+ cells, are converted to cells that secrete one or more of IFN-γ, TNF-α, IL-17, IL-2 and granzyme B. In some embodiments, when differentiation is induced, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of CD4+CD25+ cells, e.g., intratumoral CD4+CD25+ cells, are converted to cells that secrete one or more of IFN-γ, TNF-α, IL-17, IL-2 and granzyme B. In some embodiments, when differentiation is induced, more than 0.01%, 0.05%, 0.1%, 0.5%, 1%, 5%, 10%, or 20% of CD4+CD25+ cells, e.g., intratumoral CD4+CD25+ cells, are converted to cells that secrete one or more of IFN-γ, TNF-α, IL-17, IL-2 and granzyme B. In some embodiments, when differentiation is induced, 0.01%-1%, 0.1%-1%, 0.5%-2%, 1%-10%, 2%-15%, 5%-20%, 10%-30%, 20%-50%, 20%-70%, 40%-50%, 40%-60%, 50%-

70%, 50%-80%, 60%-70%, 60%-90%, 70%-90%, 70%-99%, or 80%-99% of CD4+CD25+ cells, e.g., intratumoral CD4+CD25+ cells, are converted to cells that secrete one or more of IFN-γ, TNF-α, IL-17, IL-2 and granzyme B.

In some embodiments, the phenotype of the cells is determined using any method known in the art, for example, flow cytometry.

In some embodiments, the cells are differentiated in vitro. In some embodiments, In some embodiments, one or more parameters identified herein, e.g., IL-23R or IL-12Rβ activity, stat3 phosphorylation, expression of one or more targets of IL-23R and/or IL-12Rβ, and/or conversion of Treg to Teff, are measured in the in vitro cells.

Agents

The methods described herein contemplate treating cancer with agents that decrease IL-23R activity and do not decrease IL-12Rβ activity.

Examples of inhibitor agents that may be used in accordance with the present disclosure include, without limitation, nucleic acids (e.g., DNA and/or RNA) and nucleic acid analogues; antibodies, including full-length antibodies and antigen-binding antibody fragments, polyclonal antibodies, monoclonal antibodies, chimeric antibodies, and humanized antibodies; proteins, including peptides, peptide-mimetics and aptamers; and small molecules.

In some embodiments, an agent described herein binds the extracellular domain of IL-23R.

Antibodies

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a target antigen, such as IL-23R. In some embodiments, the antibody disclosed herein specifically binds the extracellular domain of IL-23R. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an IL-23R epitope is an antibody that binds this IL-23R epitope with greater affinity, avidity, more readily, and/or with greater duration than it binds to other IL-23R epitopes or non-IL-23R epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of interfering with the IL-23R signaling pathway can be an antibody that binds an IL-23R (e.g., the extracellular domain of IL-23R) and inhibits IL-23R biological activity and/or downstream pathways mediated by IL-23R. Exemplary antibodies that bind IL-23R are shown in Table 1. In some embodiments, the antibodies shown in Table 1 bind the extracellular domain of IL-23R.

TABLE 1

Anti-IL23-R Antibodies

| Source | Catalog No. | Host Species | Species Reactivity | Clonality | Immunogen | Conjugated ? |
|---|---|---|---|---|---|---|
| Invitrogen | MA-24804 | Mouse | Human, mouse, non-human primate | Monoclonal | Amino acids 288-315 of human IL-23R | No |
| Invitrogen | MA5-23906 | Rat | Mouse | Monoclonal | Recombinant mouse IL-23 R Gly24-Asp372 | No |
| LifeSpan Biosciences | LS-C83986 | Goat | Human | Polyclonal | Amino acids 59-87 of human IL-23R | No |
| LifeSpan Biosciences | LS-C37068-100 | Mouse | Human | Monoclonal | NP_653302 | No |
| LifeSpan Biosciences | LS-C37069-100 | Mouse | Human | Monoclonal | Unknown | PE |
| LifeSpan Biosciences | LS-C125821-100 | Mouse | Human | Monoclonal | Unknown | PerCP |
| LifeSpan Biosciences | ABIN393707 | Mouse | Human | Monoclonal | Unknown | No |
| Aviva Systems Biology | OABF00713 | Rabbit | Human, mouse, rat | Polyclonal | KLH-conjugated synthetic peptide of human IL-23R | No |
| United States Biological | 223595 | Rabbit | Human | Polyclonal | Full-length human IL-23R | No |
| Abeomics | 10-4030 | Mouse | Human | Monoclonal | 250-450 of IL-23R | No |
| St. John's Laboratory | STJ24181 | Rabbit | Human, Mouse, Rat | Polyclonal | Recombinant peptide from human IL-23R | No |
| Biorbyt | Orb140302 | Rabbit | Human | Polyclonal | Amino acids 428-457 of human IL-23R | No |
| Biorbyt | Orb47095 | Rabbit | Human | Polyclonal | Full length human IL-23R | No |
| ProSci, Inc. | 58-876 | Rabbit | Human | Polyclonal | Amino acids 428-457 of human IL-23R | No |
| Atlas Antibodies | HPA056427 | Rabbit | Human | Polyclonal | Full length human IL-23R | No |
| MyBioSource | MBS854115 | Rabbit | Human | Polyclonal | Full length human IL-23R | No |
| MyBioSource | MBS9404638 | Rabbit | Human, Mouse, Rat | Polyclonal | Full length human IL-23R | No |
| ABclonal | A1613 | Rabbit | Human, Mouse, Rat | Polyclonal | Recombinant Human Protein | No |
| Invitrogen | MA5-23935 | Mouse | Human | Monoclonal | Mouse-myeloma cell line NS0-derived recombinant IL-23R amino acids 24-354 | No |

TABLE 1-continued

Anti-IL23-R Antibodies

| Source | Catalog No. | Host Species | Species Reactivity | Clonality | Immunogen | Conjugated ? |
|---|---|---|---|---|---|---|
| Invitrogen | MA5-23906 | Rat | Mouse | Monoclonal | Mouse-myeloma cell line NSO-derived recombinant IL-23R amino acids 24-372 | No |
| BioMatik | CAC07795 | Rabbit | Human, Mouse | Polyclonal | Human IL-23R amino acids 15-125 | No |
| BioMatik | CAU22706 | Rabbit | Rat | Polyclonal | IL-23R amino acids 25-355 | No |
| Origene Technologies | TA327101 | Rabbit | Human, Mouse, Rat | Polyclonal | Recombinant human IL-23R | No |
| Origene Technologies | TA321935 | Rabbit | Human, Mouse, Rat | Polyclonal | Human IL-23R amino acids 21-227 | No |
| LifeSpan Biosciences | LS-C403797 | Rabbit | Human | Polyclonal | Human IL-23R | No |
| LifeSpan Biosciences | LS-C192978 | Rabbit | Human, Mouse, Rat | Polyclonal | Human IL-23R | No |
| Abnova | PAB0224 | Rabbit | Human, Mouse | Polyclonal | Human IL-23R amino acids 400-470 | No |
| Abnova | H00149233 | Mouse | Human | Monoclonal | Human IL-23R amino acids 553-628 | No |
| NSJ Bioreagents | R32848 | Rabbit | Mouse, Rat | Polyclonal | Amino acids 25-233 | No |
| Antibodies Online | ABIN342781 | Goat | Human | Polyclonal | Human IL-23R amino acids 59-87 | No |
| Antibodies Online | ABIN221348 | Mouse | Human | Monoclonal | Human IL-23R amino acids 24-354 | PE (Phycoerythrin) |
| Antibodies Online | ABIN530970 | Mouse | Human | Monoclonal | LNQGECS SPD IQNSVEEE TT MLLENDS PSETIPEQ TLLPDEFV SCLGIVNE ELPSINTY F PQNILESH FN RISLLE | No |
| Antibodies Online | ABIN360919 | Mouse | Human | Monoclonal | Recombinant protein of IL-23R extracellular domain | No |
| Signalway Antibody | 31023 | Rabbit | Human | Polyclonal | Human IL-23R amino acids 31-227 | No |
| Signalway Antibody | 32341 | Rabbit | Human, Mouse, Rat | Polyclonal | Human IL-23R | No |
| United States Biological | 036998 | Rabbit | Human | Polyclonal | Human IL-23R amino acids 427-457 | No |
| United States Biological | 128452 | Mouse | Human | Monoclonal | 553-629 from human IL23R | No |
| United States Biological | 247572 | Mouse | Unknown | Monoclonal | NP_653302, 553aa-628aa | No |
| United States Biological | 247573 | Mouse | Unknown | Monoclonal | IL23R | No |
| Bioworld Technology | BS6809 | Rabbit | Human, Mouse, Rat | Polyclonal | Human IL-23R full-length protein | No |

TABLE 1-continued

Anti-IL23-R Antibodies

| Source | Catalog No. | Host Species | Species Reactivity | Clonality | Immunogen | Conjugated ? |
|---|---|---|---|---|---|---|
| Abbexa | Abx130103 | Rabbit | Rat | Polyclonal | IL-23R | No |
| Cloud Clone | MAE765Hu21 | Mouse | Human | Monoclonal | Human IL-23R | No |
| Cloud Clone | PAE765Hu21 | Rabbit | Human | Polyclonal | Human IL-23R | No |
| Enzo Life Sciences | ALX-210-636-C200 | Goat | Human, Mouse | Polyclonal | Human IL-23R amino acids 59-87 | No |
| Bio-Rad | VMA00297KT | Mouse | Human | Monoclonal | Human IL-23R | No |
| R&D Systems | FAB14001P | Mouse | Human | Monoclonal | Human IL-23R amino acids 24-354 | PE (Phycoerythrin) |
| R&D Systems | FAB14001A | Mouse | Human | Monoclonal | Human IL-23R amino acids 24-354 | Allophycocyanin |
| Bio-Rad | AHP1821 | Goat | Mouse, Human | Polyclonal | Human IL-23R N-terminus | No |
| Santa Cruz Biotechnology, Inc. | sc-293485 | Mouse | Human | Monoclonal | IL-23R | No |
| Bio-Rad | VMA00297K | Mouse | Human | Monoclonal | IL-23 R | No |
| Novus Biologicals | NB600-1147 | Rabbit | Human, Mouse | Polyclonal | Human IL-23R amino acids 439-455 | No |
| Novus Biologicals | NB2-47419 | Rabbit | Human | Polyclonal | Human IL-23R amino acids 258-346 | No |
| Novus Biologicals | NBP2-27091SS | Mouse | Human, Primate | Monoclonal | Amino acids 288-315 of hIL-23 receptor | No |
| Bioss | Bs-1460R | Rabbit | Human, Mouse, Rat | Polyclonal | Human IL-23R | No |
| BosterBio | A00607 | Rabbit | Mouse, Rat | Polyclonal | Mouse IL-23R amino acids 25-233 | No |
| Millipore Sigma | 06-1331 | Rabbit | Human, Mouse, Rat, Ox, Horse | Polyclonal | Human IL-23R | No |
| Sigma-Aldrich | WH01429233M1 | Mouse | Human | Monoclonal | Human IL-23R | No |
| Creative Biolabs | TAB-421CL | Unknown | Human | Monoclonal | Human IL-23R | Unknown |
| Biolegend | Unknown: Clone 12B2B64 | Rat | Mouse | Monoclonal | Mouse IL-23R amino acids 24-374 | No |
| R&D | Unknown: Clone 258018 | Unknown | Mouse | Monoclonal | Unknown | Unknown |

In some embodiments, the antibody has one, two or all of a light chain CDR1, CDR2, and/or CDR3 and/or one, two or all of a heavy chain CDR1, CDR2 and/or CDR3. In some embodiments, the antibody has an amino acid sequence having one, two or all of a light chain CDR1, CDR2, and/or CDR3 and/or one, two or all of a heavy chain CDR1, CDR2 and/or CDR3 of an antibody in Table 1. In some embodiments, the antibody has an amino acid sequence having at least one, two or three modifications (e.g., substitutions, e.g., conservative substitutions) but not more than 30, 20 or 10 modifications (e.g., substitutions, e.g., conservative substitutions) to one, two or all of a light chain CDR1, CDR2, and/or CDR3 and/or one, two or all of a heavy chain CDR1, CDR2 and/or CDR3 of an antibody in Table 1.

In some embodiments, the antibody has one or both of a VH and VL. In some embodiments, the antibody has an amino acid sequence having one or both of a VH and VL of an antibody in Table 1, or a sequence with 95-99% identity thereof, e.g., 95%, 96%, 97%, 98% or 99% identity, e.g., 96-99%, 96-98%, 96-97%, 97-99%, 97-98% and 98-99% identity.

In some embodiments, the antibody binds IL-23R and does not bind IL-12Rβ. In some embodiments, the IL-12Rβ binding affinity of an anti-IL23R antibody measured. In some embodiments, the anti-IL23-R antibodies shown in Table 1 are screened to identify anti-IL23-R antibodies with low or no binding affinity for IL-12Rβ, e.g., has greater binding affinity for IL-23R than for IL-12Rβ. Binding affinity can be expressed KD or dissociation constant, and an increased binding affinity corresponds to a decreased KD. One way of determining binding affinity of antibodies to IL-23R is by measuring binding affinity of monofunctional Fab fragments of the antibody. To obtain monofunctional Fab fragments, an antibody (for example, IgG) can be cleaved with papain or expressed recombinantly. The affinity of an anti-IL-23R Fab fragment of an antibody can be determined by surface plasmon resonance (BIAcore3000™ surface plasmon resonance (SPR) system, BIAcore, INC, Piscaway N.J.). Kinetic association rates (kon) and dissociation rates (koff) (generally measured at 25° C.) are obtained; and equilibrium dissociation constant (KD) values are calculated as koff/kon. In some embodiments, an antibody described herein has 1, 2, 5, 10, 20, 50, 75, 100, 200, 300, 400, 500, 600, 700, 800, 900, 1,000, 2,000, 5,000, 10,000, 50,000, 100,000-fold or more greater binding affinity for IL-23R than for IL-12Rβ. In some embodiments, an antibody described herein has greater than 1, 2, 5, 10, 20, 50, 75, 100, 200, 300, 400, 500, 600, 700, 800, 900, 1,000, 2,000, 5,000, 10,000, 50,000, 100,000-fold more binding affinity for IL-23R than for IL-12Rβ.

Methods of producing antibodies (e.g., monoclonal antibodies or polyclonal antibodies) are known in the art. For example, a polyclonal antibody may be prepared by immunizing an animal, preferably a mammal, with an allergen of choice followed by the isolation of antibody-producing B-lymphocytes from blood, bone marrow, lymph nodes, or spleen. Alternatively, antibody-producing cells may be isolated from an animal and exposed to an allergen in vitro against which antibodies are to be raised. The antibody-producing cells may then be cultured to obtain a population of antibody-producing cells, optionally after fusion to an immortalized cell line such as a myeloma. In some embodiments, as a starting material B-lymphocytes may be isolated from the tissue of an allergic patient, in order to generate fully human polyclonal antibodies. Antibodies may be produced in mice, rats, pigs (swine), sheep, bovine material, or other animals transgenic for the human immunoglobulin genes, as starting material in order to generate fully human polyclonal antibodies. In some embodiments, mice or other animals transgenic for the human immunoglobulin genes (e.g. as disclosed in U.S. Pat. No. 5,939,598), the animals may be immunized to stimulate the in vivo generation of specific antibodies and antibody producing cells before preparation of the polyclonal antibodies from the animal by extraction of B lymphocytes or purification of polyclonal serum.

Monoclonal antibodies are typically made by cell culture that involves fusing myeloma cells with mouse spleen cells immunized with the desired antigen (i.e., hyrbidoma technology). The mixture of cells is diluted and clones are grown from single parent cells on microtitre wells. The antibodies secreted by the different clones are then assayed for their ability to bind to the antigen (with a test such as ELISA or Antigen Microarray Assay) or immuno-dot blot. The most productive and stable clone is then selected for future use.

In some embodiments, the antibodies described herein are "humanized" for use in human (e.g., as therapeutics). In some embodiments, an antibody shown in Table 1 is a murine antibody and the antibody is humanized. "Humanized" forms of non-human (e.g., rodent) antibodies are chimeric antibodies that contain minimal sequence derived from the non-human antibody. Humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Nucleic Acids

In some embodiments, the agent is a nucleic acid. In some embodiments, the agent binds a nucleic acid expressing IL-23R. e.g., having a sequence shown at NCBI Ref. No. NM_144701.2. In some embodiments, the agent binds a sequence encoding the extracellular domain of IL-23R.

As used herein, "gene silencing," refers to post-transcriptional gene silencing, which may be the result of mRNA of a particular gene being degraded or blocked. The RNAi inhibitor agents provide herein may, in some embodiments, decrease the expression level of IL-23R mRNA by at least about 5%, about 10%, about 20%, about 30%, about 40%, about 50%, about 55%, about 60%, about 70%, about 75%, about 80%, about 85%, about 90%, about 95%, about 99% or about 100% of the mRNA level found in the cell without the presence of an RNAi inhibitor agent.

As used herein, "RNA interference" is a biological process in which RNA molecules inhibit gene expression, typically by causing the degradation of specific mRNA molecules.

In some embodiments, the agent is an siRNA. As used herein, "siRNA" is a class of double-stranded RNA molecules, which interferes with the expression of specific genes having a nucleotide sequence complementary to the siRNA. siRNAs typically have a well-defined structure: a short (e.g., 21 base pair) double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs (shRNAs). An siRNA for use in accordance with the present disclosure may be about 15 to about 35 base pairs, or about 20 to about 25 base pairs, in length. In some embodiments, the siRNA may be about 15, 16, 17, 18, 19, 20, 21, 22, 23, 24, 25, 26, 27, 28, 29, 30, 31, 32, 33, 34 or 35 base pairs in length. In some embodiments, the siRNA is complementary to IL-23R, e.g., having a sequence shown at NCBI Ref. No. NM_144701.2. In some embodiments, the siRNA is complementary to a sequence encoding the extracellular domain of IL-23R.

Exemplary siRNAs against IL23-R are shown in Table 2. In some embodiments, the siRNA comprises a nucleic acid sequence of any one of SEQ ID NOs; 19-31. In some embodiments, the siRNA comprises a nucleic acid sequence having 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% to any one of SEQ ID NOs; 19-31. In some embodiments, the siRNA comprises a nucleic acid sequence having at least 5, e.g., 5, 6, 7, 8, 9, 10, 11, 12, 13, 14, 15, 16, 17, 18, 19, 20, or 21 consecutive nucleotides of a nucleic acid sequence of any one of SEQ ID NOs; 19-31, or a sequence having 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to a nucleic acid sequence having at least 5, e.g., 5, 6, 7, 8, 9, 10, 11, 12, 13, 14, 15, 16, 17, 18, 19, 20, or 21 consecutive nucleotides of a nucleic acid sequence of any one of SEQ ID NOs; 19-31.

TABLE 2 siRNAs against IL23-R generated using siRNA Wizard v3.1 at http://www.invivogen.com/sirnawizard/design.php

| Number | Sequence | Position | Length (bp) | SEQ ID NO: |
|---|---|---|---|---|
| 1 | GACCTGGAACGTGAAAGAATT | 27-48 | 21 | 19 |
| 2 | GCAAAGCGTTTCAGCATGATA | 209-230 | 21 | 20 |
| 3 | GATTCCGAAATGGCTGTATGA | 411-432 | 21 | 21 |
| 4 | GAAATGGCTGTATGAAGATAT | 417-438 | 21 | 22 |
| 5 | GCGAACTGATGAACAACAACA | 485-506 | 21 | 23 |
| 6 | GGTGTATATTCCGGATCTGAA | 660-681 | 21 | 24 |
| 7 | GGATCTGAACACCGGCTATAA | 672-693 | 21 | 25 |
| 8 | GCAGCCATCTGAGCAACAACA | 673-694 | 21 | 26 |
| 9 | GCAGCCATCTGAGCAACAACA | 722-743 | 21 | 27 |
| 10 | GCAACAACAACGAAATTACCA | 734-755 | 21 | 28 |
| 11 | GCGAACTGAGCCTGATTCTGA | 878-899 | 21 | 29 |
| 12 | GGGCATTGTGAACGAAGAACT | 1032-1053 | 21 | 30 |
| 13 | GCCGAGCATTAACACCTATTT | 1053-1074 | 21 | 31 |

In some embodiments, the agent is an shRNA. As used herein, "shRNA" refers to a sequence of RNA that makes a tight hairpin turn that can be used to silence target gene expression through RNA interference (RNAi). Expression of shRNA in cells may be accomplished by delivery of plasmids or through viral or bacterial vectors. For example, in some embodiments, shRNA targeting IL-23R may be delivered to Treg cells by transfecting the cells with a plasmid that contains a nucleic acid encoding the shRNA. In some embodiments, bacterial vectors may be used to obtain shRNA expression in cells. In some embodiments, viral vectors (e.g., adeno-associated viruses (AAVs), adenoviruses, and lentiviruses) may be used to obtain shRNA expression in cells. Due to the ability of shRNA to provide specific, long-lasting, gene silencing, shRNA may be used for gene therapy applications. In some embodiments, the shRNA is complementary to IL-23R, e.g., having a sequence shown at NCBI Ref. No. NM_144701.2. In some embodiments, the shRNA is complementary to a sequence encoding the extracellular domain of IL-23R.

As used herein, a "stem-loop structure" refers to a nucleic acid having a secondary structure that includes a region of nucleotides which are known or predicted to form a double strand (stem portion) that is linked on one side by a region of predominantly single-stranded nucleotides (loop portion). The term "hairpin" may be used herein to refer to a stem-loop structure.

Peptides

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

A peptide that is "derived from" a protein (e.g., a peptide derived from IL-23R) means the peptide is obtained from the protein and has an amino acid sequence that shares homology with the fragment of the protein it corresponds to. The amino acid sequence of the peptide may be at least 70%, at least 75%, at least 80%, at least 85%, at least 90%, at least 95%, at least 99% or 100% identical to the amino acid sequence of the fragment of the protein it corresponds to. A peptide that is derived from a protein may also contain chemical modifications, amino acid substitutions, and/or unnatural amino acids.

Useful peptides ing to the invention include antibodies, zinc finger proteins which can target and cleave DNA, and protein antagonists which mimic the structure of the native ligand for a receptor and block binding of the native ligand without agonizing the receptor.

Small Molecules

In other embodiments, the IL-23R inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the agent according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

In Vitro Differentiation

In some embodiments, cells, e.g., Treg cells, are contacted in vitro with an agent described herein and IL-23R activity is decreased. In some embodiments, differentiation is induced.

In some embodiments, the cells, e.g., Treg cells, are isolated. In some embodiments, the cells are isolated from mice. In some embodiments, the cells are isolated from murine spleens. In some embodiments, the cells are isolated from murine lymph nodes. In some embodiments, the cells, e.g., Treg cells, are isolated from a human subject. In some embodiments, the cells are isolated from peripheral blood mononuclear cells.

In some embodiments, the cells, e.g., Treg cells, are contacted in a buffer, e.g., PBS. In some embodiments, the Treg cells are contacted in a cell culture media, e.g., a hematopietic cell culture medium (e.g., X-VIVO®15) or a T cell expansion media (e.g., CTS OpTmizer T Cell Expansion SFM®).

In some embodiments, the cells, e.g., Treg cells, are contacted in the presence of anti-CD3 antibodies. In some embodiments, the cells, e.g., Treg cells are contacted in the presence of anti-CD28 antibodies. In some embodiments, the cells, e.g., Treg cells are contacted in the presence of anti-CD3 antibodies and anti-CD28 antibodies. In some embodiments, the anti-CD3 antibodies and/or anti-CD28 antibodies are attached to a surface. In some embodiments, the anti-CD3 antibodies and/or anti-CD28 antibodies are attached to a plate. In some embodiments, the anti-CD3 antibodies and/or anti-CD28 antibodies are attached to a bead.

In some embodiments, the cells, e.g., Treg cells, are contacted in the presence of one or more inflammatory cytokines. Inflammatory cytokines include, for example, interleukin-1 (IL-1), tumor necrosis factor (TNF), gamma-interferon (IFN-gamma), IL-12, IL-18, granulocyte-macrophage colony stimulating factor, IL-2, IL-4, IL-10, IL-13, IFN-alpha and TGF-β.

In some embodiments, the cells, e.g., Treg cells, are contacted in the presence of IL-2. In some embodiments, T reg cells are contacted in 0-1000 ng, 0-500 ng, 0-200 ng, 0-100 ng, or 0-50 ng IL-2. In some embodiments, the cells, e.g., Treg cells, are contacted in the presence of IL-4. In some embodiments, the T reg cells are contacted in 0-1000 ng, 0-500 ng, 0-200 ng, 0-100 ng, 0-50 ng, or 0-20 ng IL-4.

Therapeutic Uses

In some embodiments, provided herein are methods for treating cancer by administering an agent described herein.

The subject to be treated by the methods described herein are human.

A human subject who needs the treatment may be a human patient having, at risk for, or suspected of having cancer. A subject having cancer can be identified by routine medical examination, e.g., laboratory tests, functional tests, biopsy, CT scans, or ultrasounds. A subject suspected of having cancer might show one or more symptoms of the disorder. A subject at risk for cancer can be a subject having one or more of the risk factors for that disorder. For example, risk factors associated with cancer include (a) hereditary cancer, (b) age, and (c) family history of cancer.

Cancers include but are not limited to: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell lung cancer (NSCLC), small cell lung cancer, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), rectal, colon, colon-rectum, colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), head and neck cancer, meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertolI-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of cancer. Alternatively, sustained continuous release formulations of agent that decreases IL-23R activity may be appropriate. Various formulations and devices for achieving sustained release are known in the art.

In one example, dosages for an agent that decreases IL-23R activity as described herein may be determined empirically in individuals who have been given one or more administration(s) of the agent. Individuals are given incremental dosages of the agent. To assess efficacy of the agent, an indicator of IL-23R activity can be followed.

For the purpose of the present disclosure, the appropriate dosage of an agent that decreases IL-23R activity will depend on the specific agents (or compositions thereof) employed, the type and severity of cancer, whether the agent is administered for preventive or therapeutic purposes, previous therapy, the patient's clinical history and response to the agent, and the discretion of the attending physician.

As used herein, the term "treating" refers to the application or administration of a composition including one or more active agents to a subject, who has cancer, a symptom of cancer, or a predisposition toward the disease, with the purpose to cure, heal, alleviate, relieve, alter, remedy, ameliorate, improve, or affect the disorder, the symptom of the disease, or the predisposition toward the disease.

Alleviating cancer includes delaying the development or progression of the disease, or reducing disease severity. Alleviating the disease does not necessarily require curative results. As used therein, "delaying" the development of a disease (such as cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

Conventional methods, known to those of ordinary skill in the art of medicine, can be used to administer the agent to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Combination Therapies

In some embodiments, the methods described herein comprise administering an agent described herein in in conjunction with an additional therapy. In some embodiments, the additional therapy is an immunomodulatory agent. In some embodiments, the additional therapy is an agent that inhibits cancer cell growth.

Immunomodulators

In any of the foregoing aspects and following embodiments, the one or more immune checkpoint inhibitors are, for example, each an antagonist of programmed death 1 (PD-1), programmed death ligand 1 (PD-L1), cytotoxic T-lymphocyte-associated antigen 4 (CTLA-4), V-domain Ig suppressor of T cell activation (VISTA), programmed death ligand 2 (PD-L2), indoleamine 2,3-dioxygenase (IDO), arginase, B7 family inhibitory ligand B7-H3, B7 family inhibitory ligand B7-H4, lymphocyte activation gene 3 (LAG3), 2B4, B and T lymphocyte attenuator (BTLA), T cell membrane protein 3 (TIM3; also known as HAVcr2), adenosine A2a receptor (A2aR), a killer inhibitory receptor, and/or signal transducer and activator of transcription (STAT)3. In particular embodiments, the one or more immune checkpoint inhibitors are each an antagonist of programmed death 1 (PD-1), an antagonist of programmed death ligand 1 (PD-L1), an antagonist of cytotoxic T-lymphocyte-associated antigen 4 (CTLA-4), and/or an antagonist of V-domain Ig suppressor of T cell activation (VISTA).

In any of the foregoing aspects and embodiments, the PD-1 antagonist is, for example, an agent that binds to and antagonizes PD-1. Such agents can be, for example, a peptide that binds PD-1. Such agents can be a humanized antibody that selectively binds PD-1. In some embodiments, the humanized antibody that selectively binds PD-1 is nivolumab, pembrolizumab, pidilizumab, MEDI-0680, REGN2810, or AMP-224. In some embodiments, the humanized antibody that selectively binds PD-1 is nivolumab, pembrolizumab, or pidilizumab. In some embodiments, the antagonist is (i) an antisense molecule directed against PD-1 nucleic acid, (ii) an adnectin directed against PD-1 nucleic acid, (iii) a single stranded or double stranded RNAi inhibitor of PD-1, and/or (iv) a small molecule inhibitor of PD-1.

In any of the foregoing aspects and embodiments, the PD-L1 antagonist is, for example, an agent that binds to and antagonizes PD-L1. Such agents can be, for example, a peptide that binds PD-L1. Such agents can be a humanized antibody that selectively binds PD-L1. In some embodiments, the humanized antibody that selectively binds PD-L1 is BMS-936559/MDX-1105, MPDL3280A/RG7446/atezolizumab, MSB0010718C/avelumab, or MEDI4736/durvalumab. In some embodiments, the antagonist is (i) an antisense molecule directed against PD-L1, (ii) an adnectin directed against PD-L1, (iii) a single stranded or double stranded RNAi inhibitor of PD-L1, or (iv) a small molecule inhibitor of PD-L1. 10 In any of the foregoing aspects and embodiments, the CTLA-4 antagonist is, for example, an agent that binds to and antagonizes CTLA-4. Such agents can be, for example, a peptide that binds CTLA-4. Such agents can be a humanized antibody that selectively binds CTLA-4. In some embodiments, the humanized antibody that selectively binds CTLA-4 is ipilimumab or tremelimumab. In some embodiments, the CTLA-4 antagonist is (i) an antisense molecule directed against CD80, CD86, and/or CTLA-4 nucleic acid, (ii) an adnectin directed against CD80, CD86, and/or CTLA-4 nucleic acid, (iii) a single stranded or double stranded RNAi inhibitor of CD80, CD86, and/or CTLA-4, or (iv) a small molecule inhibitor of CD80, CD86, or CTLA-4.

In any of the foregoing aspects and embodiments, the VISTA antagonist is, for example, an agent that binds to and antagonizes VISTA. Such agents can be, for example, a peptide. Such agents can be an inhibitory antibody directed to VISTA. In some embodiments, the agent that binds to and antagonizes VISTA is a humanized antibody. In some embodiments, the agent that binds to and antagonizes VISTA is (i) an antisense molecule directed against VISTA nucleic acid, (ii) an adnectin directed against VISTA nucleic acid, (iii) a single stranded or double stranded RNAi inhibitor of VISTA, or (iv) a small molecule inhibitor of VISTA.

Chemotherapeutic Agents

In some embodiments, the methods described herein comprise administering an agent described herein in in conjunction with an agent that inhibits cancer cell growth.

In some embodiments, an agent that inhibits cancer cell growth comprises a chemotherapeutic agent. Chemotherapeutic agents include, for example, including alkylating agents, anthracyclines, cytoskeletal disruptors (Taxanes), epothilones, histone deacetylase inhibitors, inhibitors of topoisomerase I, inhibitors of topoisomerase II, kinase inhibitors, nucleotide analogs and precursor analogs, peptide antibiotics, platinum-based agents, retinoids, vinca alkaloids and derivatives thereof. Non-limiting examples include: (i) anti-angiogenic agents (e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000)); (ii) a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof; and (iii) chemotherapeutic compounds such as, e.g., pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones, and navelbine, epidipodophyllotoxins (etoposide and teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycin, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, mitoxantrone, topotecan, and irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

In some embodiments, an agent that inhibits cancer cell growth comprises external radiation therapy and internal radiation therapy (also called brachytherapy). Energy sources for external radiation therapy include x-rays, gamma rays and particle beams, energy sources used in internal radiation include radioactive iodine (iodine125 or iodine131), strontium89, or radioisotopes of phosphorous, palladium, cesium, indium, phosphate, or cobalt. Methods of administering radiation therapy are well known to those of skill in the art.

In some embodiments, an agent that inhibits cancer cell growth comprises a CD-44 antagonist. In some embodiments, the CD-44 antagonist is hyaluronic acid. In some embodiments, the CD-44 antagonist is an anti-CD-44 antibody.

In some embodiments, an agent that inhibits cancer cell growth comprises a CD133 antagonist.

In some embodiments, the methods described herein comprise administering an agent described herein in in conjunction with an agent that is an antagonist of inhibitory macrophages and/or dendritic cells.

Screening Methods

In some embodiments, the methods described herein provide for identifying a test compound that will convert a Treg into a Teff. The method comprises:

contacting a regulatory T cell (Treg) with a test compound;

measuring IL-23R activity in the cell;

measuring IL-12Rβ activity in the cell;

wherein the test compound is a compound for converting a regulatory T cell (Treg cell) into an effector cell if
(i) the IL-23R activity is decreased relative to a control cell that has been treated with a compound known to not decrease IL-23R activity and IL-12Rβ activity; and
(ii) the IL-12Rβ activity is not decreased relative to the control cell.

In some embodiments, contacting a regulatory T cell (Treg) with a test compound comprises contacting a regulatory T cell (Treg) with a test compound in vitro using the methods for in vitro differentiation described herein.

In some embodiments, IL-23R activity in the cell is measured. In some embodiments, measuring IL-23R activity comprises measuring expression of FoxP3, Helios, IL-17A, IL-17F, ROR-gamma, and/or IL-23. In some embodiments, measuring IL-23R activity comprises measuring expression of interferon-gamma. In some embodiments, measuring IL-23R activity comprises measuring STAT3 phosphorylation.

In some embodiments, a decrease in IL-23R activity comprises a decreased in IL-23R activity relative to a control as described supra. In some embodiments, a decrease in IL-23R activity comprises a decrease in expression of FoxP3, Helios, IL-17A, IL-17F, ROR-gamma, and/or IL-23, as is described supra.

In some embodiments, IL-12Rβ activity in the cell is measured. In some embodiments, measuring IL-12Rβ activity comprises measuring expression of interferon-gamma.

In some embodiments, IL-12Rβ activity does not decrease if IL-12Rβ activity does not decrease relative to a control as described supra. In some embodiments, IL-12Rβ activity does not decrease if IL-12Rβ2, IL18-Rβ1, IRF1, IL-2R, and/or G6NT expression does not decrease as described supra.

In some embodiments, the test compound is a polypeptide, a nucleic acid, or a small molecule, as is described herein.

In some embodiments, effector cytokines produced by the cell are measured. Effector cytokines include, but are not limited to TNF-α, IFN-γ, IL-17, IL-10, or IL-2.

EXAMPLES

Example 1: IL-23R as a Target in T Regulatory (Treg) Conversion and Anti-Tumor Therapy Immunological approaches to the treatment of cancer have shown great promise for increased long-term survival for a number of cancers and complete remission in others. The number of clinical trials using immunotherapy alone or in combination with conventional cancer treatments has grown remarkably, based on increased understanding of the critical contribution of T cell subsets to the control of cancer growth.

Regulatory T cells are critically important for maintenance of a balanced immune system, in part because they help to dampen excessive immune responses and prevent autoimmunity. However, immune suppression exerted by Treg can impede anti-tumor immune responses and promote cancer growth. The efficacy of several successful immunotherapies has been associated with depletion or blockade of CD4 regulatory T-cells (Treg) (Mahoney et al., Nat Rev Drug Discov 14:561-584). Described in this example is a more advanced strategy that depends on selective induction of Treg phenotypic instability and effector cell conversion of intratumoral but not systemic Treg.

Impact of Helios Regulated STAT5 Activation on nTreg Stability

It was previously determined that the Helios transcription factor (TF) maintains stable expression of FoxP3 under inflammatory conditions via regulation of STAT5b (Mahoney et al., Nat Rev Drug Discov 14:561-584). However the precise mechanism of Helios-dependent Treg stability and function has not yet been fully clarified. The data provided below defines the molecular basis of Helios-mediated stability and the biological activity of conventional Treg in the tumor microenvironment (TME).

Helios was recently defined as a critical transcriptional factor that ensures stable expression of the Treg phenotype, which shows that inhibition of Helios expression in intratumoral CD4+ Treg induces reprogramming of Treg into T-effector cells that can destroy tumor cells (Nakagawa et al., Proc Natl Acad Sci USA 113:6248-6253, Kim et al., Science 350:334-339). The response is marked by decreased numbers of intratumoral CD4 Treg, increased conversion of intratumoral Treg to T effector cells and increased production of effector cytokines by CD8 T cells. Since Treg conversion is restricted to intratumoral CD4 Treg, potential systemic toxicity and IRAEs may be avoided.

Figure 1B:
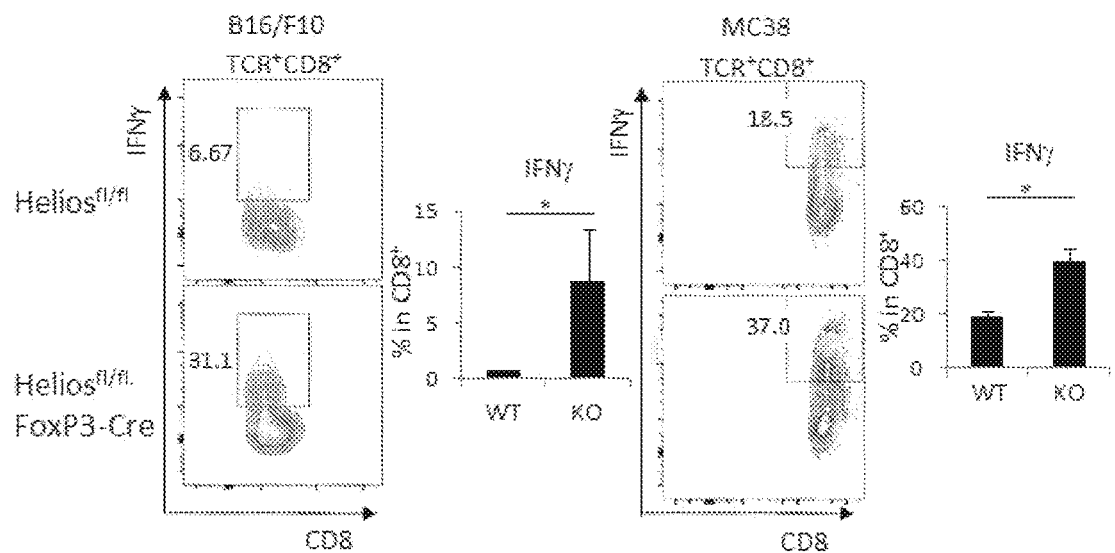

It has recently been shown that Helios$^{-/-}$ nTreg exhibit reduced expression of T cell anergy markers CD73 and FR4 which correlated with increased proinflammatory cytokine expression under inflammatory conditions (Kim et al., Science 350:334-339). Using Helios$^{-/-}$ mice with solid tumors (B16/F10 melanoma and MC38 colorectal cancer) as a source of inflammation, nTreg anergic phenotype was characterized (FIGS. 1A and 1B). nTreg loss of function was highlighted by reduced tumor size (FIG. 1A) and increased cytotoxic T cell activity (FIG. 1B).

Figure 2A:
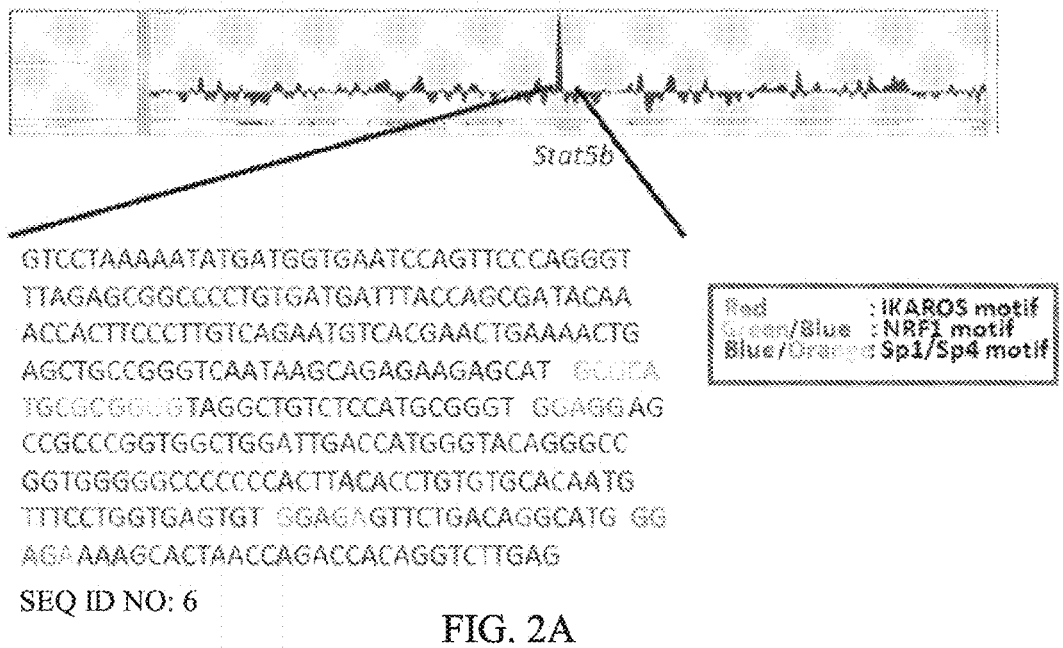
FIGS. 2A-2B. show Helios binding motifs in the first intron of STAT5b using ChiP-Seq analysis of Helios binding and modified histones at STAT5b in CD4 nTregs. The start sites of each gene locus are indicated. The vertical lines in the gene diagrams (bottom) indicate exons.
Figure 2B:
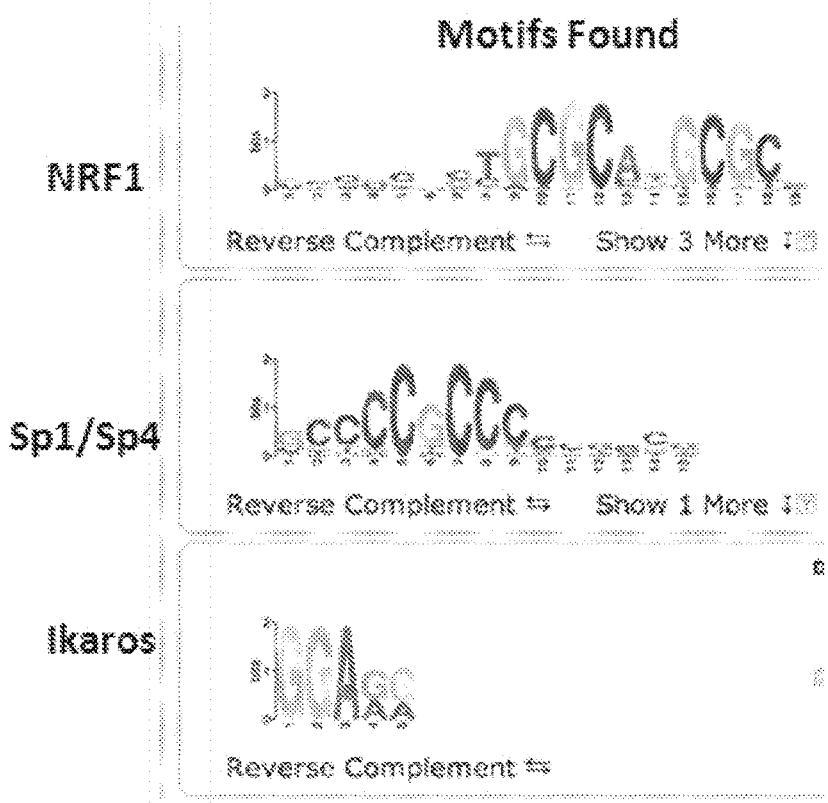

Chromatin immunoprecipitation DNA sequencing (ChIP-seq) analysis of Treg cells indicated that the STAT5b locus contains multiple Helios binding regions including a prominent Helios binding region located within the 5' enhancer intron of STAT5b (illustrated in FIGS. 2A-B). It is possible that Helios-dependent STAT5b interaction enhances Stat5b expression and stabilizes the nTreg phenotype via binding to the FoxP3 conserved noncoding sequence 2 (CNS2) region. CRISPR/Cas9 genome editing can be used to delete the putative Helios binding sites on STAT5b and generate genetically modified mice in which the interaction between Helios and Stat5b is interrupted.

Immunological Activity of Converted Th1-Like Cells

Figure 3A:
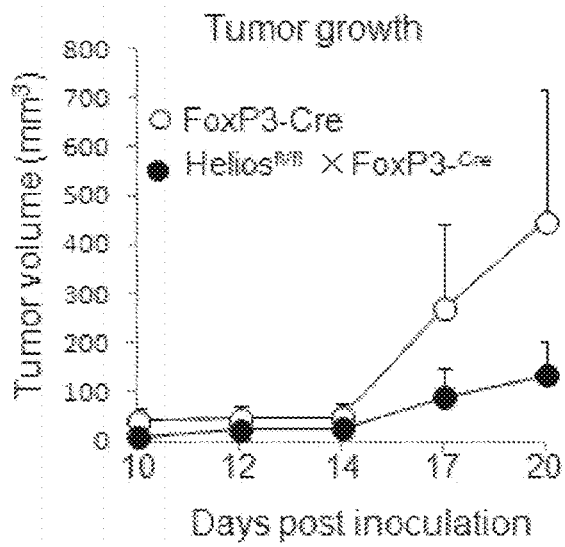
FIGS. 3A-3C show isolated function of Helios deficient CD4 Treg in antitumor immunity. nTregs were isolated from Rag2$^{-/-}$ mice (2×10$^6$ CD4: 1×10$^6$ CD8: 0.5×10$^6$ Helios$^{WT}$ or Helios$^{KO}$ nTreg) B16/F10 tumor. Flow cytometry was gated on CD45.2$^+$FoxP3$^+$ cells.
Figure 3B:
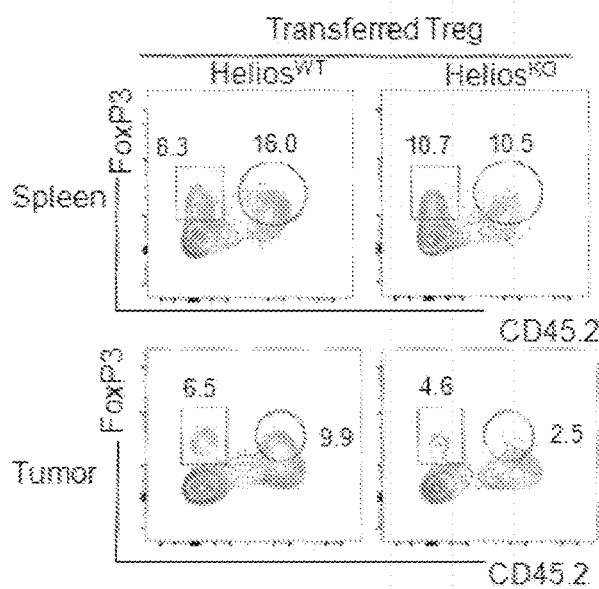
Figure 3C:
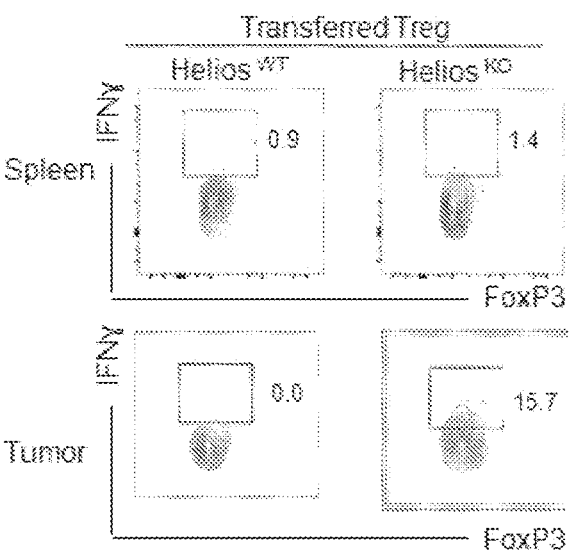

Selective deletion of Helios in FoxP3$^+$ Treg was found to result in decreased Treg-dependent inhibition of an anti-tumor response in B16/F10 inoculated Rag2$^{-/-}$ reconstituted mice (2×10$^6$ CD4: 1×10$^6$ CD8: 0.5×10$^6$ Helios$^{WT}$ or Helios$^{KO}$ nTreg) (FIG. 3A) which correlated with reduced FoxP3 expression (FIG. 3B) and increased production of the pro-inflammatory cytokine IFN-γ (FIG. 3C). Interestingly, the reduced FoxP3 expression and increased IFN-γ production by Rag2$^{-/-}$Helios$^{fl/fl}$FoxP3$^{Cre}$ mice was only noted in the tumor infiltrate (FIGS. 3B-3C). No significant changes were observed in spleen.

Figure 4A:
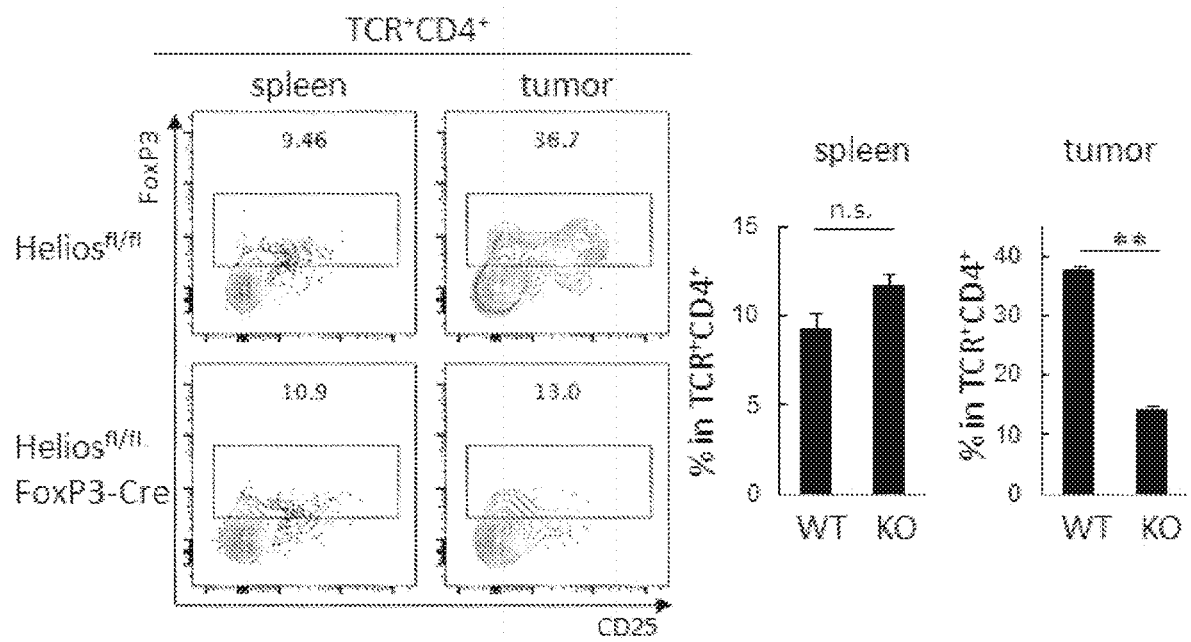
FIGS. 4A-4B show that Treg specific Helios$^{KO}$ mice present a reduced anergic phenotype. Anergic phenotype was determined in Treg specific Helios$^{WT}$ and Helios$^{KO}$ spleen and tumor infiltrate (MC38 inoculated mice) using co-expression of surface markers CD73 and FR4 in FoxP3$^+$ Treg.
Figure 4B:
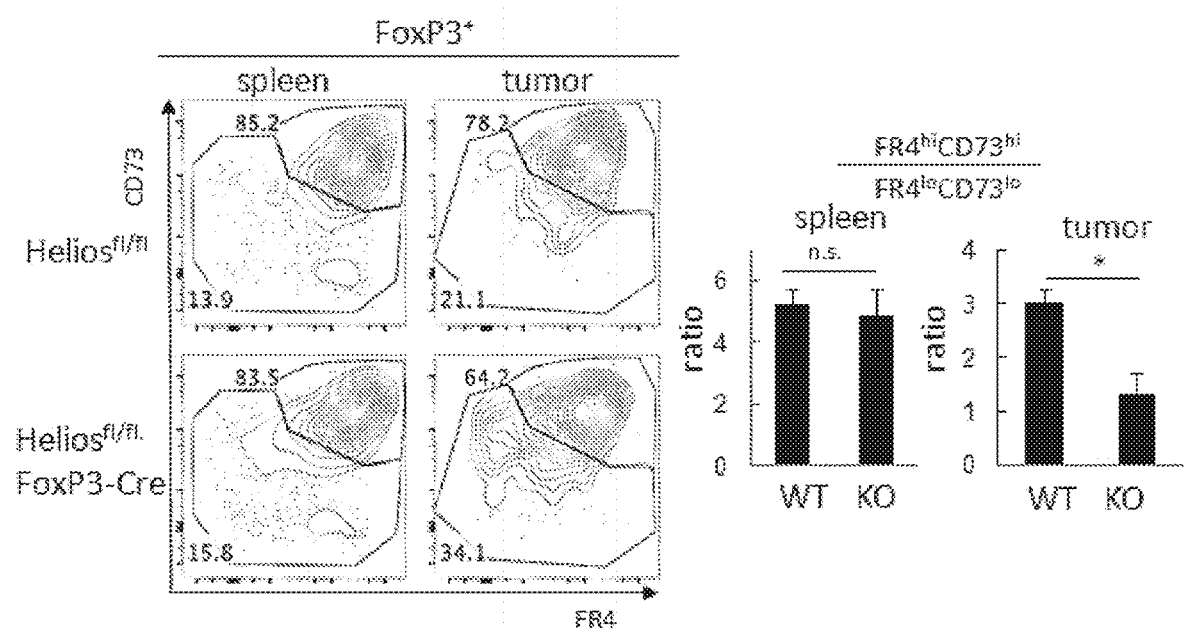
Figure 5A:
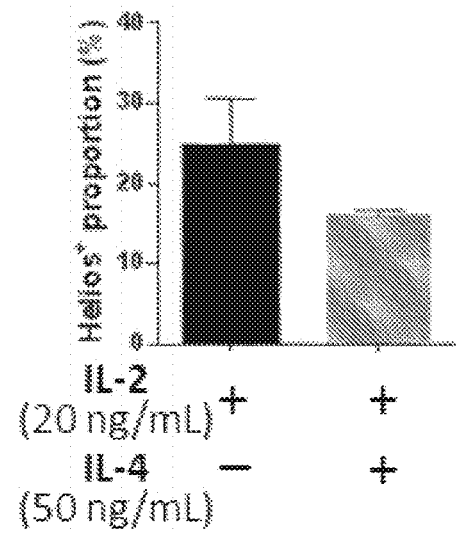
FIGS. 5A-5B show that Helios$^+$ nTreg lose surface receptor expression co-cultured with IL-4. nTreg were co-cultured with anti-CD3/anti-CD28 coated beads as well as steady state cytokine IL-2 and inflammatory cytokine IL-4.
Figure 5B:
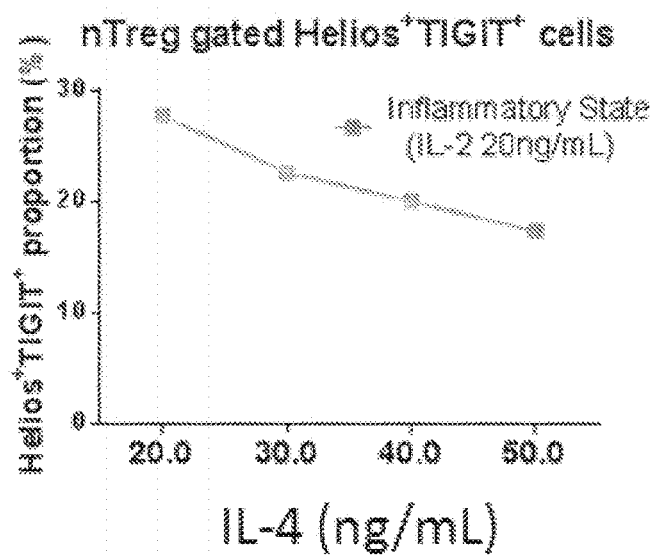

Helios deletion was also found to specifically destabilize Tregs in a second tumor model (MC38 colorectal cancer cell line) within the tumor microenvironment (FIGS. 4A and 4B). Loss of the Treg-mediated suppressive function (FIG. 4) resulted in decreased FoxP3 expression (FIG. 4A) as well as anergy markers CD73 and FR4 (FIG. 4B) suggesting that nTreg stability in solid tumors is Helios dependent. Furthermore, TCR activation of nTreg under inflammatory conditions (anti-CD3, anti-CD28, IL-2, IL-4) was found to reduce the proportion of nTreg cells positive for Helios and the surface receptor TIGIT (FIGS. 5A and 5B). Helios$^+$ nTreg cells were decreased by nearly 50% (FIG. 5A) when co-cultured with IL-4 and Helios$^+$ TIGIT$^+$ cells by ~50% (FIG. 5B) with increased IL-4 levels.

Antibodies that Induce Treg to Teff Conversion.

Figure 6:
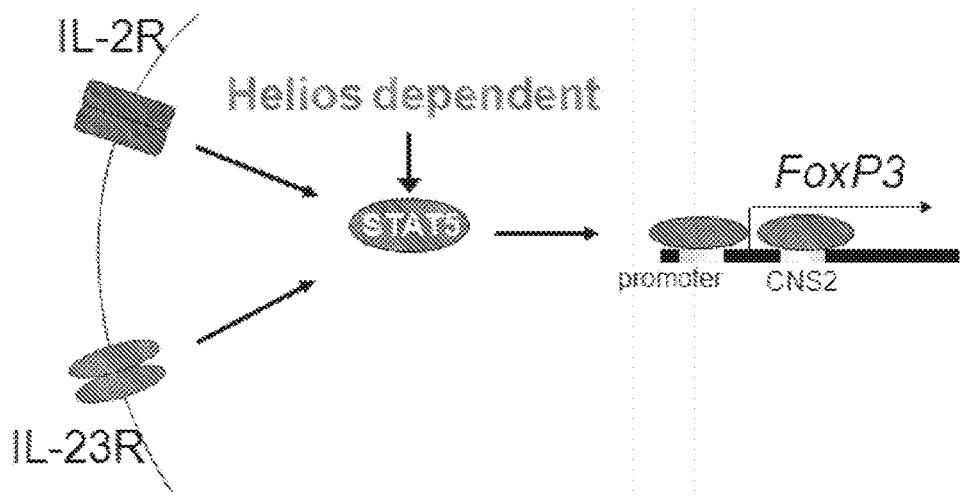
FIG. 6 shows a relevant Treg pathways in the inflammatory tumor microenvironment. Treg stabilize their suppressive phenotype by 1) enhanced IL-2 responsiveness via a Helios dependent genetic program and/or 2) enhanced STAT5 activation by IL-23R signaling that is uniquely operative within the tumor microenvironment. The blockade of either signaling pathway induces Treg conversion.
Figure 7A:
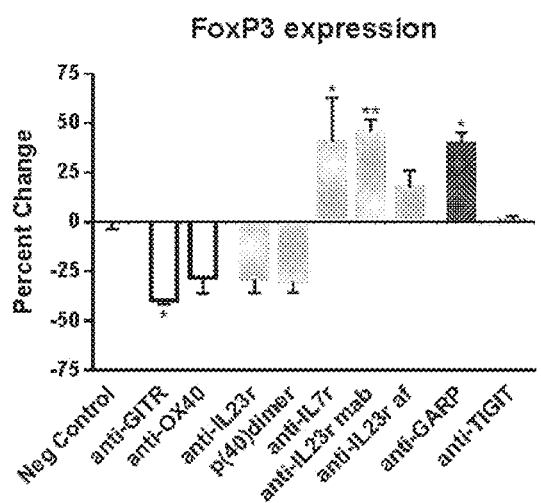
FIGS. 7A-7D shows that ligation of specific interleukin receptors induces Treg conversion in vitro. Receptors of interest were screened for loss of FoxP3 (FIG. 7A) and gain on IFN-γ expression (FIG. 7B). Anti-IL-23R, which resulted in the highest IFN-γ expression, was selected for further analysis. The kinetics of anti-IL-23R ligation on Treg conversion was assessed at 24 and 120 hours (5 days). A significant decrease in FoxP3 (FIG. 7C) and subsequent increase in IFN-γ (FIG. 7D) was observed when anti-IL-23R was co-cultured with Treg after 24 hours of stimulation was observed. ANOVA: * p<0.5  p<0.01 * p<0.001 **** p<0.0001.
Figure 7B:
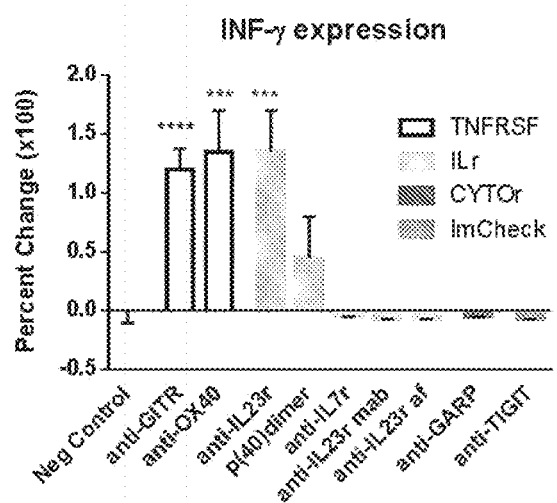
Figure 7C:
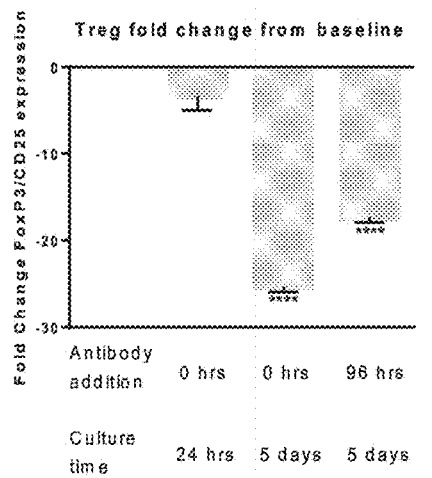
Figure 7D:
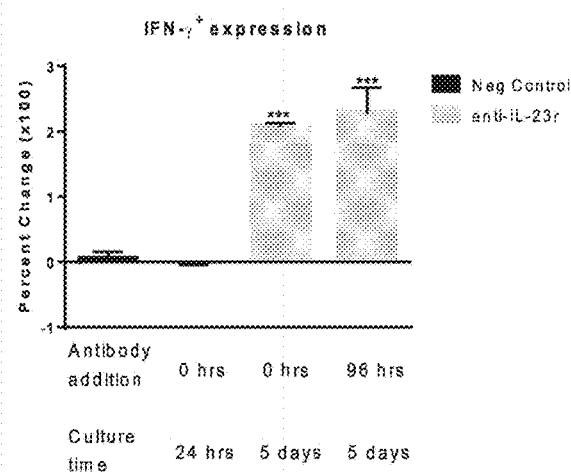

Two major signaling pathways maintain Treg stability within the tumor microenvironment (TME): 1) a Helios-dependent pathway that enhances IL-2R responsiveness and STAT5 activation and/or 2) an IL-23R signaling pathway that activates STAT5 within intratumoral Treg (FIG. 6). Blockade of either one of these signaling pathways induces Treg conversion as described below.

FIGS. 7A-7D shows antibodies found to induce conversion of Treg→Teff. Anti-IL-23R antibody treated Tregs showed decreased FoxP3 and increased IFN-γ expression compared to controls (FIGS. 7A-7D).

Converted Th1-Like nTregs Mediate Stronger Antitumor Activity

Figure 8:
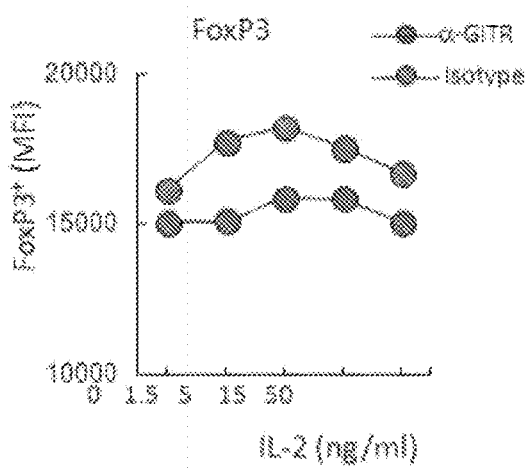
FIG. 8 shows that FoxP3 and IFN-γ expression after engagement of GITR induces Helios downregulation in CD4 Treg. FoxP3$^+$CD4 Treg were isolated from spleens of wild type B6 mice and cultured in the anti-CD3/CD28 coated wells in the presence of IL-4, increasing doses of IL-2, and anti-GITR (DTA-1) or isotype antibodies. After 5 days, the cells were analyzed for the levels of FoxP3 expression and IFN-γ production.
Figure 8:
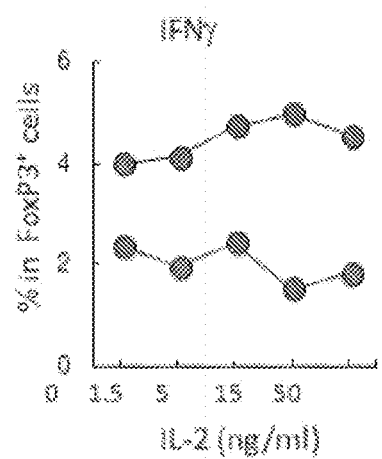

Isolated pure populations of homogeneous CD4 Treg cells were tested for differentiation into CD4 Teff cells after antibody engagement of Treg target receptors that included TNFRSF members (anti-GITR, anti-OX-40, anti-4-1BB) and others (e.g., anti-CD47 and anti-Nrp-1). This initial analysis of isolated CD4 Treg indicated that engagement of GITR by antibodies in the presence of IL-4 leads to a Treg→Teff conversion associated with downregulation of FoxP3 and Helios and upregulation of IFNγ production (FIG. 8).

Figure 9A:
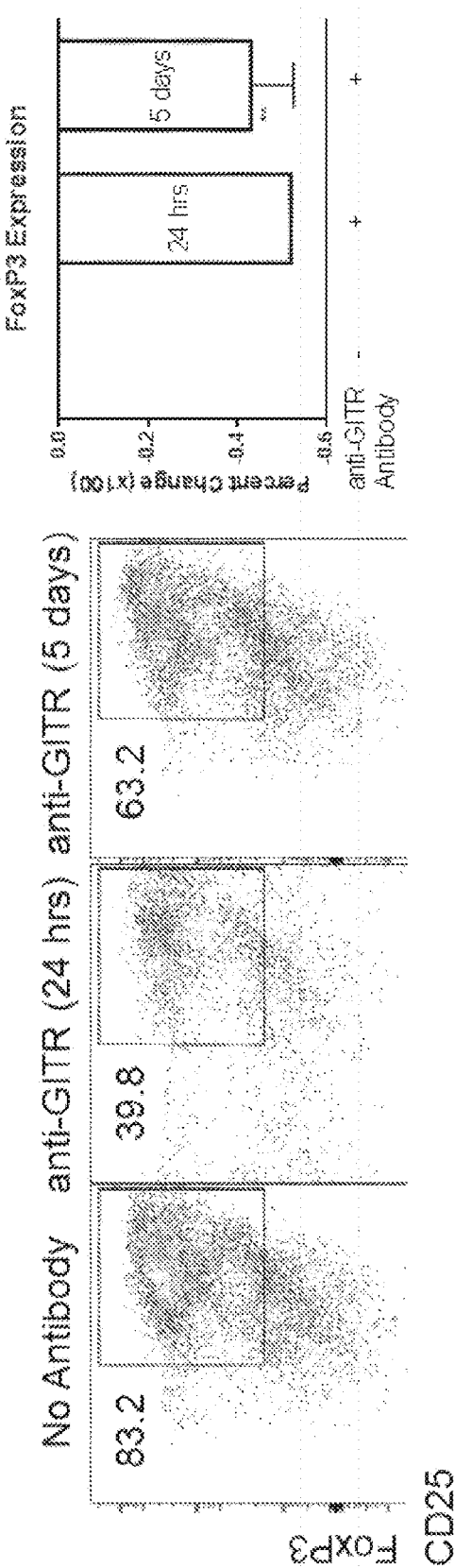
FIGS. 9A-9B provide confirmation of the in vitro conversion assay using a known TNF receptor super family member GITR agonist. Sorted C57BL/6 (WT) Treg (>90% pure CD4$^+$CD25$^+$) were cultured with plate bound anti-CD3/anti-CD28 in the presence of IL-2 and IL-4 for 24 hours or 5 days, and then assessed for conversion defined as loss of FoxP3 and gain of IFN-γ expression. The representative dot plots for Treg (gated on TCR$^+$CD4$^+$ cells) (FIG. 9A) and IFN-γ$^+$ cells (gated on FoxP3$^+$ cells) (FIG. 9B) with graphical representation of change from control (no antibody) are shown. ANOVA:  p≤0.01 ** p≤0.0001.
Figure 9B:
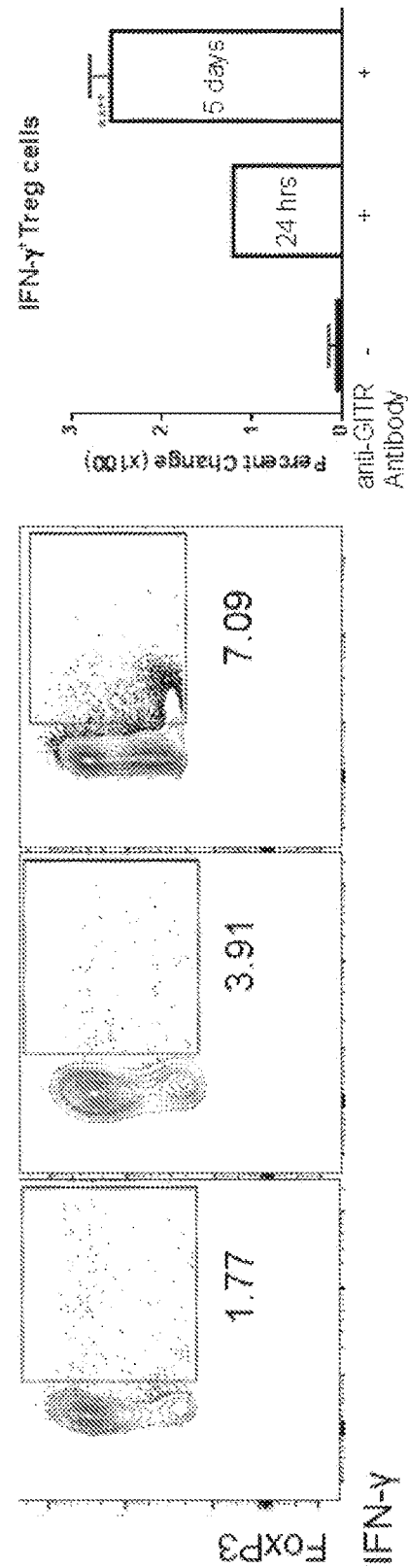
Figures 10A, 10B, 10C:
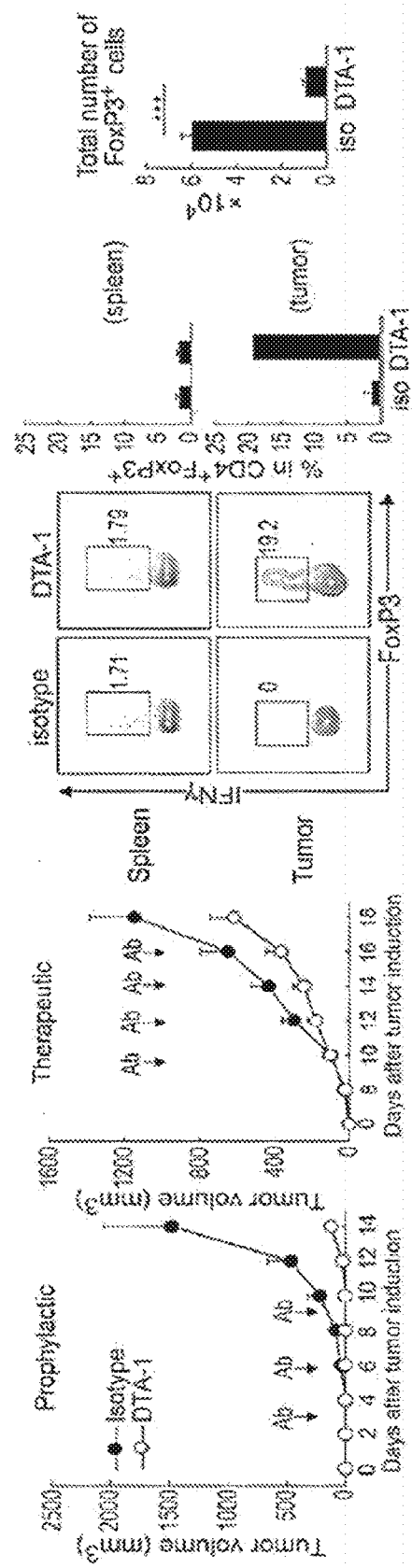
FIGS. 10A-10C show that treatment with GITR agonist induces Treg conversion in TME. Wild type (WT) mice were inoculated with B16/F10 subcutaneously and treated with an intraperitoneal injection prophylactically on days 3, 6 and 9 or therapeutically on days 10, 12, 14 and 16).

The GITR agonist, DTA-1, has been suggested to alter the stability of Treg cells. An in vitro assay was used to test if loss of stability resulted in Treg conversion to Th1-like effector cells. FIGS. 9A and 9B shows data from an experiment in which sorted C57BL/6 (WT) Treg (>90% pure CD4+CD25+) were cultured with plate bound anti-CD3/anti-CD28 in the presence of IL-2 and IL-4 for 24 hours or 5 days, and then assessed for conversion defined as loss of FoxP3 and gain of IFN-γ expression. In this system, GITR agonist DTA-1 showed loss of FoxP3 and increase in IFN-γ expression (FIGS. 9 and 9B). It can be seen that when the Ab was used either prophylactically or therapeutically, engagement of GITR on Tregs by anti-GITR Ab (DTA-1) led to reduction in tumor size compared to the negative control (FIG. 9A). Anti-GITR also led to an effector phenotype in tumors, but not in the spleen, as shown in FIGS. 10B and 10C.

Treg Conversion by Anti-IL-23R Antibody

Figure 11A:
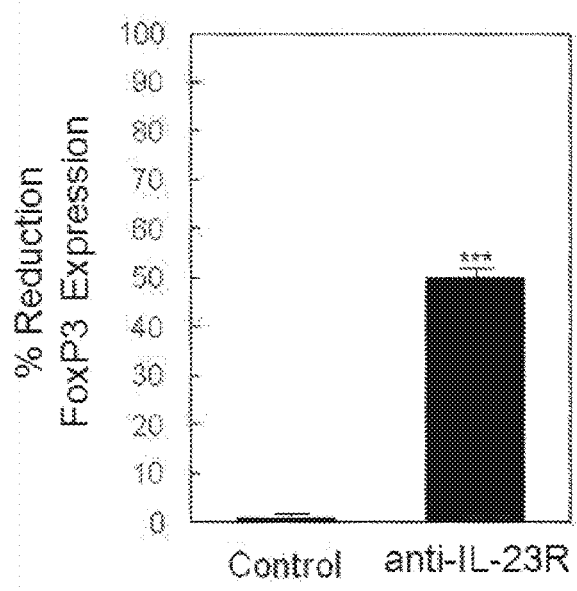
FIGS. 11A-11B show in vitro screen results for Treg conversion by anti-IL-23R antibody. Naïve peripheral Treg were sorted at >90% purity and cultured for 5 days in the presence of plate bound anti-CD3 and anti-CD28 as well as soluble IL-2 (20 ng/mL) and IL-4 (50 ng/mL).
Figure 11B:
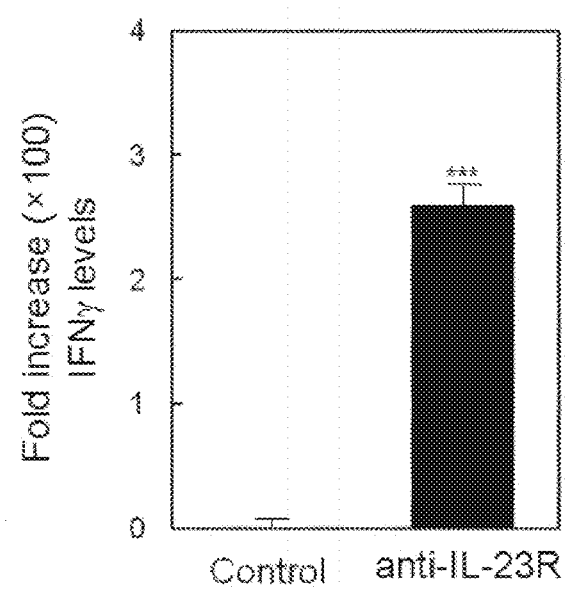
Figure 12:
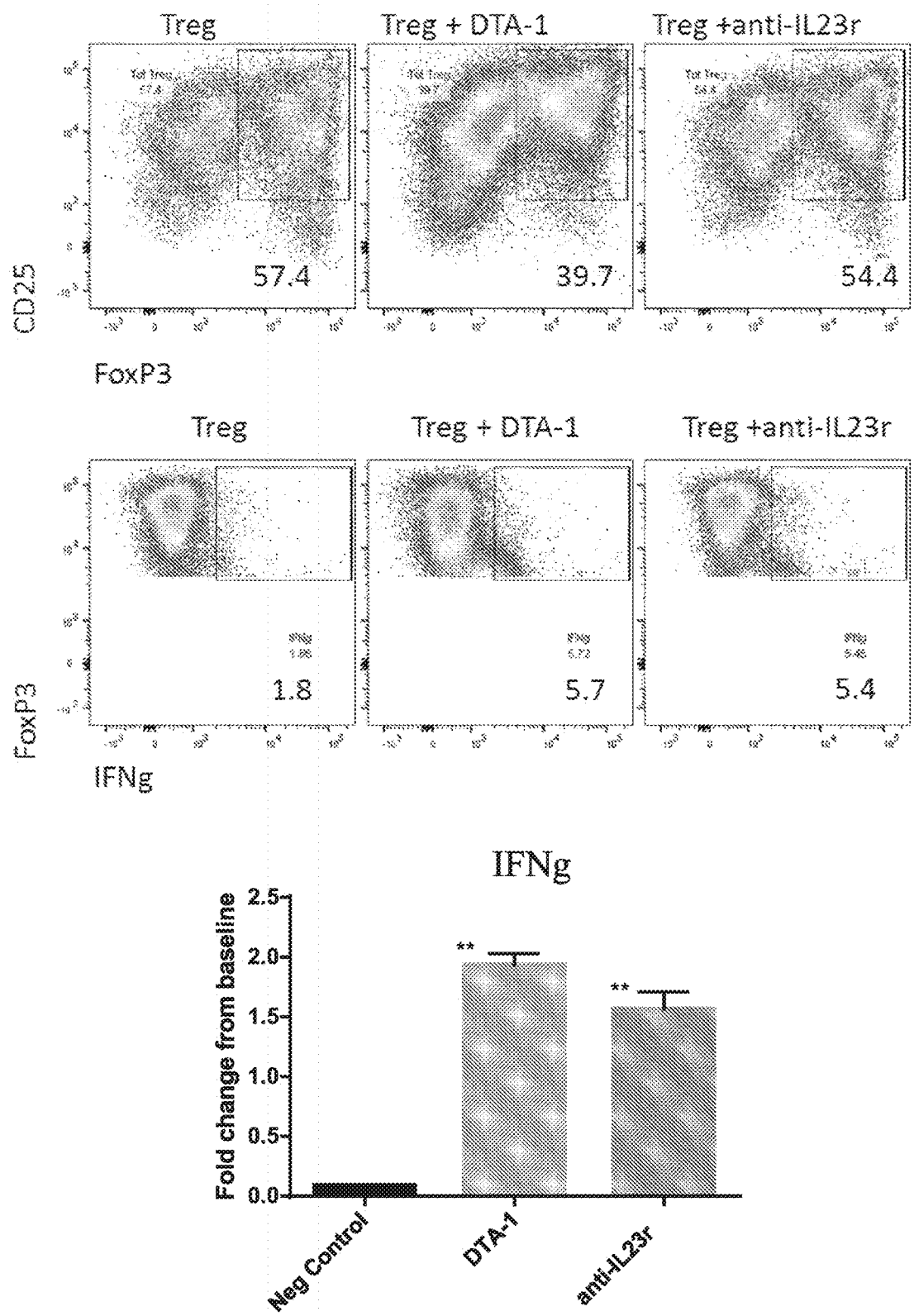
FIG. 12 shows FoxP3 and CD25 expression in sorted Treg plated with plate bound anti-CD3/anti-CD28 and cultured for 5 days in the presence of IL-2 (20 ng/mL) and IL-4 (50 ng/mL). Antibodies were added at 10 ng/mL on Day 0 of culture.
Figure 13:
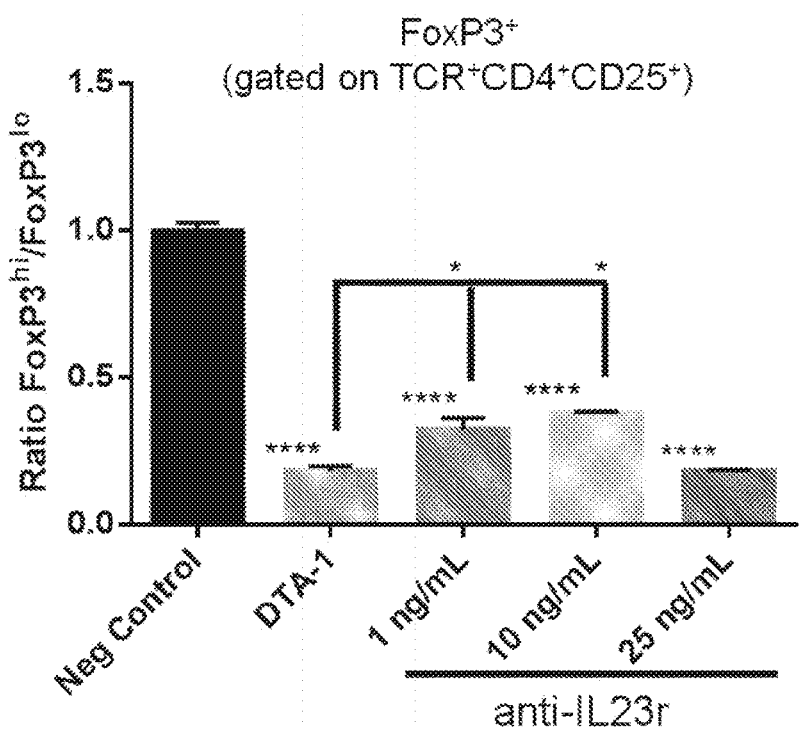
FIG. 13 shows that FoxP3$^{hi}$ expression is lost with anti-IL-23R dose response. Sorted Treg were plated with plate bound anti-CD3/anti-CD28 and cultured for 5 days. In the presence of IL2 (20 ng/mL) and IL4 (50 ng/mL), anti-IL-23R antibodies were added at 1, 10 and 25 ng/mL incremental doses on Day 0 of culture. The reduced ratio of FoxP3$^{hi}$ to FoxP3$^{lo}$ Treg is seen in the positive control (anti-GITR [DTA-1] 10 ng/mL) as well as in the anti-IL-23R treated cells.

Blocking of IL-23R signaling in Treg under inflammatory conditions (IL-2$^+$IL-4$^+$) was found to induce Treg conversion as judged from reduced expression of FoxP3 and production of IFN-γ (FIGS. 11A and 11B). As can be seen in FIG. 12, like DTA-1, anti-IL-23R antibody lowers the expression of FoxP3 and increases the expression of IFN-γ in Tregs plated with plate bound anti-CD3/anti-CD28 and cultured in the presence of IL2 and IL4. This effect was found to be dependent on the dose of anti-IL-23R antibody (FIG. 13).

Figure 14:
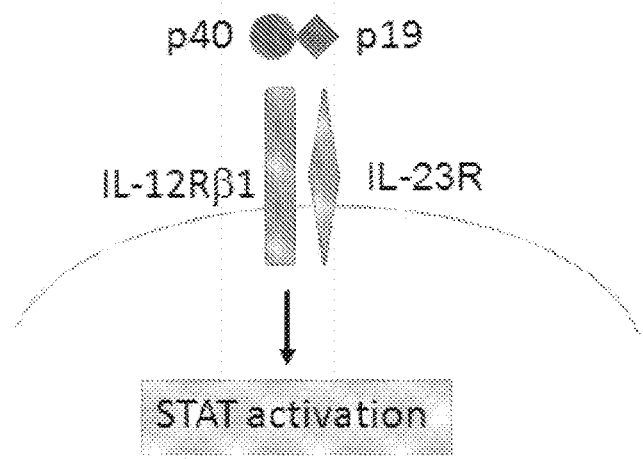
FIG. 14 provides a schematic illustration of the IL-23 receptor complex. The IL-23 cytokine consisting of p19 and p40 chains, binds to the heterodimeric receptor IL-23R and IL-12Rβ1.

Moreover, unlike other anti-IL-23R antibodies which fail to induce conversion (not shown), the anti-IL-23R antibody with conversion activity recognizes the extracellular domain of the IL-23R chain rather than the IL-12Rβ common chain that also binds to IL-12p40 (FIG. 14).

IL-23R Expression

Figure 15:
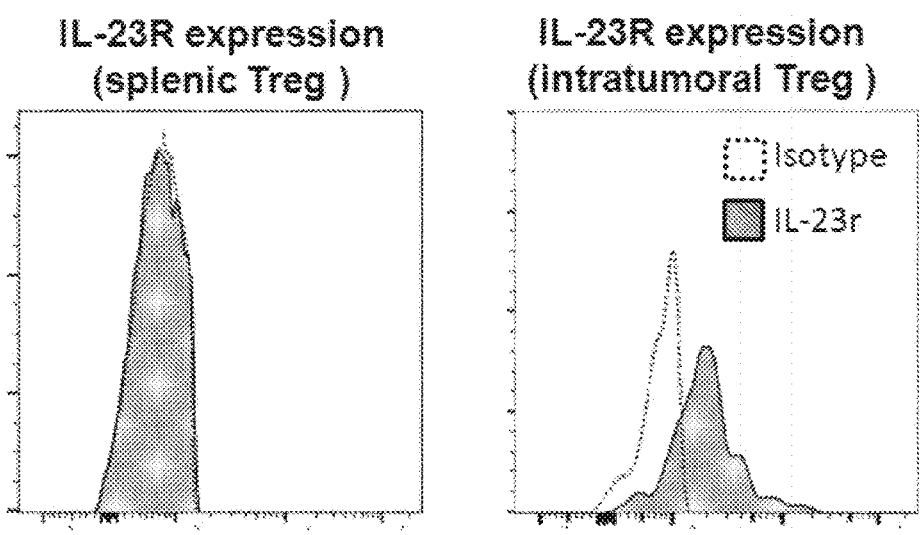
FIG. 15 shows in vivo intratumoral Treg conversion and IL-23R expression. Mice were inoculated with B16/F10 cancer cells and assessed for IL-23R expression in splenic (left) and tumor infiltrating (right) Treg populations.
Figure 16:
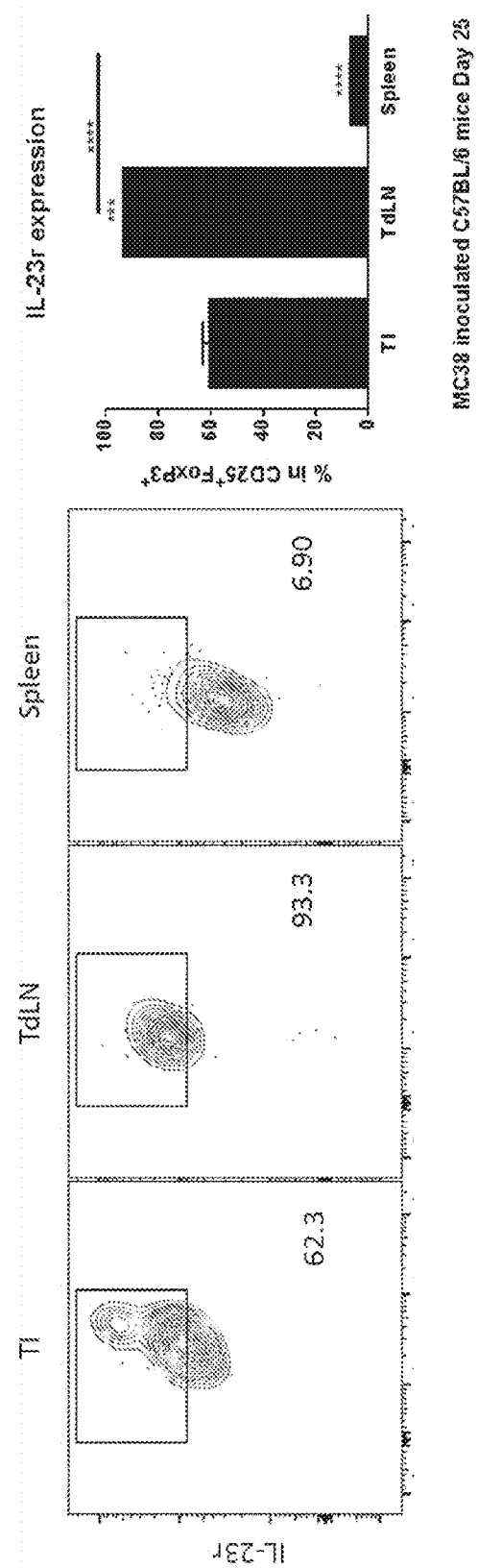
FIG. 16 shows IL-23R expression in tumor dLN and tumor infiltrating Treg cells. IL-23R expression is significantly increased in Treg found in the tumor and tumor draining lymph node (TdLN) compared to the spleen. MC38 cells were subcutaneously inoculated in C57BL/6 mice. Measurements were made (no treatment) on day 25 after inoculation. The representative FACs dot plots gated on $TCR^+CD4^+CD25^+FoxP3^+$ cells with graphical analysis are shown [Mean±SEM ANOVA *p>0.001 **p.0.0001].
Figure 17:
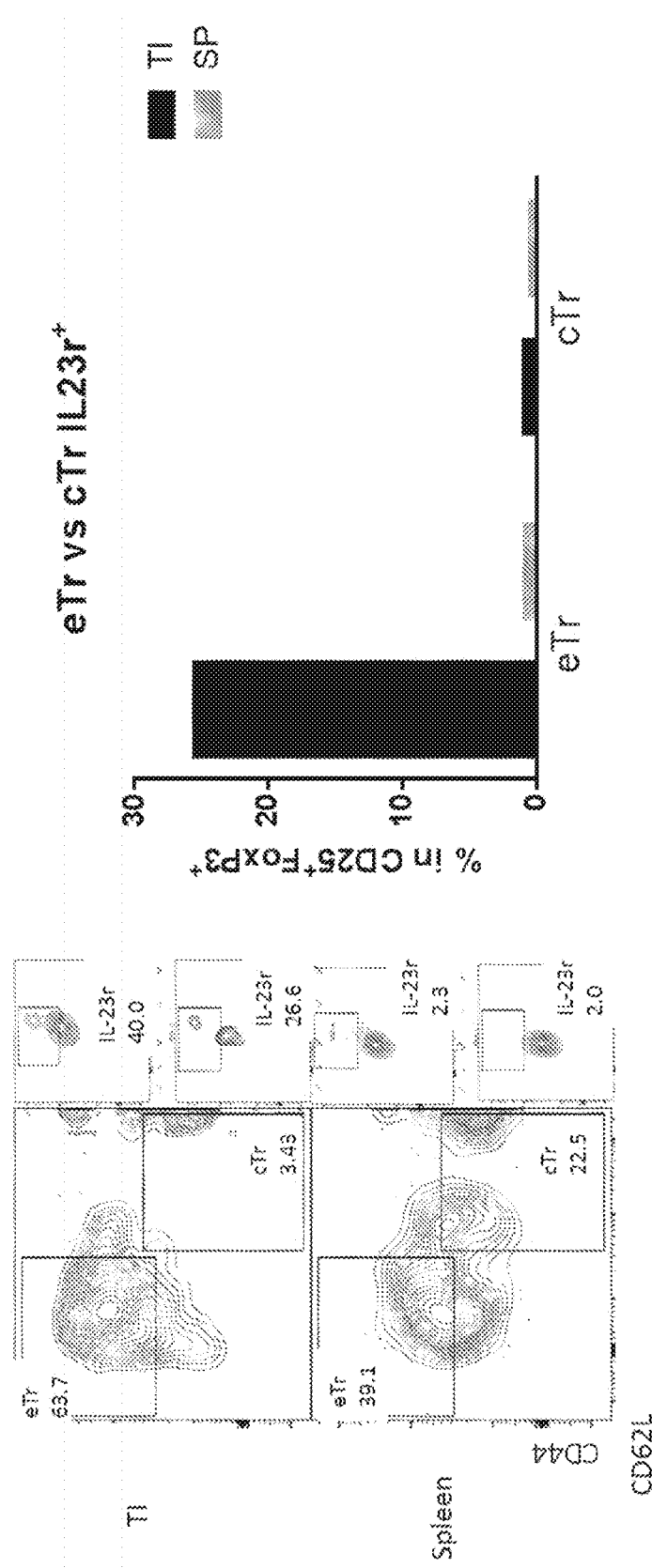
FIG. 17 shows that effector Treg (eTr) express high levels of IL-23R. Intratumoral effector Treg (eTr) have significantly increased IL-23R expression compared to TI central Treg (cTr) and splenic Treg. MC38 cells were subcutaneously inoculated in C57BL/6. Measurements were made on day 25 after inoculation. Representative FACs dot plot gated on $TCR^+CD4^+CD25^+FoxP3^+$ cells with graphical analysis are shown.
Figure 18:
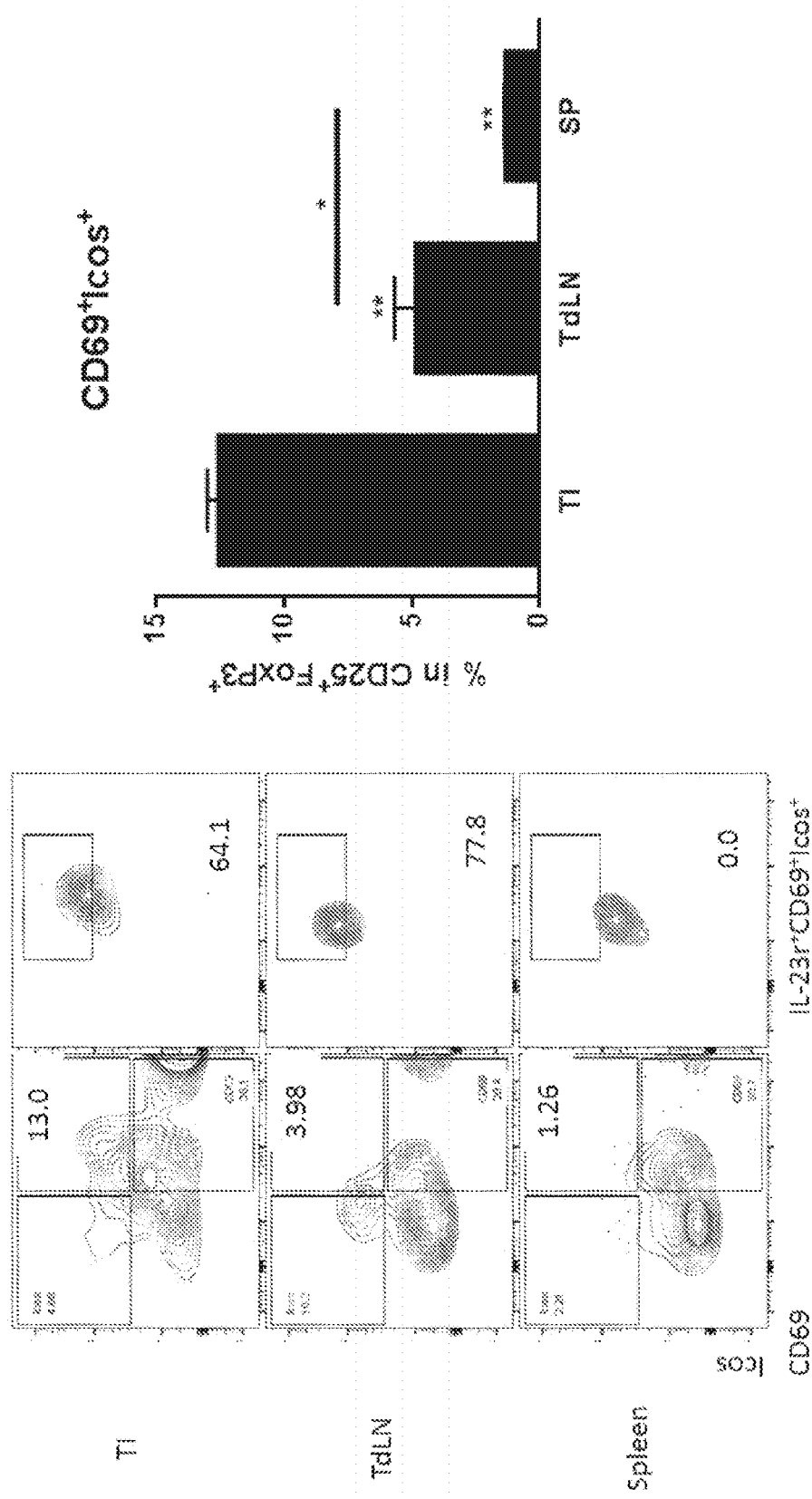
FIG. 18 shows that tumor infiltrating $CD69^+Icos^+$ Treg express high levels of IL-23R. Double positive $CD69^+Icos^+$ expression in tumor infiltrating (TI) Treg is significantly increased compared to TdLN and Spleen (SP) in MC38 inoculated mice. Representative FACs dot plots gated on $TCR^+CD4^+CD25^+FoxP3^+$ cells with graphical analysis are shown [Mean±SEM ANOVA: * p>0.05 **p>0.01].
Figure 19:
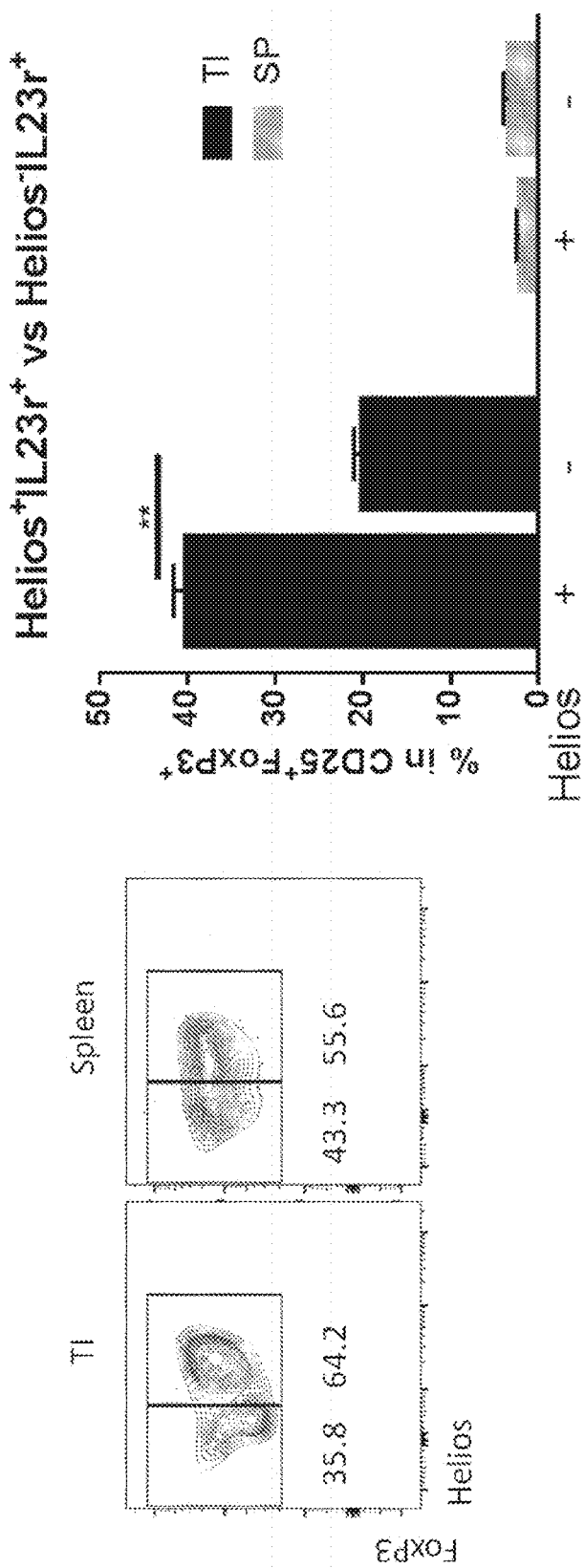
FIG. 19 shows that $Helios^+$ Treg express high levels of IL-23R. $Helios^+$ TI Treg have significantly increased IL-23R expression compared to $Helios^-$ TI Treg. Representative FACs dot plots gated on $TCR^+CD4^+CD25^+FoxP3^+$ cells with graphical analysis are shown[Mean SEM Student's T test: **p>0.01].
Figure 20:
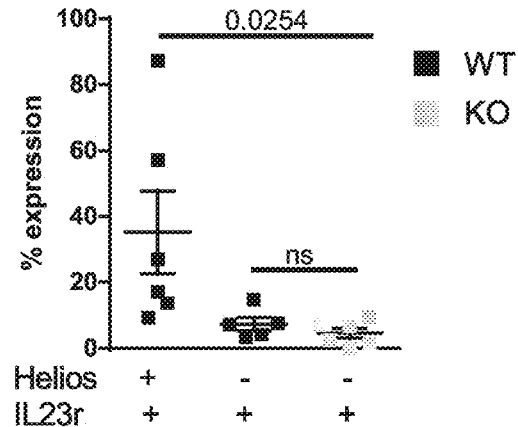
FIG. 20 shows that $Helios^{+WT}$ tumor infiltrating Treg have significantly increased IL-23R expression in CD69+ Treg compared to $Helios^{-WT}$ and $Helios^{KO}$ TI Treg. Helios (WT) and $Helios^{f/f} FoxP3^{cre}$ (KO) mice were inoculated subcutaneously with F10/B16 collected on day 21. The graphical analysis gated on $TCR^+CD4^+CD25^+FoxP3^+$ for IL-23R expression (top), Treg subsets including CD69+ eTr and cTr (middle), and IL-23R expression in Treg subsets (bottom) are shown [Mean±SEM ANOVA or Student's T test: **p>0.01].
Figure 20:
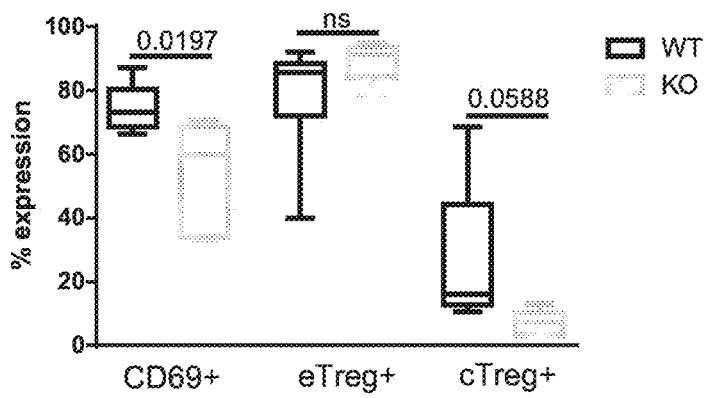
Figure 20:
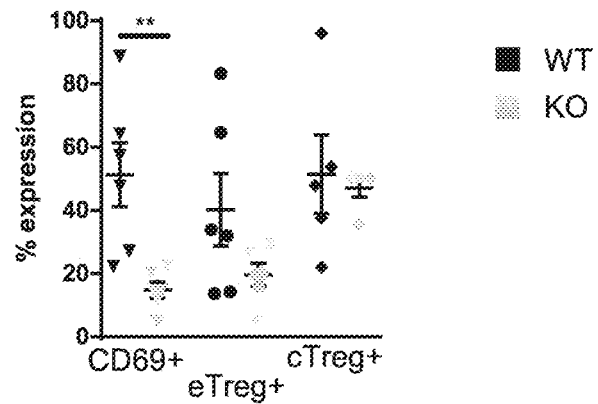

In terms of being able to target tumors specifically, it is relevant and important to note that Treg from tumors express high levels of IL-23R, while splenic Treg were found not to do so (FIG. 15). IL-23R expression is significantly increased in Treg found in the tumor and tumor draining lymph node (TdLN) compared to the spleen (FIG. 16). It was also found that effector Treg (eTr) express high levels of IL-23R (FIG. 17). Tumor infiltrating CD69$^+$Icos$^+$ also express high IL-23R (FIG. 18). FIG. 20 shows that Helios$^+$ Treg express high levels of IL-23R. Indeed, it was found that IL-23R expression is reduced in cells in which Helios is knocked out (FIG. 20), demonstrating the dependence of IL-23R expression on Helios.

IL-23R Regulates FoxP3 and IFN-γ Expression

Figure 21:
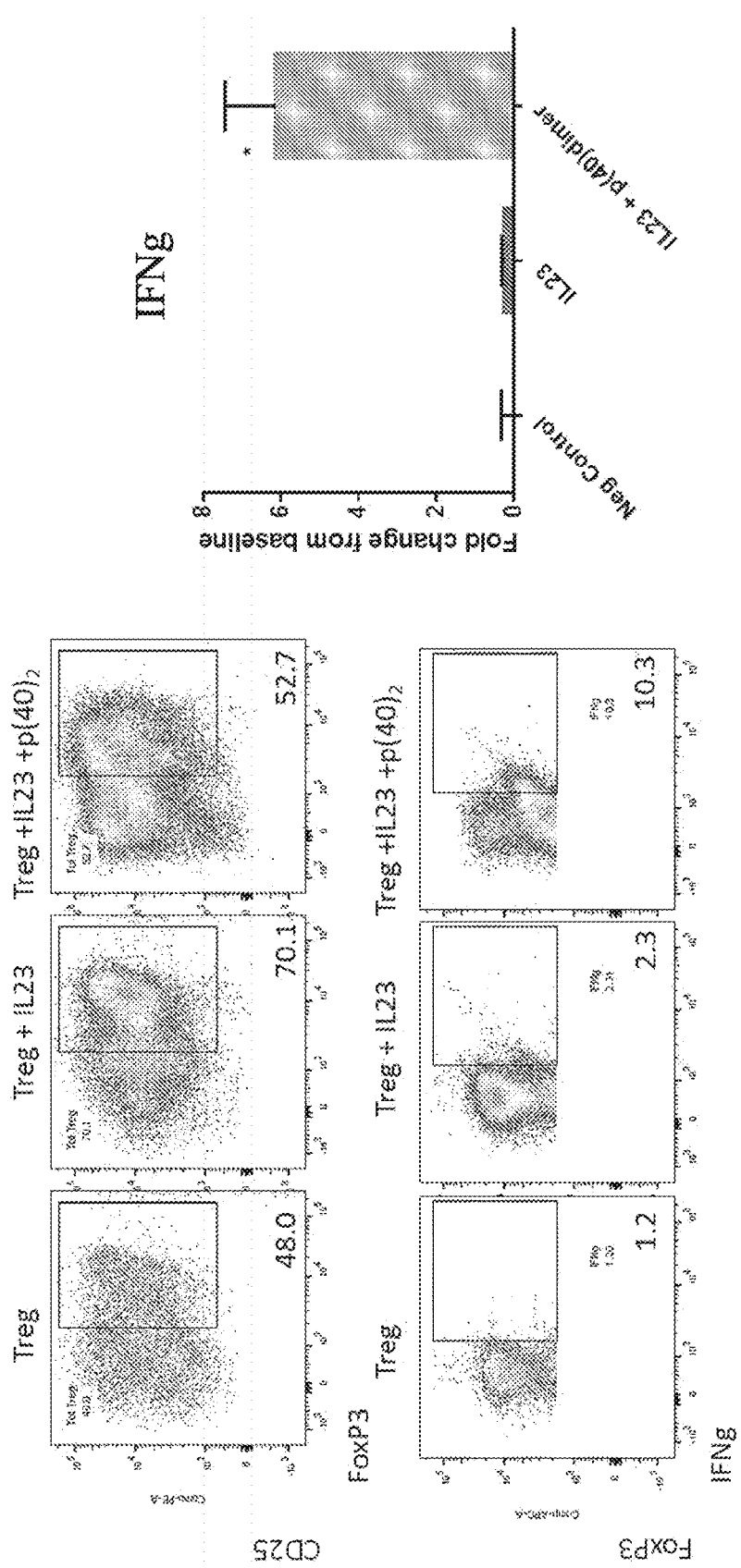
FIG. 21 shows that IL-23 regulates expression of FoxP3 and IFN-γ. Sorted Treg (>90% pure $CD3^+CD4^+CD25^+$) were plated with plate bound anti-CD3/anti-CD28 (10 μg/mL in 1×PBS) and in the presence of IL2 (20 ng/mL) and IL4 (50 ng/mL) and cultured for 5 days (120 hours). IL-23 recombinant protein was added at 25 ng/mL time 0 (T0) of culture and $p(40)_2$ was added for the last 24 hours of culture (T96). Representative dot plots are shown for decreased expression of FoxP3 (top left) and increased expression of IFN-γ (bottom left). The graphical representation (right) of the fold change from baseline (negative control or no antibody) is shown as mean±SEM. ANOVA: p<0.05.

In an in vitro experiment in which sorted Treg were plated with plate bound anti-CD3/anti-CD28 and cultured in IL-2 and IL-4 for 5 days, it was found that FoxP3 expression is increased after treatment with recombinant IL-23 protein and then somewhat decreased in cells treated with recombinant IL-23 protein and p(40)$_2$ (FIG. 21). Conversely, the IFN-γ levels increased after treatment with recombinant IL-23 protein and p(40)$_2$ (FIG. 21).

Anti-IL-23R Antibody Effects on FoxP3 and IFN-γ Expression

Figure 22:
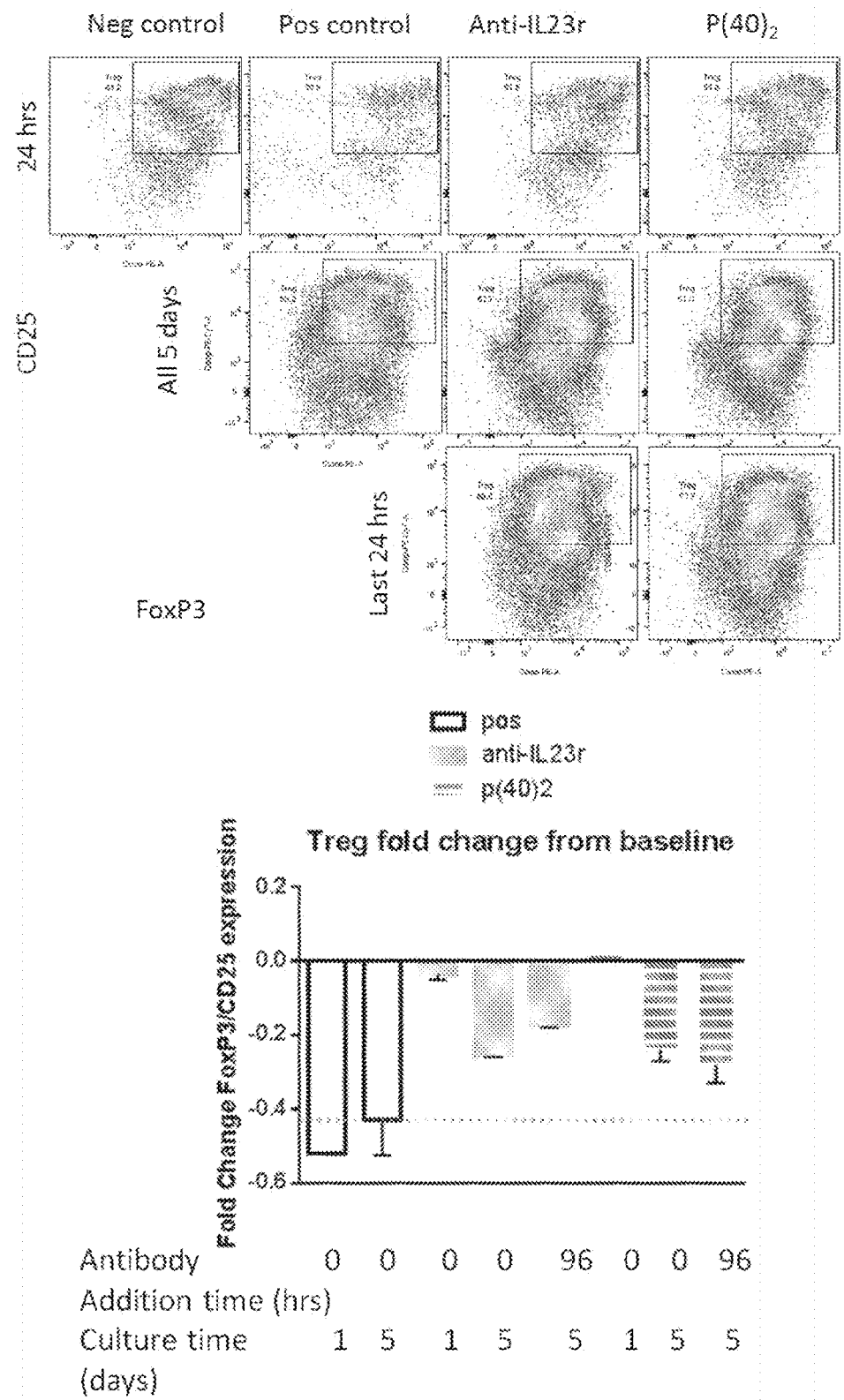
FIG. 22 shows CD25 expression in sorted Treg plated with plate bound anti-CD3/anti-CD28 and cultured for 5 days in the presence of IL2 (20 ng/mL) and IL4 (50 ng/mL). Antibodies and p40 homodimer were added at 0 and 96 hours and then cultured for 1 or 5 days.
Figure 23:
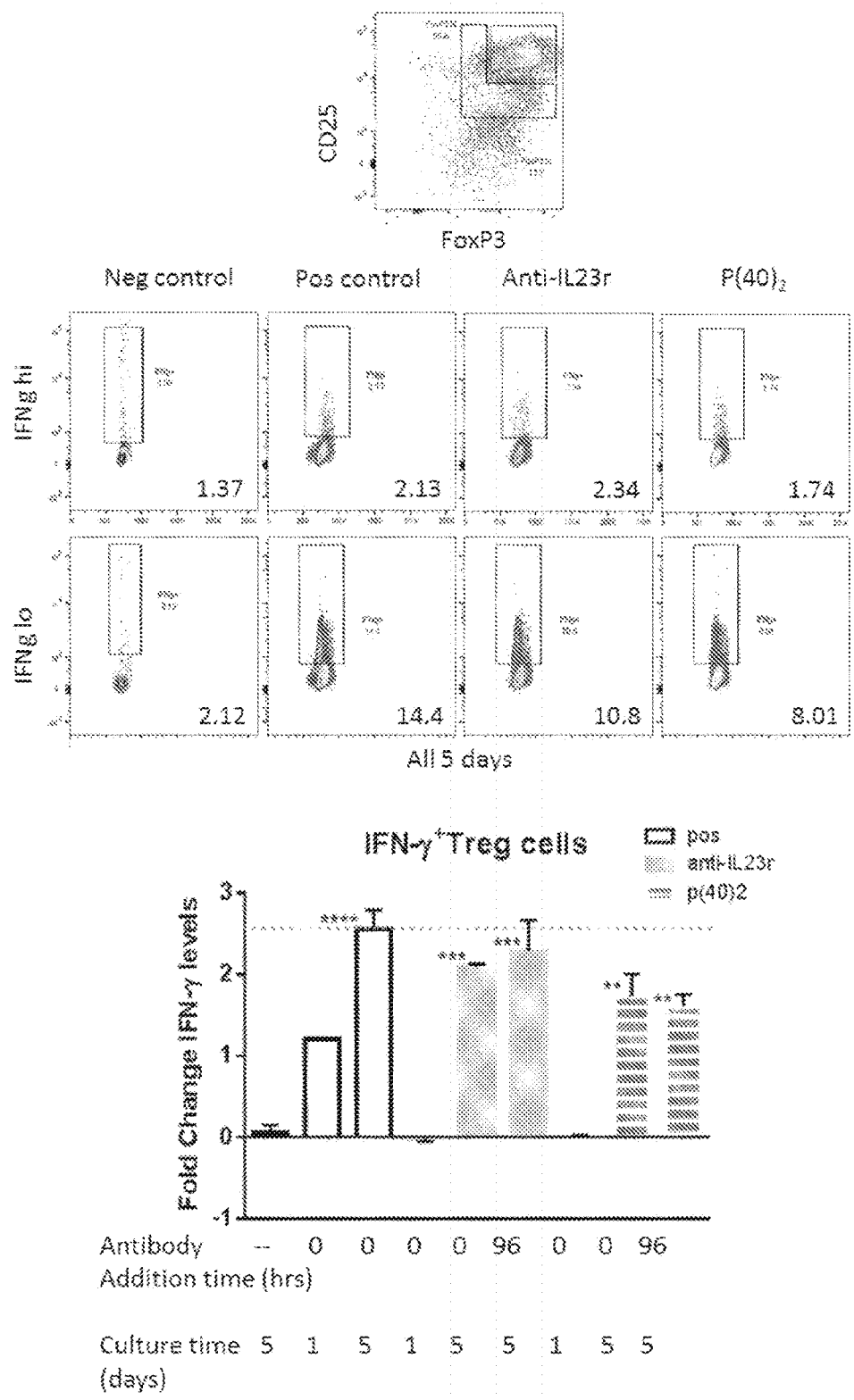
FIG. 23 shows IFN-γ expression and fractions of IFN-γ expressing cells in sorted Treg plated with plate bound anti-CD3/anti-CD28 and cultured for 5 days in the presence of IL2 (20 ng/mL) and IL4 (50 ng/mL). Antibodies and p40 homodimer were added at 0 and 96 hours and then cultured for 1 or 5 days.

Data in FIG. 22 shows that blocking IL-23R ligation by either anti-IL-23R antibody or P(40)$_2$ must occur after activation of the receptor to reduce FoxP3 expression. FIG. 23 also shows that blocking IL-23R ligation likely occurs after activation to induce IFN-γ expression in FoxP3$^{lo}$ cells.

Anti-Tumor Activity of Anti-IL-23R Antibody In Vivo

Figure 24:
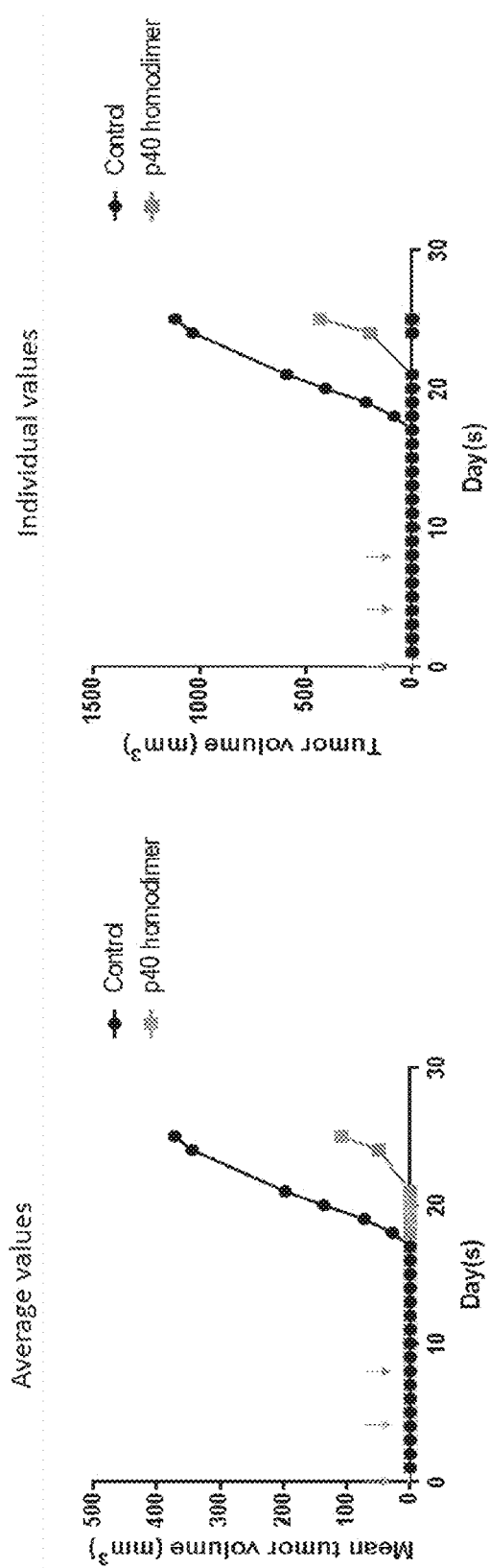
FIG. 24 shows tumor outgrowth in control (1×PBS) and p40 homodimer treated mice. Treatment (50 μg/mouse using an intraperitoneal injection) control (n=3) or p40 homodimer (n=4) was given on day 0, 4, and 8 as indicated by the arrows (↓). The tumor volume ($mm^3$) is represented as an average (left) and as individual values (right).

Tumor outgrowth was observed to be delayed in MC38 inoculated C57BL/6 mice treated with (p40)$_2$ homodimer (FIG. 24).

Figure 25A:
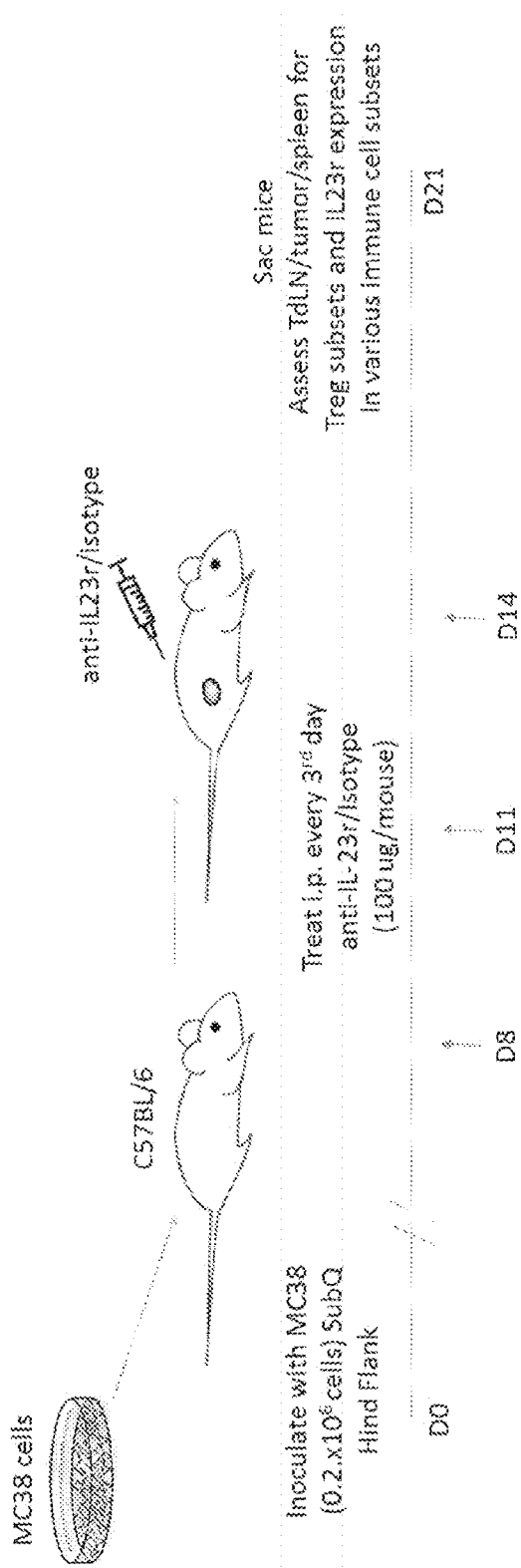
FIGS. 25A-25E show in vivo effects of anti-IL-23R treatment.
Figure 25B:
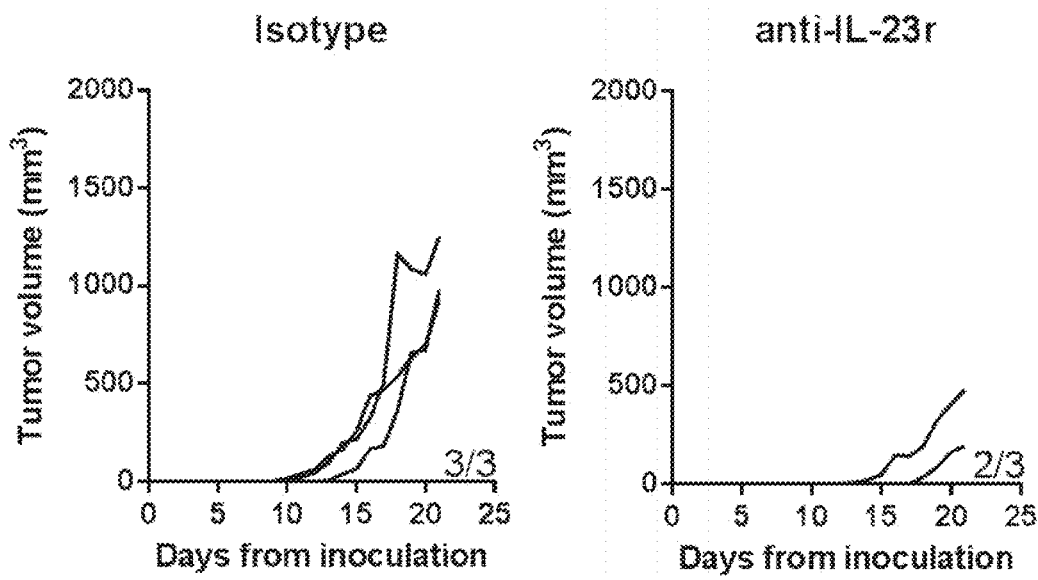
Figure 25C:
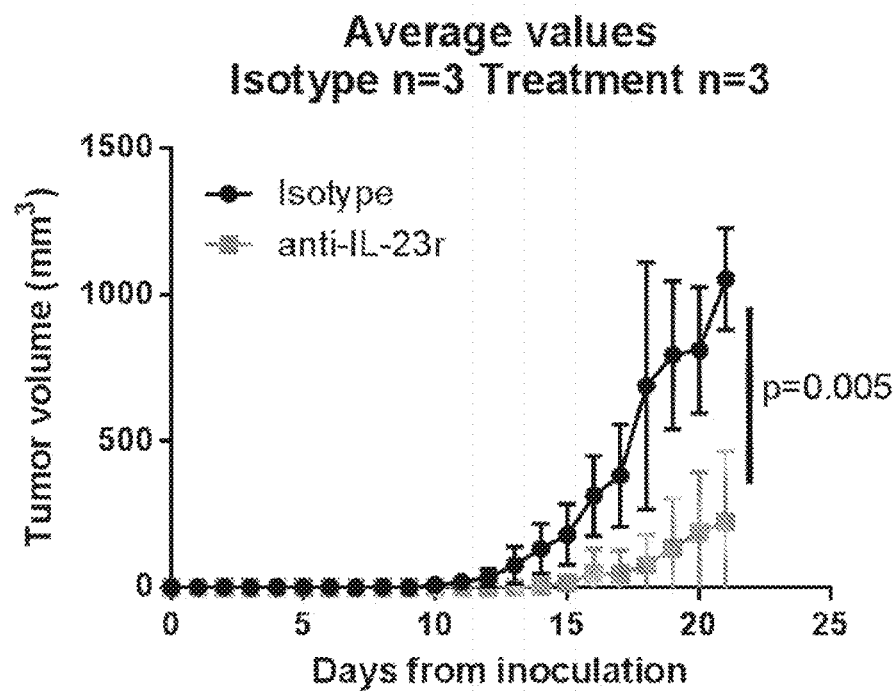
Figure 25D:
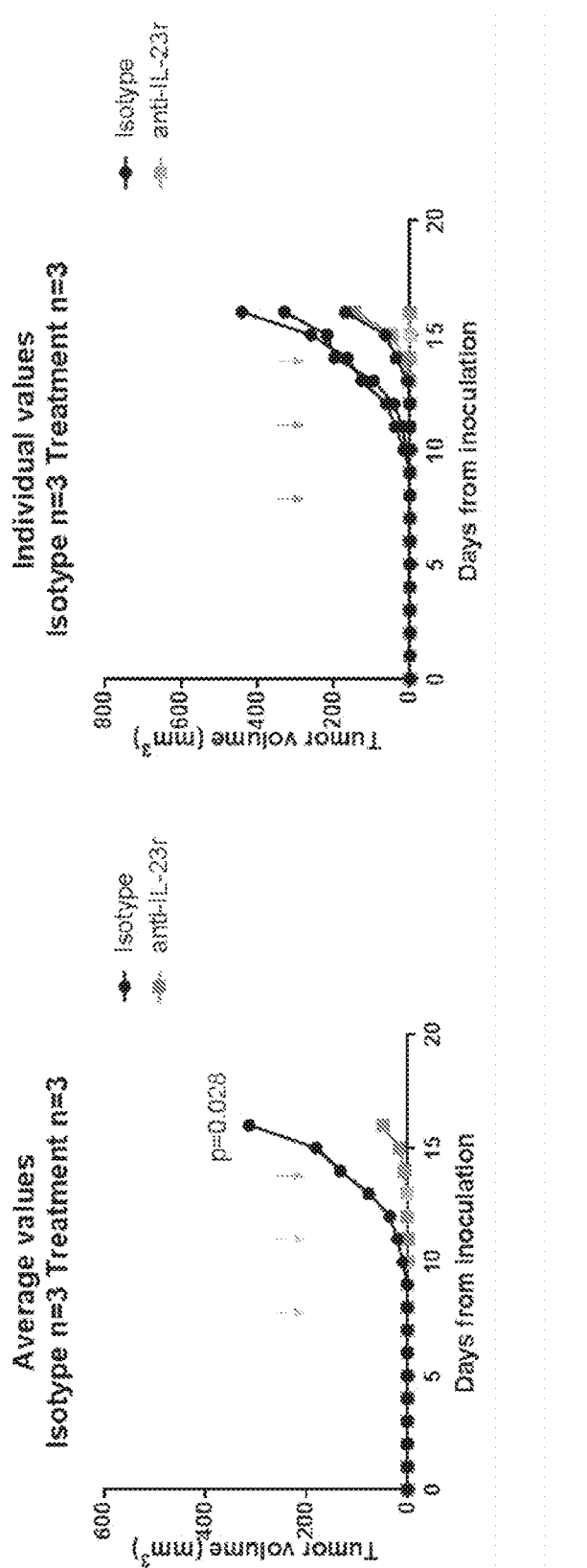
Figure 25E:
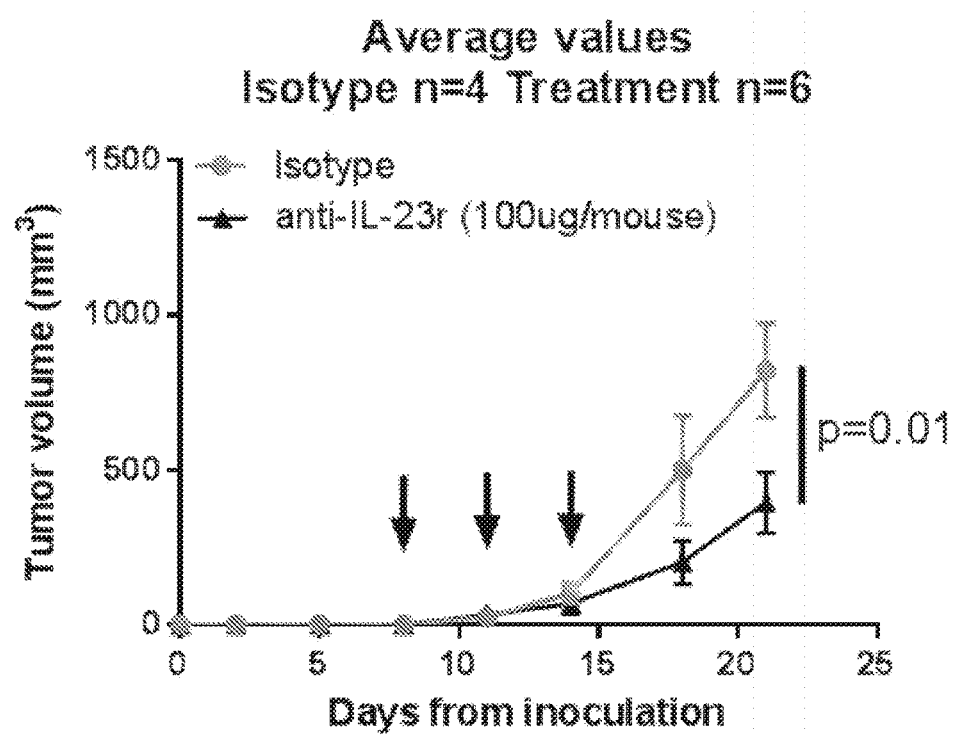

FIGS. 25A-25E show results from an experiment in which C57BL/6 mice were inoculated with MC38 cancer cells subcutaneously and thereafter administered anti-IL-23R antibody (or isotype control) before assessment of Treg subsets and IL-23R expression in various immune cell subsets (FIG. 25A). Growth curves for individual mice are shown in FIG. 25B. The graph in FIG. 25C shows that the third mouse that was administered anti-IL-23R antibody remained tumor-free. The data plotted as the average per treatment condition can be seen in FIGS. 25D and 25E.

Figure 26A:
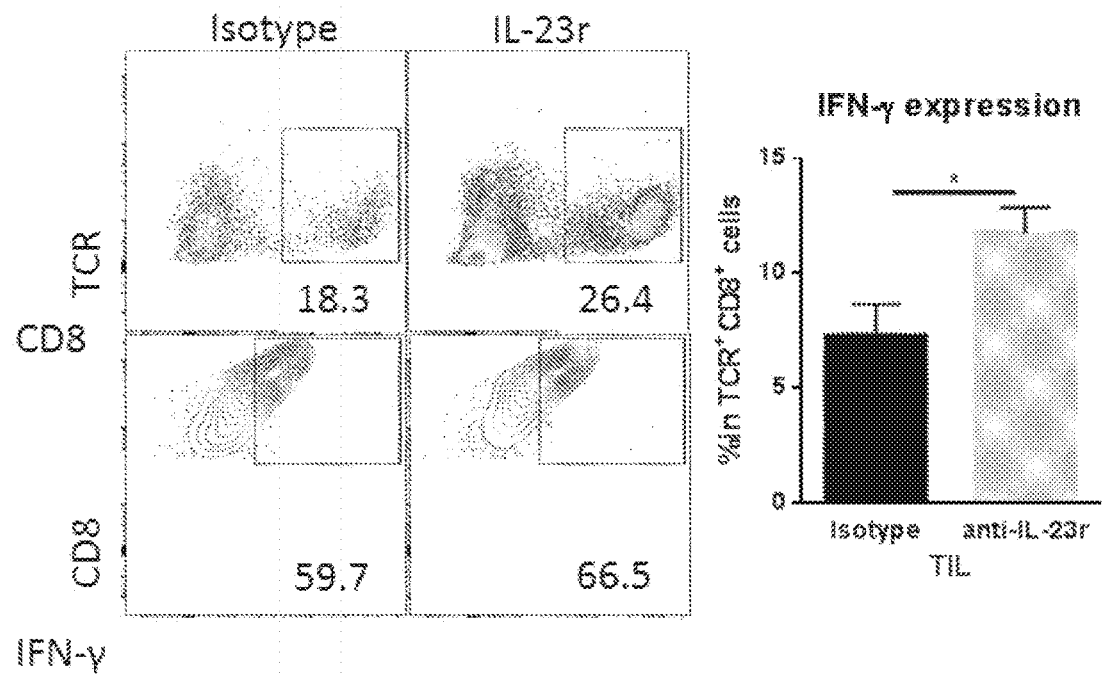
FIGS. 26A-26B show that anti-IL-23R induces intratumoral Treg conversion and increased antitumor activity.
Figure 26B:
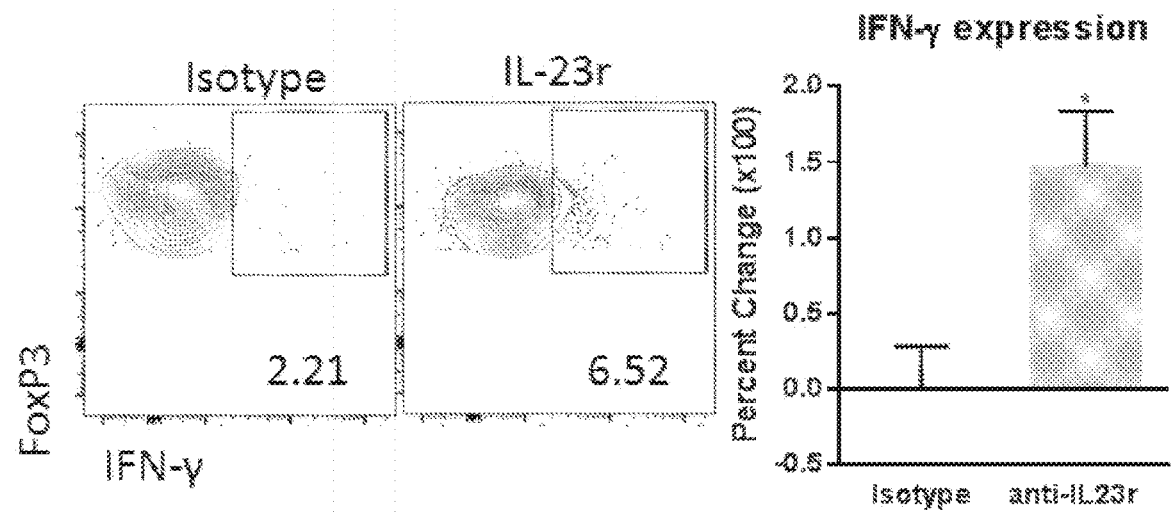

Treatment of mice inoculated with MC38 cancer cells with anti-IL-23R resulted in increased CD8 activity as indicated by IFN-γ expression (FIG. 26A) and induced intratumoral Treg conversion as indicated by increased IFN-γ expression (FIG. 26B).

Figure 27:
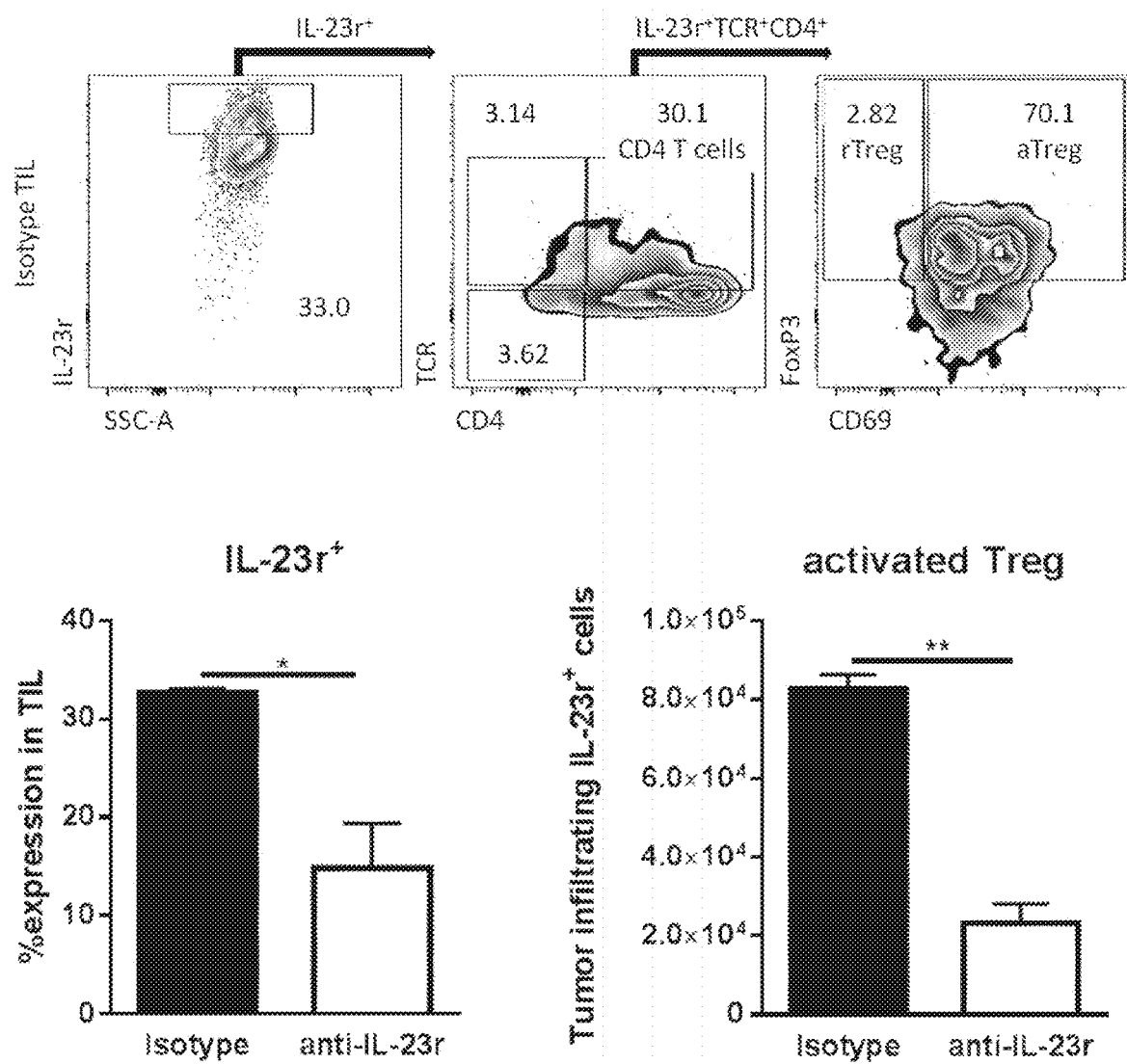
FIG. 27 shows that IL-23R expression is significantly decreased in anti-IL-23R antibody treated tumor and in tumor infiltrating activated Treg. Representative FACs dot plot gating strategy on single cells lymphocytes to aTreg (top left to right), graphical analysis of IL-23R+ intratumoral cell proportion (bottom left), and IL-23R+aTreg numbers (bottom right) collected on day 21 are shown [Mean±SEM Student's t test: *p>0.05 **p>0.01].
Figure 28:
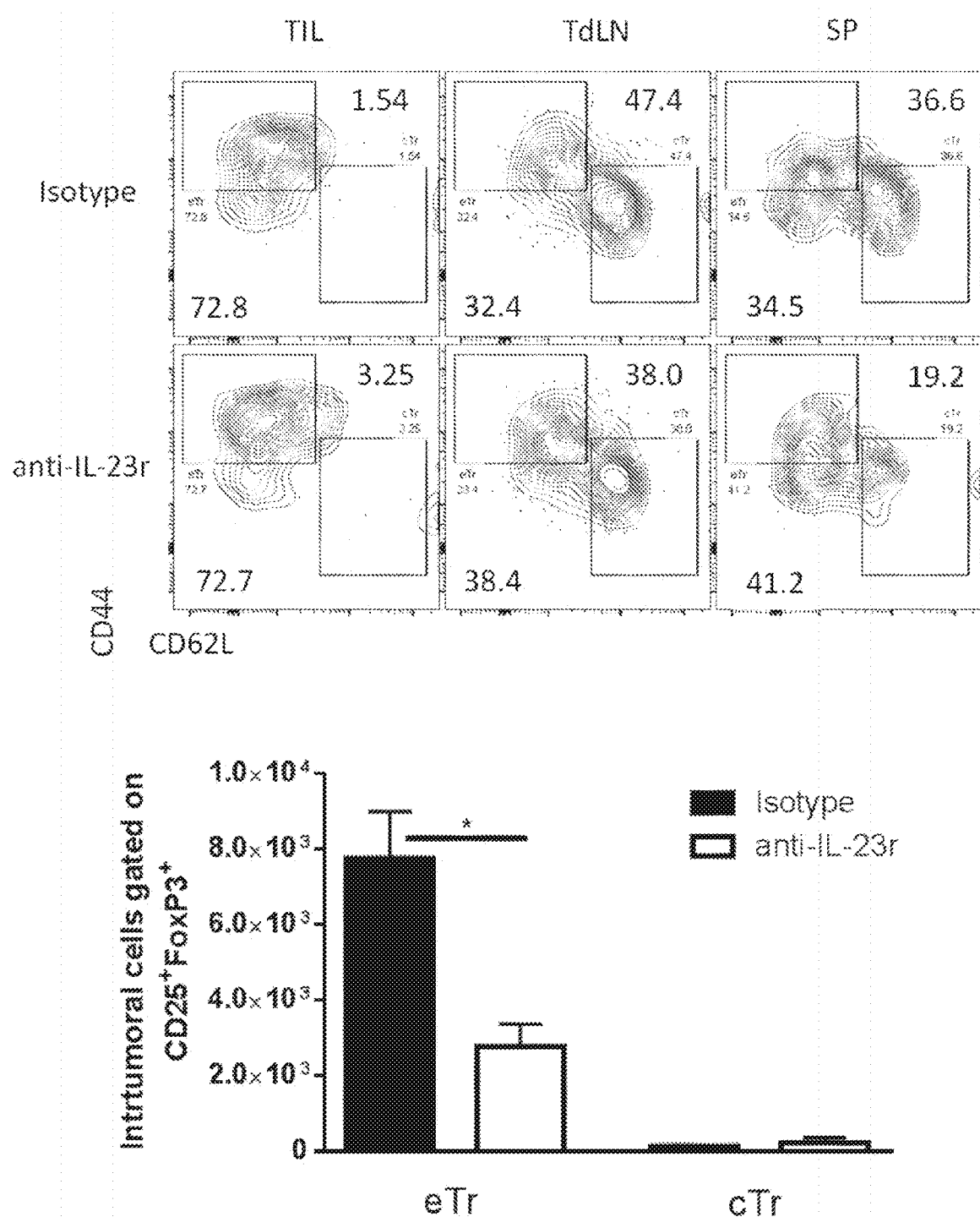
FIG. 28 shows that IL-23R expression is significantly decreased in eTr found in the tumor of anti-IL-23r antibody treated mice. Representative FACs dot plots gated on $TCR^+CD4^+CD25^+FoxP3^+$ cells with graphical analysis of IL-23r+ eTr and cTr collected on day 21 are shown [Mean±SEM Student's t test *p>0.05].
Figure 29:
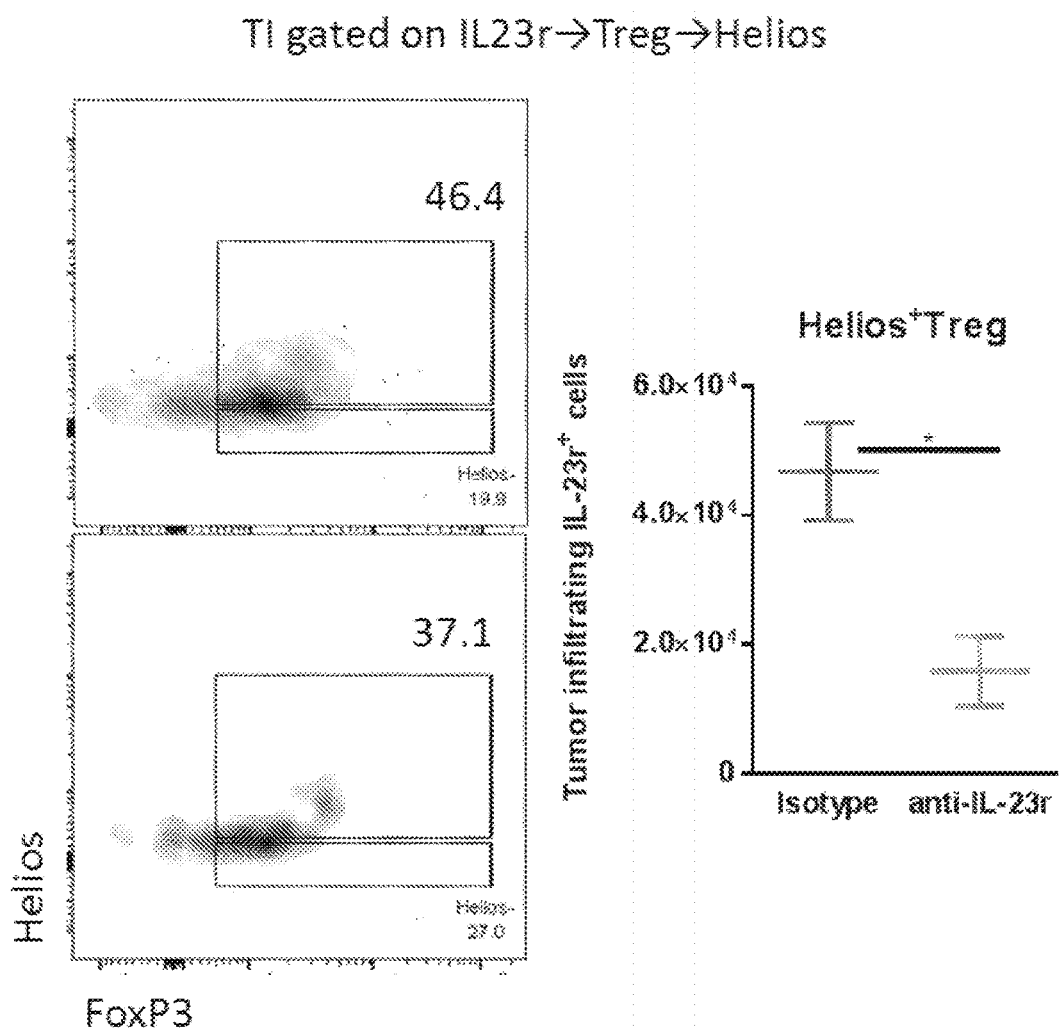
FIG. 29 shows that anti-IL-23R tumor infiltrating Treg have decreased Helios expression. Representative dot plots with graphical analysis gated on IL-23R+ $TCR^+CD4^+FoxP3^+$ for Helios expression (left) and graphical analysis (right) are shown [Mean±SEM Student's T test *p>0.05].
Figure 30:
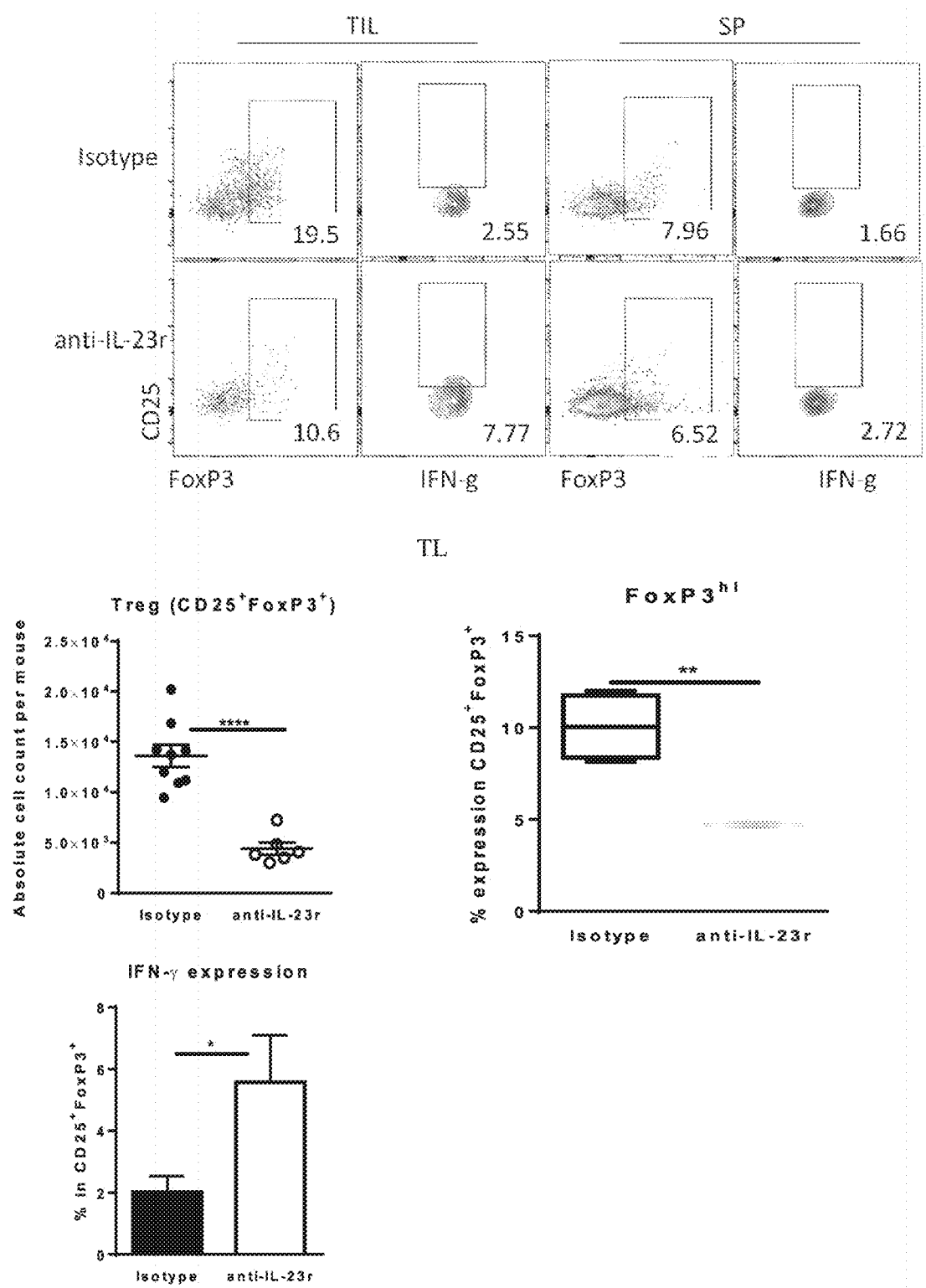
FIG. 30 shows that anti-IL-23R treated mice have significantly reduced intratumoral suppressive Treg compared to isotype. The representative dot plots with graphical analysis gated on $TCR^+CD4^+CD25^+FoxP3$ and IFN-γ expression with graphical analysis on number of tumor infiltrating (TI) Treg, $FoxP3^{hi}$, and IFN-γ expression are shown [Mean±SEM Student's T test *p>0.05 p>0.01 **p>0.0001].
Figure 31:
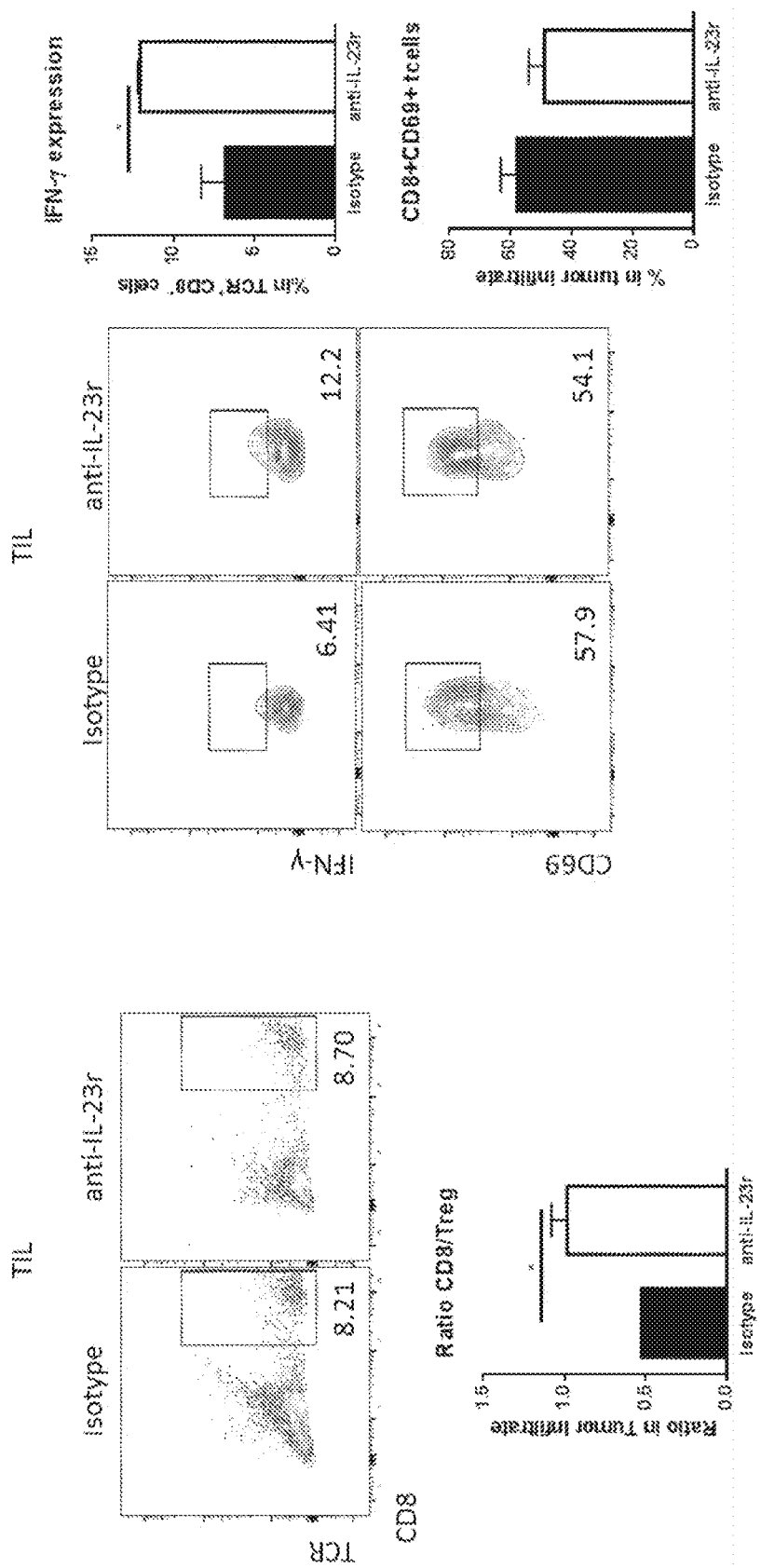
FIG. 31 shows that anti-IL-23R antibody treatment increases intratumoral CD8/Treg ratio and CD8 IFN-γ expression. Representative FACs dot plots gated on single cells lymphocytes (left) and TCR+CD4+CD25+FoxP3+ (right) cells with graphical analysis are shown [Mean±SEM Student's t test *p>0.05].

IL-23R expression was found to be significantly decreased in anti-IL-23R treated tumor and tumor infiltrating activated Treg (FIG. 27). It was also decreased in eTr found in the tumor (FIG. 28). These anti-Il-23R tumor infiltrating Treg have decreased Helios expression (FIG. 29), and reduced intratumoral suppressive Treg compared to isotype-control treated mice (FIG. 30). Anti-Il-23R antibody treatment of cancer cells inoculated mice also increases CD8/Treg ratio and CD8 IFN-γ expression (FIG. 31).

SUMMARY

The data discussed in this example show that anti-IL-23R antibody that recognizes the extracellular domain of the IL-23R chain rather than the IL-12Rβ common chain that also binds to IL-12p40, converts Tregs to effector type cells in the tumor microenvironment specifically.

Example 2: Identifying and Validating Antibodies that Induce T Regulatory (Treg) Conversion and Anti-Tumor Activity An In Vitro Assay to Measure Treg Conversion Two major signaling pathways maintain Treg stability within the tumor microenvironment (TME): 1) a Helios-dependent pathway that enhances IL-2R responsiveness and STAT5 activation and/or 2) an IL-23R signaling pathway that activates STAT5 within intratumoral Treg (FIG. 6). Blockade of either one of these signaling pathways induces Treg conversion as described below. Based on this knowledge, an in vitro screen was developed to identify target surface molecules expressed by Treg that induce Treg→Teff conversion after engagement by an antibody. Verification of the efficacy of antibodies that induce Treg reprogramming as judged by conversion of intratumoral Treg and enhanced anti-tumor immunity is performed in vivo thereafter.

Figure 32:
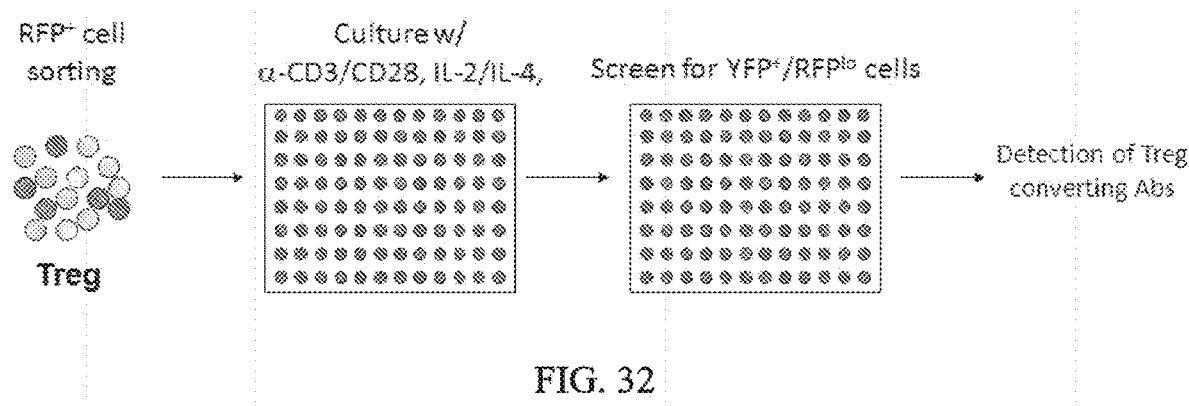
FIG. 32 provides a schema for a Treg conversion screening protocol using a FoxP3$^{RFP}$ IFN-$\gamma^{YFP}$ reporter system.

The in vitro screening system allows identification of Treg surface molecules that, after engagement by antibodies, induce conversion of Treg to T effector cells (FIG. 32). A reporter system that allows detection of a converted Treg phenotype by levels of fluorescence intensity is used: red fluorescence protein (RFP) for FoxP3 and yellow fluorescence protein (YFP) for IFNγ is utilized. Isolated CD4 Treg (RFP$^+$YFP$^+$) are stimulated with anti-CD3/CD28 antibody in the presence of IL-2 and IL-4 to mimic an inflammatory environment. The effect of surface molecule engagement by antibodies is tested in 96 well plates that contain triplicates of test- and control antibody treated wells. Candidate surface molecules and Treg converting antibodies are identified based on reduced RFP and increased YFP signals, which indicate conversion of Treg to T effector cells. Candidate antibodies that display Treg reprogramming activity are validated individually in vitro before testing them in vivo.

Use of Epitope Mapping to Identify Anti-IL-25R Treg Converting Antibodies

The anti-IL-23R antibody that is discussed in Example 1 is a rat anti-mouse antibody. Epitope mapping can be used to develop more antibodies, including anti-human antibodies, that block IL-23R.

Binding sites of the rat anti-mouse IL-23R antibody on IL-23R are mapped using standard epitope mapping techniques. Identification and characterization of the binding sites of anti-IL23R antibody, which has the ability to block IL-23R and induce Treg conversion (see Example 1) is then used to design and develop new antibodies against IL-23R. This data is also used to develop anti-human IL-23R antibodies. The sequence of human IL-23R (SEQ ID NO. 1) is 67% identical to the sequence of mouse IL-23R (SEQ ID NO. 2). Since antibody binding sites are expected to be on the extracellular domain of IL-23R, sequence identity in only that region between species is used for further fine-tuning. The sequence of extracellular domain of human IL-23R (SEQ ID NO. 1, underlined) is 70.5% identical to the sequence of the extracellular domain of mouse IL-23R (SEQ ID NO. 2, underlined).

Amino acid sequence of human IL-23R (extracellular domain is underlined):

(SEQ ID NO. 1)
MNQVTIQWDAVIALYILFSWCHG<u>GITNINCSGHIWVEPATIFKMGMNISIY

CQAAIKNCQPRKLHFYKNGIKERFQITRINKTTARLWYKNFLEPHASMYCT

AECPKHFQETLICGKDISSGYPPDIPDEVTCVIYEYSGNMTCTWNAGKLTY

IDTKYVVHVKSLETEEEQQYLTSSYINISTDSLQGGKKYLVWVQAANALGM

EESKQLQIHLDDIVIPSAAVISRAETINATVPKTIIYWDSQTTIEKVSCEM

RYKATTNQTWNVKEFDTNFTYVQQSEFYLEPNIKYVFQVRCQETGKRYWQP

WSSLFFHKTPETVPQVTSKAFQHDTWNSGLTVASISTGHLTSDNRGDIGLL

LGMIVFAVMLSILSLIGIFNRSFRTGIKRRILLLIPKWLYEDIPNMKNSNV

VKMLQENSELMNNNSSEQVLYVDPMITEIKEIFIPEHKPTDYKKENTGPLE

TRDYPQNSLFDNTTVVYIPDLNTGYKPQISNFLPEGSHLSNNNEITSLTLK

PPVDSLDSGNNPRLQKHPNFAFSVSSVNSLSNTIFLGELSLILNQGECSSP

DIQNSVEEETTMLLENDSPSETIPEQTLLPDEFVSCLGIVNEELPSINTYF

PQNILESHFNRISLLEK</u>

Amino acid sequence of mouse IL-23R (extracellular domain is underlined):

(SEQ ID NO. 2)
MKREREMRGFYYIWDMSHLTLQLHVVIALYVLFRWCHG<u>GITSINCSGDMWV

EPGEIFQMGMNVSIYCQEALKHCRPRNLYFYKNGFKEEFDITRINRTTART

WYKGFSEPHAYMHCTAECPGHFQETLICGKDISSGHPPDAPSNLTCVIYEY

SGNMTCTWNTGKPTYIDTKYIVHVKSLETEEEQQYLASSYVKISTDSLQGS

RKYLVWVQAVNSLGMENSQQLHVHLDDIVIPSASIISRAETTNDTVPKTIV

YWKSKTMIEKVFCfhktpetvpqv</u>

VHQTSQETGKRNWQPWSSPFVHQTSQTVSQVTAKSSHEPQKMEMLSATIFR

GHPASGNHQDIGLLSGMVFLAIMLPIFSLIGIFNRSLRIGIKRKVLLMIPK

WLYEDIPNMENSNVAKLLQEKSVFENDNASEQALYVDPVLTEISEISPLEH

KPTDYKEERLTGLLETRDCPLGMLSTSSSVVYIPDLNTGYKPQVSNVPPGG

NLFINRDERDPTSLETTDDHFARLKTYPNFQFSASSMALLNKTLILDELCL

VLNQGEFNSLDIKNSRQEETSIVLQSDSPSETIPAQTLLSDEFVSCLAIGN

EDLPSINSYFPQNVLESHFSRISLFQK

Example 3: IL-23R Antibodies in Tumor Immunity

Figure 33:
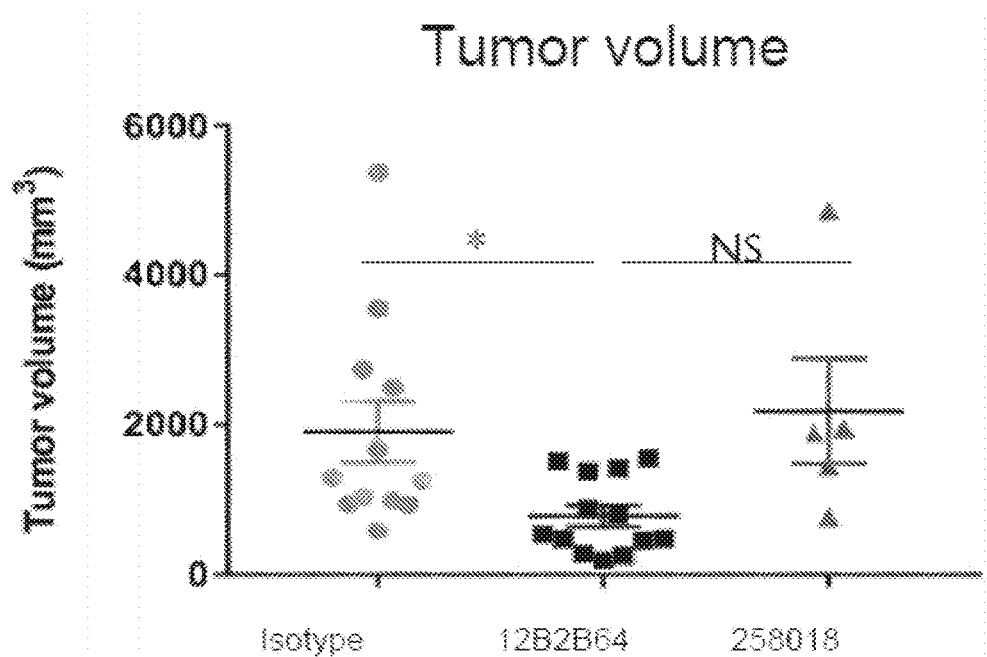
FIG. 33 shows tumor volume in mice inoculated with MC38 cells and treated with isotype or 12B2B64 or 258018 IL-23R antibodies.

Tumor volume was measured in mice treated with IL-23R antibodies. All mice were inoculated with MC38 cells (0.2× $10^6$) and treated with isotype or IL-23R antibodies (100 ug/mouse) given 3 times (i.p 100 uL every third day after tumor formation). Both 12B2B6 (Biolegend clone) and 258018 (R&D clone) antibodies were used. As is shown in FIG. 33, significant delay in tumor growth can be seen in the IL-23R (12B2B64) antibody treated group tumor volume (mm$^3$). Mean±SEM*$p<0.05$.

Figure 34A:
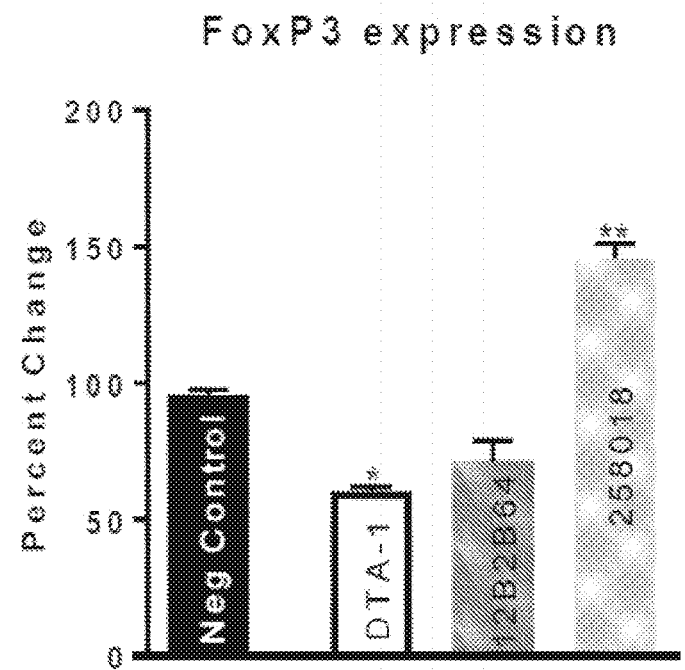
FIGS. 34A-34B show conversion of Tregs upon administration of IL-23R antibodies. Sorted Treg (WT) were plated for 5 days with plate bound anti-CD3/anti-CD28 and in the presence of IL-2 (20 ng/mL) and IL-4 (50 ng/mL) with 10 ng/mL 12B2B64 or 258018 IL-23R antibodies or DTA-1. All samples were compared to Negative Control (no antibody).
Figure 34B:
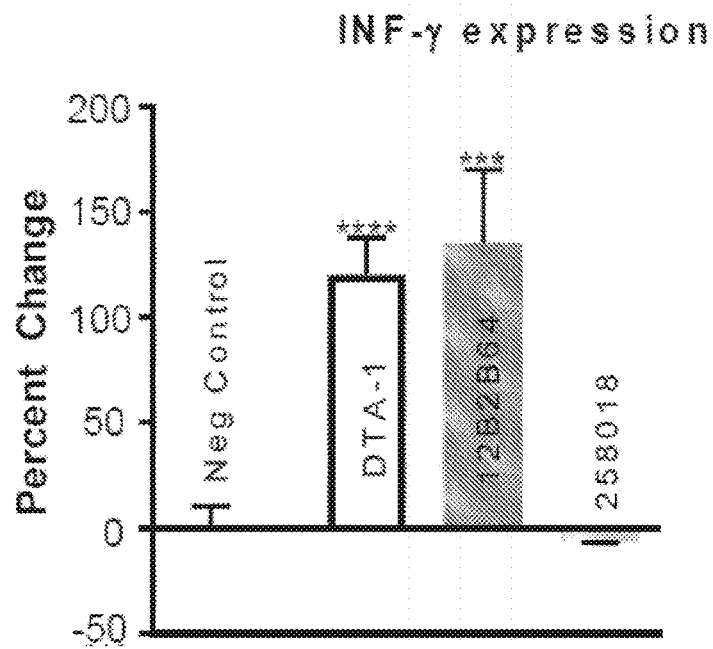

Treg conversion was measured in mice treated with IL-23R antibodies. Sorted Treg (WT) were plated for 5 days with plate bound anti-CD3/anti-CD28 and in the presence of IL-2 (20 ng/mL) and IL-4 (50 ng/mL). 12B2B64 and 258018 antibodies were added at 10 ng/mL on Day 0 of culture. All samples were compared to Negative Control (no antibody). DTA-1 was used as a positive control for Treg conversion. FoxP3 expression is shown in FIG. 34A and IFN-gamma expression is shown in FIG. 34B. Graphs show combined data from three experiments (mean±SEM ANOVA p<0.05 * p<0.01  p<0.001 * p<0.0001 ****). IL-23R antibody (12B2B64-Biolegend) induces Treg conversion in vitro under inflammatory conditions. Additional IL-23 receptor antibody (258018-R&D Systems) did not show evidence of Treg converting (←foxP3 and ↑IFN-g) ability.

Figure 35:
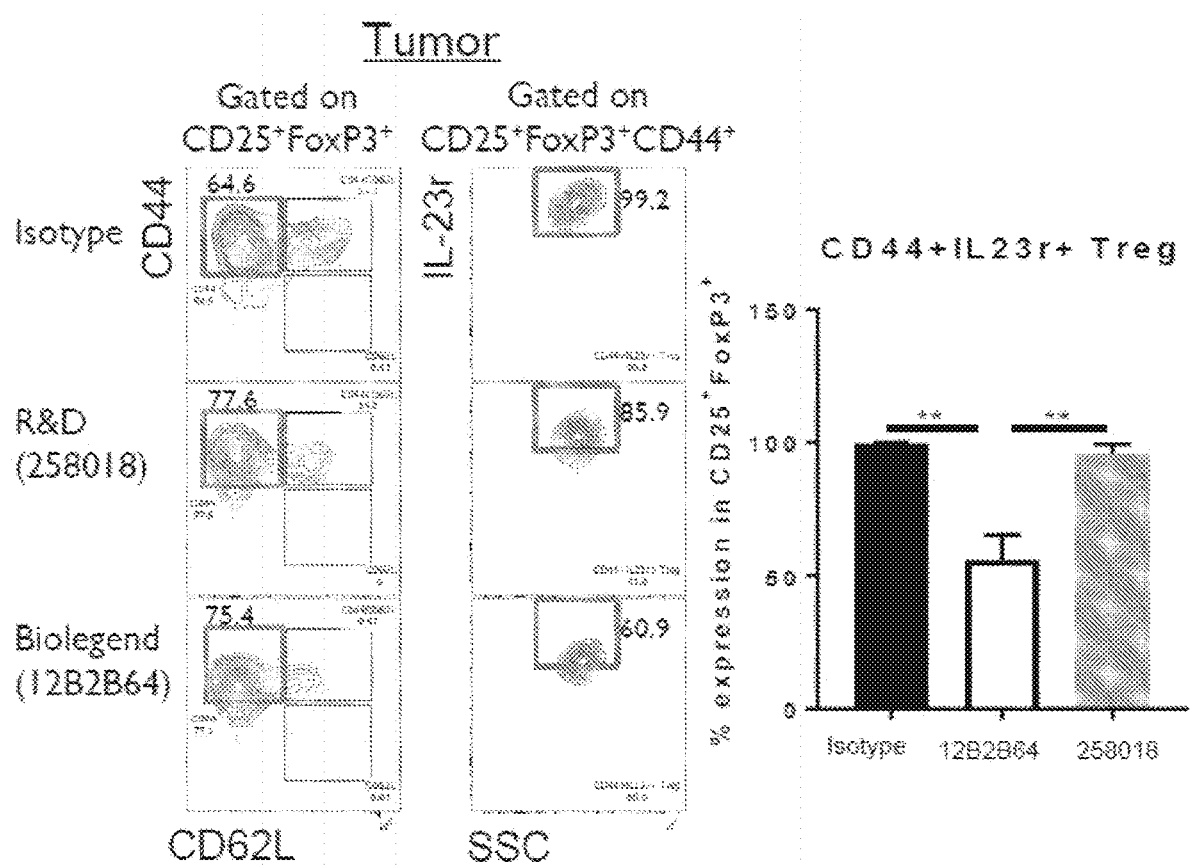
FIG. 35 shows the eTr phenotype in intratumoral Treg in mice treated with IL-23R antibodies. All mice were inoculated with MC38 and treated with isotype or 12B2B64 or 258018 IL-23r Ab. Representative dot plots are gated on Treg (TCR+CD4+CD25+FoxP3+) and eTre (TCR+CD4+CD25+FoxP3+CD44+CD62L−). Graphic analysis is based on IL-23r+ eTr. Mean±SEM ** p<0.01.

The eTr phenotype was also measured in intratumoral Treg in mice treated with IL-23R antibodies. All mice were inoculated with MC38 (0.2×10$^6$) and treated with isotype or 12B2B64 or 258018 IL-23R antibodies (100 ug/mouse) given 3 times (i.p 100 uL every third day after tumor formation). Tumors were collected and digested on day 21 to extract infiltrating immune cells. Cells were then assessed for activation markers without stimulation. Significantly reduced expression of IL-23R$^+$ effector Treg (eTr) (TCR$^+$CD4$^+$CD25$^+$FoxP3$^+$CD44$^+$CD62L$^-$IL-23r$^+$) was observed in the Biolegend (12B2B64) antibody treated group. Representative dot plots shown in FIG. 35 were gated on Treg (TCR$^+$CD4$^+$CD25$^+$FoxP3$^+$) and eTre (TCR$^+$CD4$^+$CD25$^+$FoxP3$^+$CD44$^+$CD62L$^-$). Graphic analysis is based on IL-23R$^+$eTr. Mean±SEM ** p<0.01.

Figure 36:
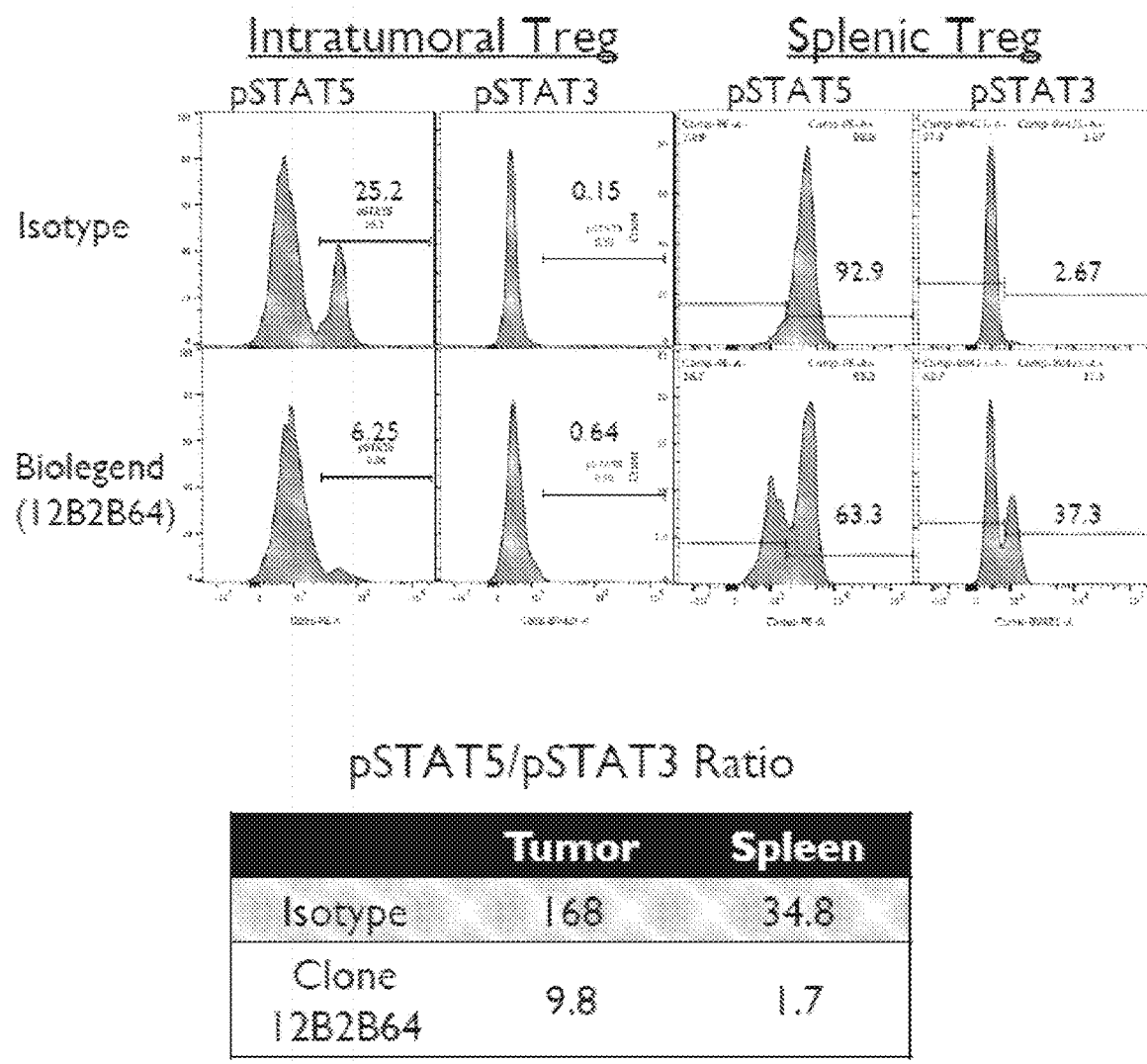
FIG. 36 shows the pSTAT5:pSTAT3 ratio in mice treated with IL-23R antibodies. All mice were inoculated with MC38 and treated with isotype or 12B2B64 or 258018 IL-23r Ab. The STAT5 activation and STAT3 activation was measured in tumor and spleen. Representative histograms are shown as are the pSTAT5:pSTAT3 ratios.

The pSTAT5:pSTAT3 ratio was also assessed in mice treated with IL-23R antibodies. All mice were inoculated with MC38 (0.2×10$^6$) and treated with isotype or 12B2B64 or 258018 IL-23R antibodies (100 ug/mouse) given 3 times (i.p 100 uL every third day after tumor formation). Tumors and spleen were immediately fixed and assessed for STAT activation (pSTAT5 and pSTAT3) without stimulation. Reduced expression of pSTAT5 was observed in the IL-23R (12B2B64) antibody treated group resulting in a reduced overall pSTAT5/pSTAT3 ratio. Representative histograms are depicted in FIG. 36 and ratios are shown.

Figure 37:
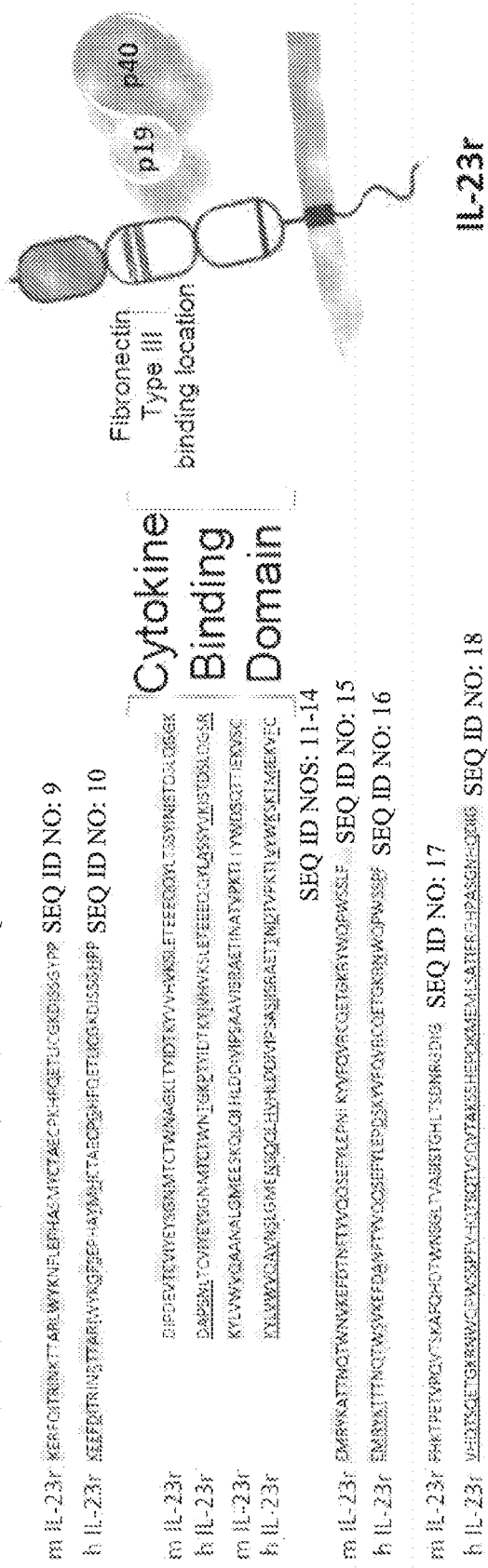
FIG. 37 shows an alignment of murine and human IL-23R and a schematic illustration of the domains of IL-23R.
Figure 38:
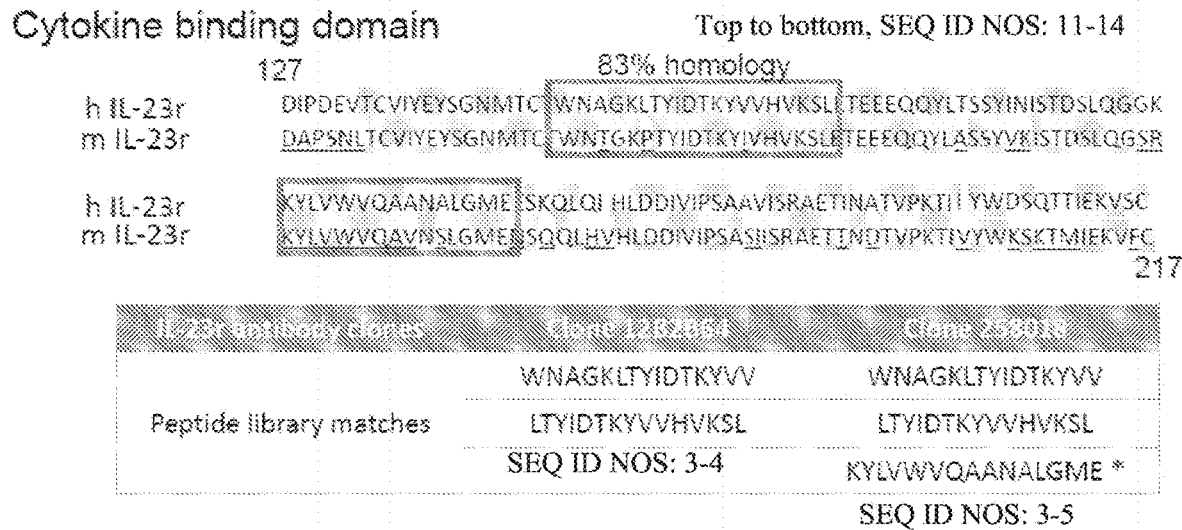
FIG. 38 shows the regions in the cytokine binding domain of IL-23R where the peptides identified in the epitope mapping study are located.

Epitope mapping was done for the 12B2B64 and 258018 IL-23R antibodies. FIG. 37 shows an alignment of murine and human IL-23R and a schematic illustration of the domains of IL-23R. Using the proposed cytokine binding domain, a peptide library constructed of 26 peptides. The peptides were 15 amino acids long with an additional 5 amino acids of overhang. Binding of the antibodies to the peptides was assessed via ELISA. The peptides were bound to a plate, the antibodies were incubated with the individual peptides at various concentrations, and the analysis was completed in a plate reader. Of the 26 peptides in the library 23 were not bound by either antibody. Antibody 12B2B64 bound WNAGKLTYIDTKYVV (SEQ ID NO. 3) and LTYIDTKYVVHVKSL (SEQ ID NO. 4). Antibody 258018 bound WNAGKLTYIDTKYVV (SEQ ID NO. 3), LTYIDTKYVVHVKSL (SEQ ID NO. 4), and KYLVWVQAANALGME (SEQ ID NO. 5). FIG. 38 shows the regions in the cytokine binding domain where the peptides are located.

Example 4: IL-23R Modulates Treg Conversion Via STAT5 and STAT3

Figure 39A:
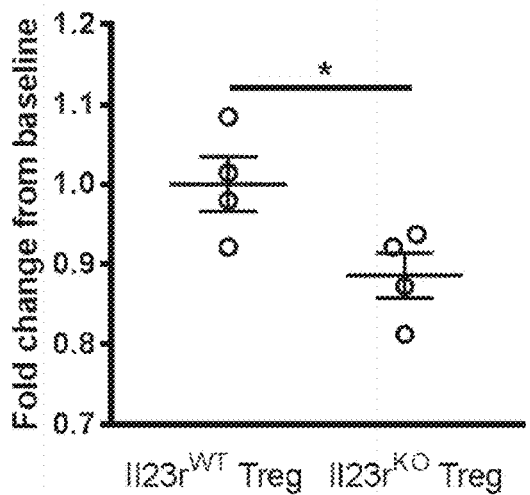
FIGS. 39A-39B show that loss of IL-23R enhances conversion of Treg→Teff generally in a Treg conversion assay.
Figure 39B:
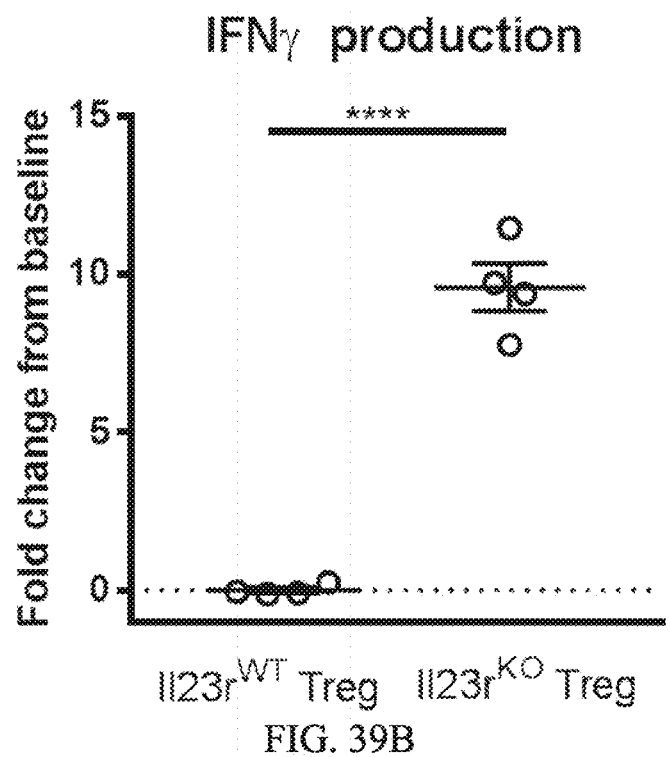
Figure 40A:
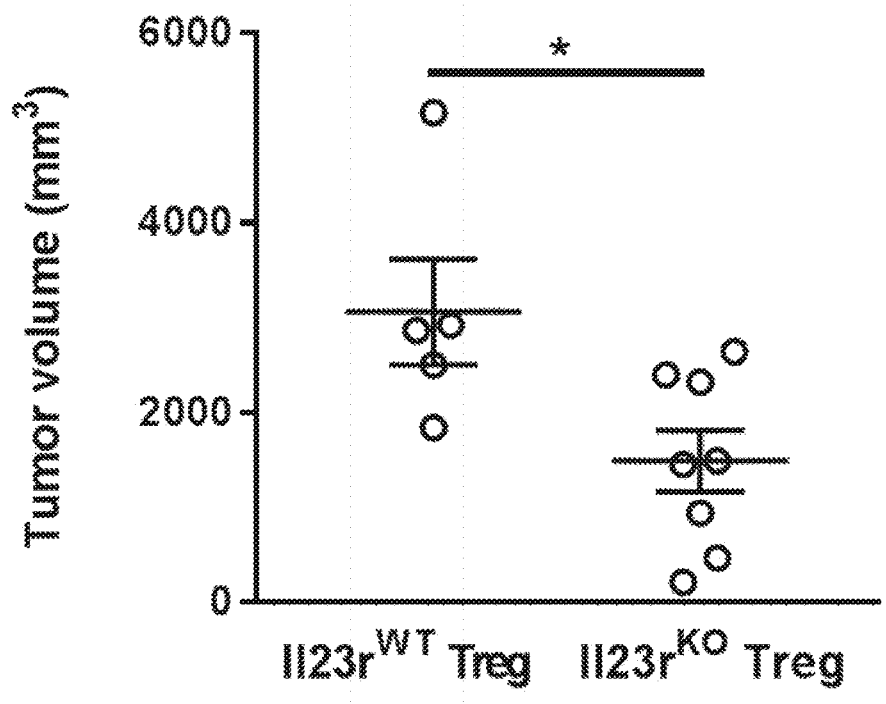
FIGS. 40A-40C shows that loss of IL-23R enhances conversion of Treg→Teff in tumor cells. Genetic deletion of IL-23R in Tregs injected into Rag2$^{-/-}$ mice leads to a decrease in tumor volume in mice inoculated with the MC38 cancer cell line (FIG. 40A), a decrease in FoxP3 expression (FIG. 40B) and an increase in IFN-γ expression (FIG. 40C) compared to IL-23R$^{WT}$ Treg controls. Expression levels from TIL and spleen cells were independently tested.
Figure 40B:
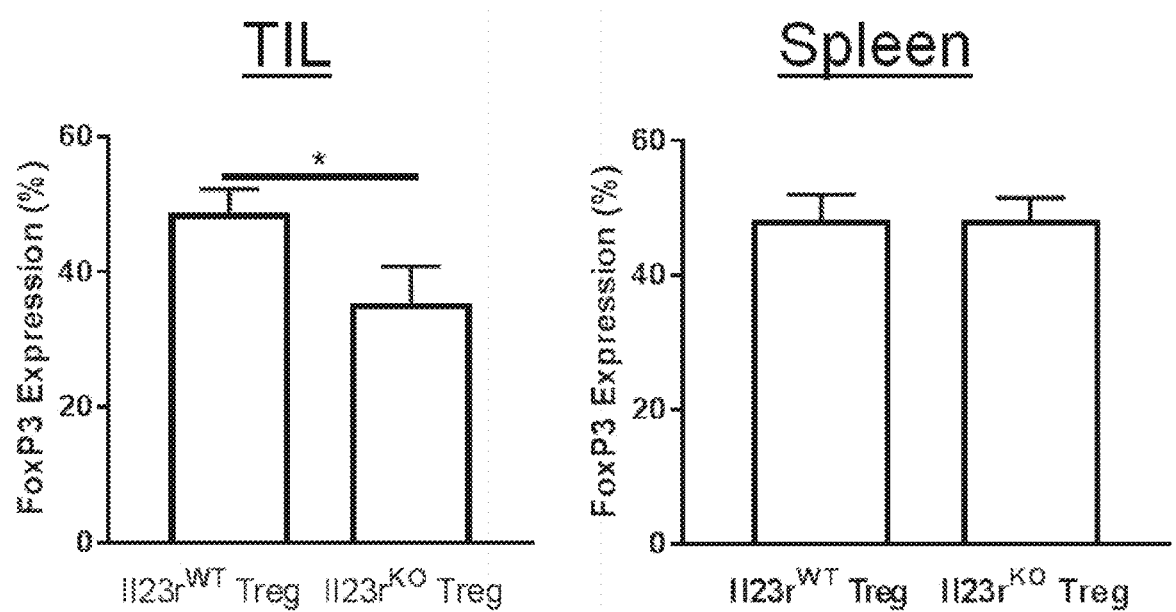
Figure 40C:
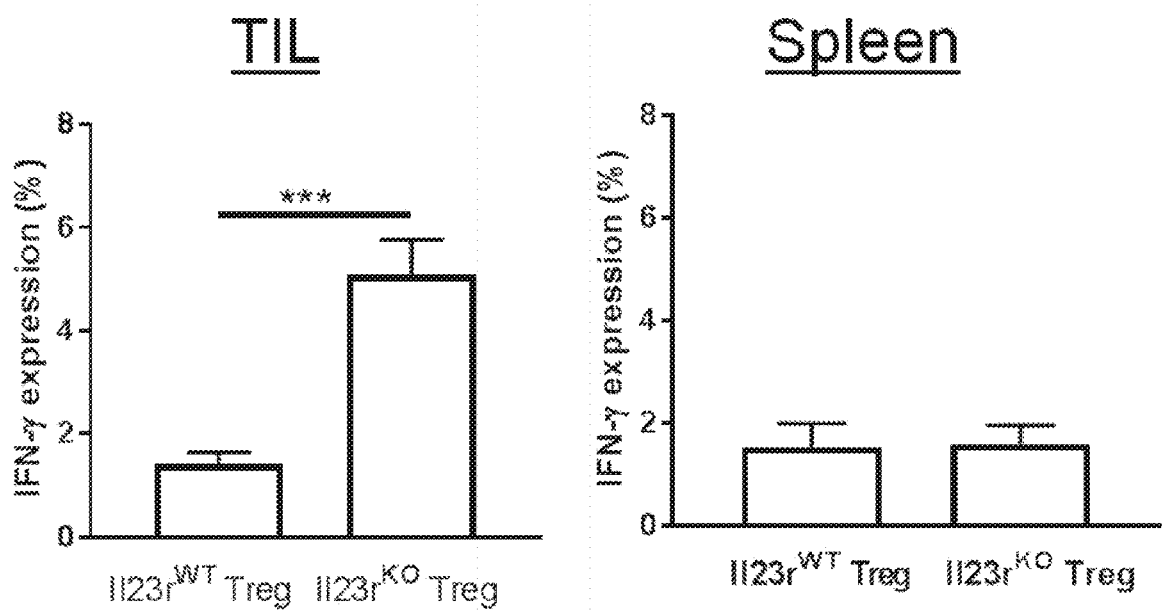

Loss of IL-23R enhances Treg conversion generally and in tumor cells specifically. FIGS. 39A-39B show that loss of IL-23R enhances conversion of Treg→Teff generally in a Treg conversion assay. IL-23R$^{KO}$ Tregs showed decreased FoxP3 and increased IFN-γ expression compared to C57BL/6 controls (FIGS. 39A-39B). FIGS. 40A-40C show that loss of IL-23R enhances conversion of Treg→Teff in tumor cells and decreases tumor volume. Treg isolated from IL-23R$^{KO}$ or C57BL/6 mice were FACS sorted and transferred into Rag2$^{-/-}$ mice via injection into the tail vein along with CD8$^+$ T cells. The mice were then inoculated with MC38 cancer cell line and tumor volume, and FoxP3 and IFN-γ expression in Treg from TIL and the spleen were measured. The results presented herein show that loss of IL-23R decreases tumor volume, decreased FoxP3 expression and increased IFN-γ expression compared to C57BL/6 controls. FIGS. 40A-40C show knockout of IL-23R enhances conversion of Treg→Teff in tumor cells.

Figure 41A:
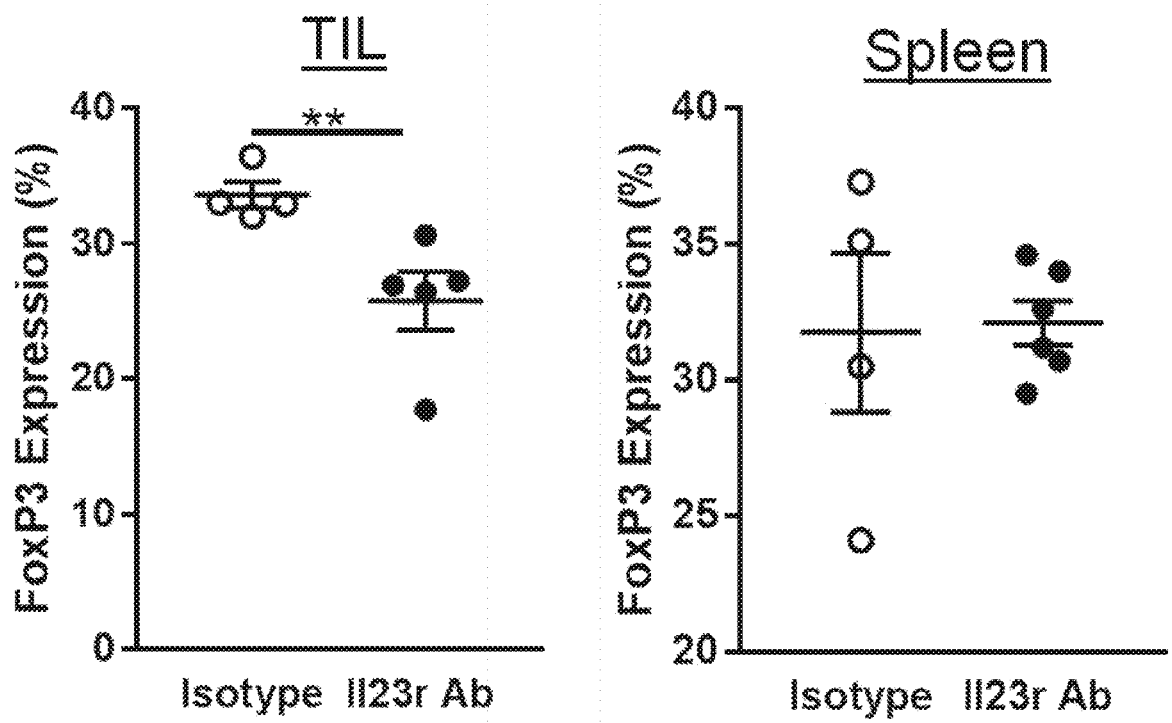
FIGS. 41A-41B show that anti-IL-23R antibody induces conversion of Treg→Teff in EL4 lymphoma tumor cells. Treatment of mice inoculated with EL4 cancer cells with anti-IL-23R antibody leads to a decrease in FoxP3 expression (FIG. 41A) and an increase in IFN-γ expression (FIG. 41B) compared to treatment with isotype. Expression levels from TIL and spleen cells were independently tested.
Figure 41B:
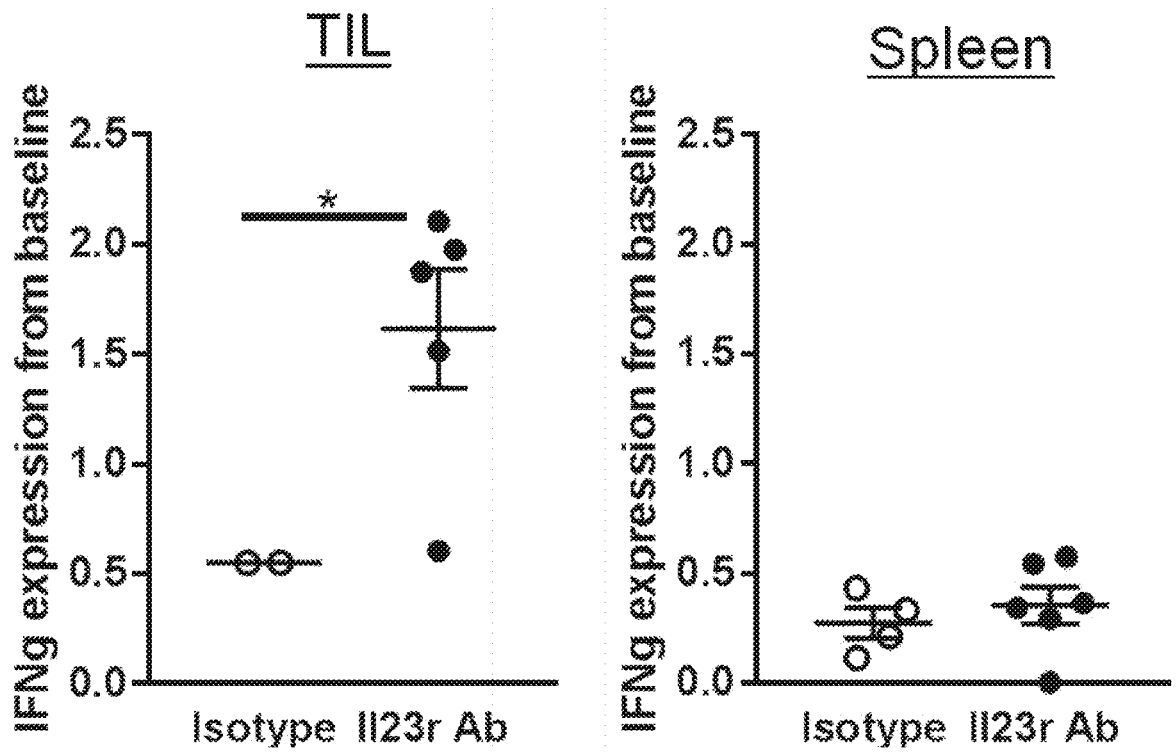

Treatment of mice having tumors from inoculation with the EL4 cancer cell line with anti-IL-23R antibody shows that treatment with anti-IL-23R antibody also enhances conversion of Treg→Teff in lymphoma tumor cells. Briefly, mice were inoculated with EL4 cancer cells (0.4×10$^6$) for 21 days before being treated with isotype or anti-IL-23R antibody (100 µg/mouse) three times (i.p 100 µL every third day after tumor formation). As shown in FIGS. 41A-41B, treatment of mice with EL4 tumors with anti-IL-23R antibody decreased FoxP3 expression and increased IFN-γ expression compared to controls. These results further demonstrate that treatment with anti-IL-23R antibody enhances conversion of Treg→Teff in tumor cells.

Figure 42A:
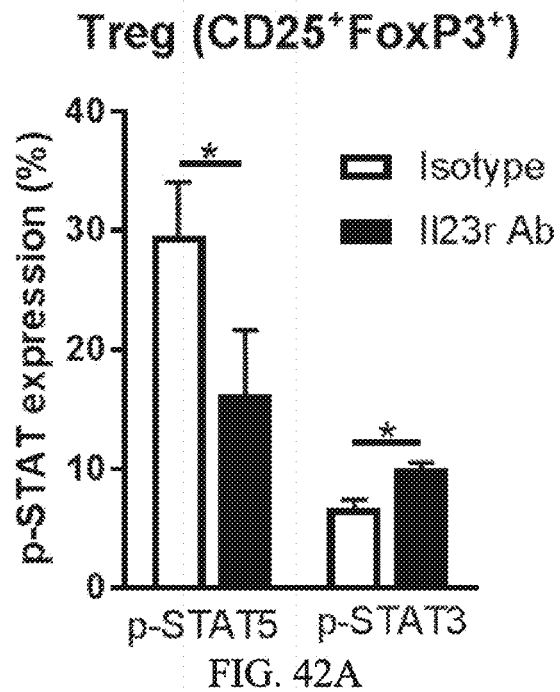
FIGS. 42A-42C shows that show that treatment with anti-IL-23R antibody in vitro alters STAT5 and STAT3 expression. Treatment of CD25+FoxP3+ Tregs with anti-IL-23R antibody leads to a decrease in pSTAT5 expression and an increase in pSTAT3 expression compared to treatment with isotype (FIG. 42A). These expression changes result in a decrease in the pSTAT5:pSTAT3 ratio for Tregs treated with anti-IL-23R antibody compared to isotype (FIG. 42B). Treatment with anti-IL-23R antibody also leads to increased expression of IFN-γ (FIG. 42C)
Figure 42B:
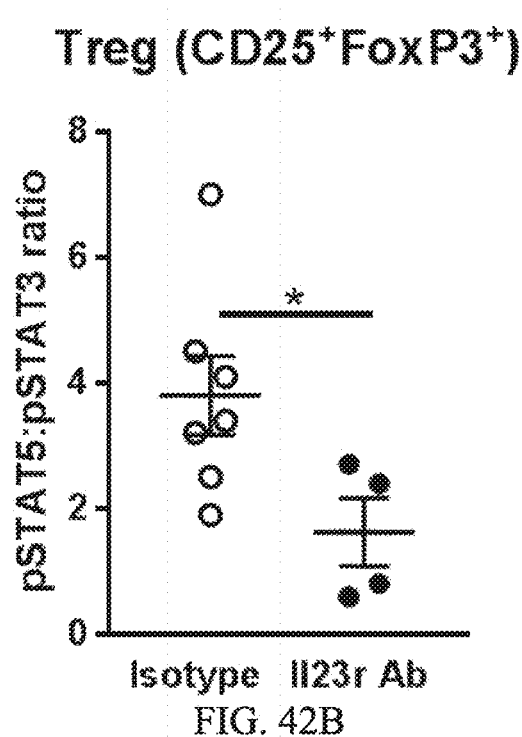
Figure 42C:
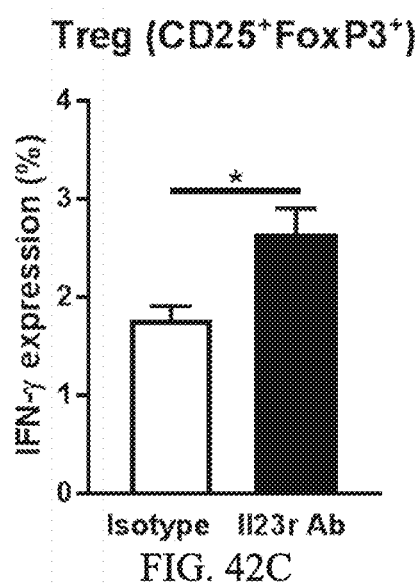
Figure 43A:
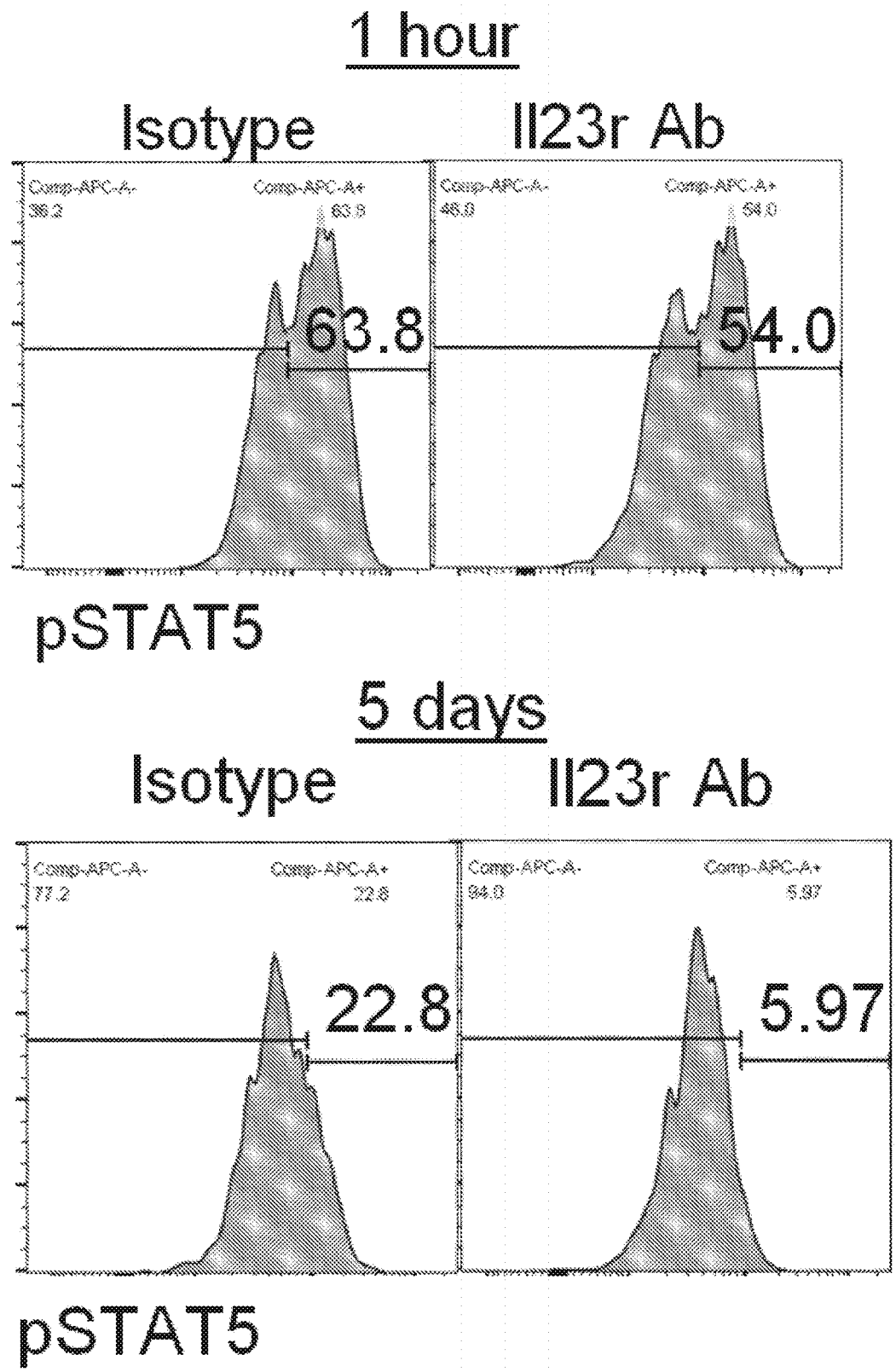
FIGS. 43A-43B shows that treatment with anti-IL-23R antibody reduces STAT5 expression in Treg at multiple timepoints. The reduction in pSTAT5 expression resulting in treatment of CD25+FoxP3+ Tregs with anti-IL-23R antibody compared to isotype occurs at one hour and persists at five days as shown by flow cytometry (FIG. 43A) and as a percentage of initial expression (FIG. 43B).
Figure 43B:
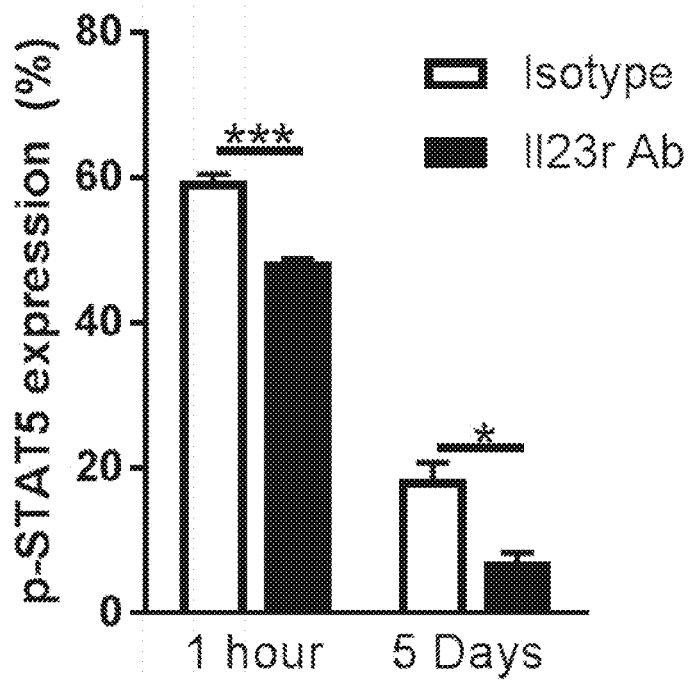

To demonstrate that knockdown of IL-23R, via neutralizing antibody, impacts STAT5 and STAT3 expression levels, CD25$^+$FoxP3$^+$ Tregs were treated with either isotype or anti-IL-23R antibody in vitro. As shown in FIGS. 42A-C, CD25$^+$FoxP3$^+$ Tregs treated with anti-IL-23R antibody had significant reduction in the pSTAT5:pSTAT3 ratio compared to isotype-treated. This resulted from a decrease in pSTAT5 expression and an increase in pSTAT3 expression in anti-IL-23R antibody-treated cells compared to isotype-treated cells as determined by flow cytometry (FIGS. 42A-42B). Furthermore, as shown in FIGS. 43A-43B, this significant reduction in pSTAT5 expression occurs shortly after treatment (54% pSTAT5 expression in anti-IL-23R antibody-treated compared to 63.8% pSTAT5 expression in isotype-treated at one hour) and persists on longer timescales (5.97% pSTAT5 expression in anti-IL-23R antibody-treated compared to 22.8% pSTAT5 expression in isotype-treated at five days).

Figure 44A:
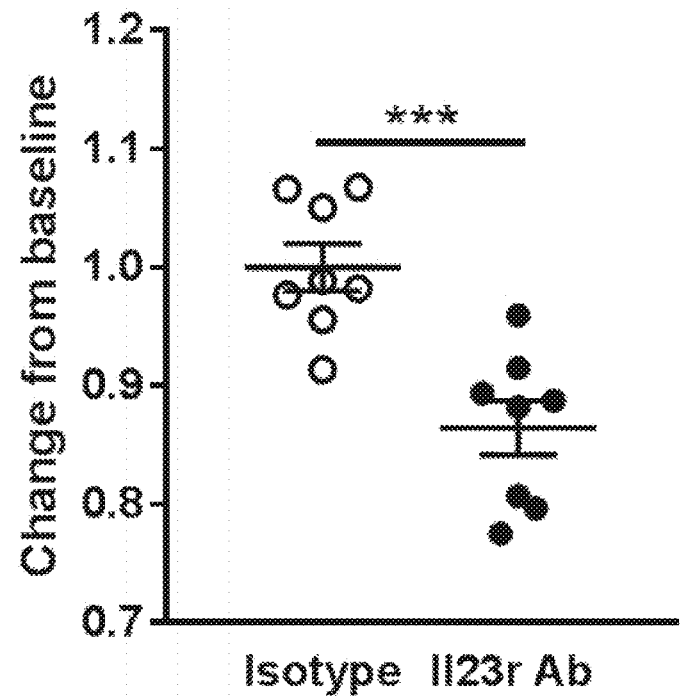
FIGS. 44A-44F shows the effect of an anti-IL-23R antibody treatment in mice that have been inoculated with MC38 cancer cells.
Figure 44B:
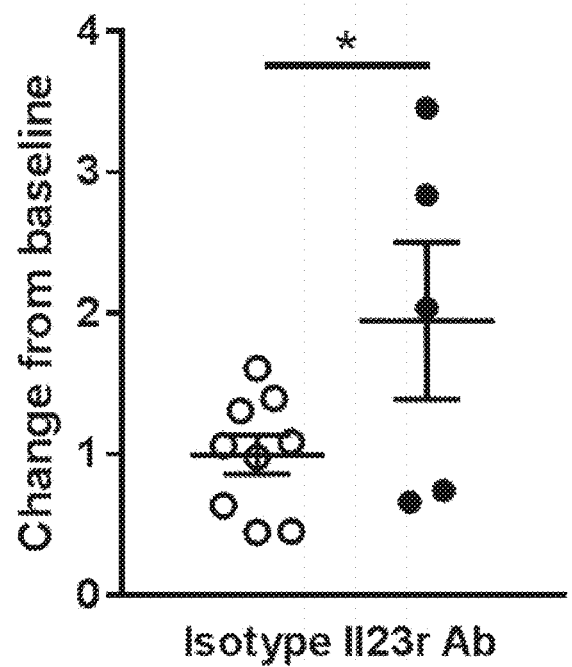
Figure 44C:
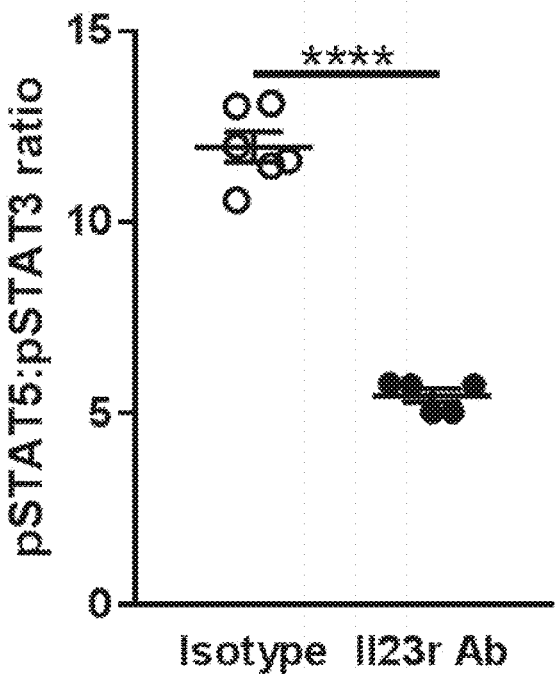
Figure 44D:
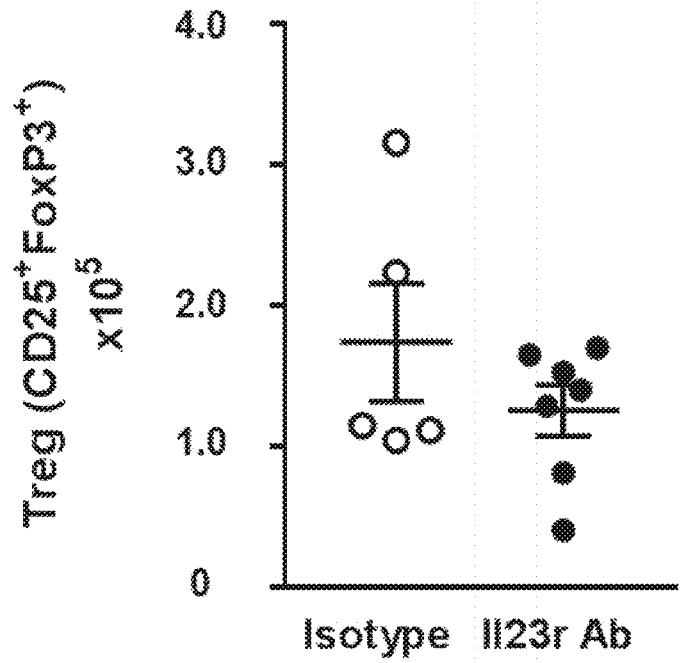
Figure 44E:
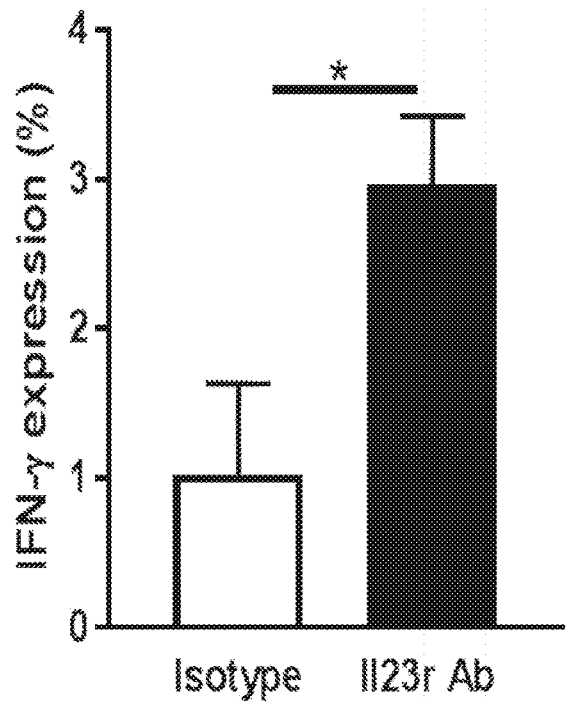
Figure 44F:
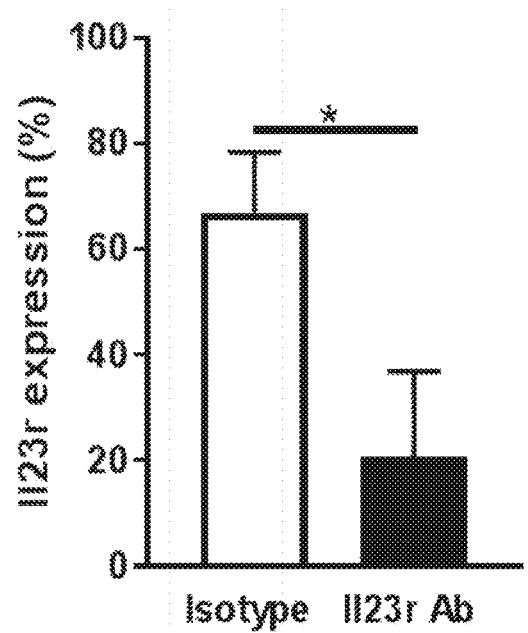
Figure 45A:
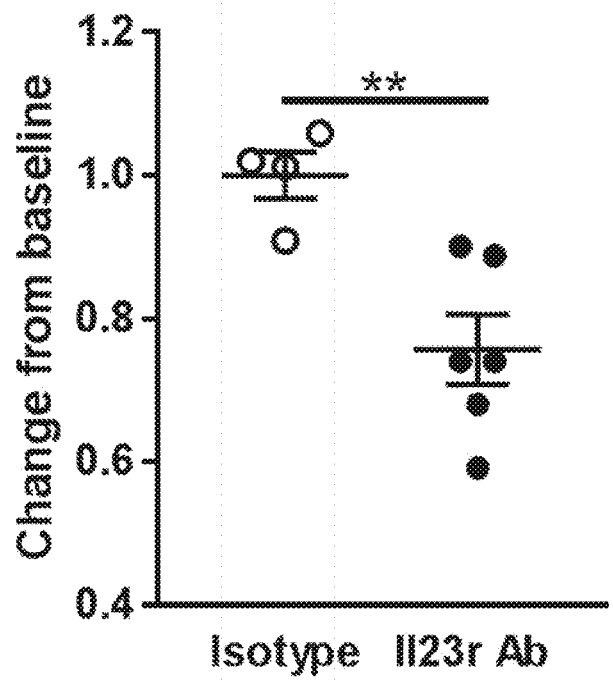
FIGS. 45A-45B show the effect of an anti-IL-23R antibody treatment in mice that have been inoculated with EL4 cancer cells on STAT5 and STAT3 expression. Expression of STAT5 in mice inoculated with EL4 cancer cells and treated with anti-IL-23R antibody is shown in FIG. 45A. The pSTAT5:pSTAT3 ratio, compared to treatment with isotype, is shown in FIG. 45B.
Figure 45B:
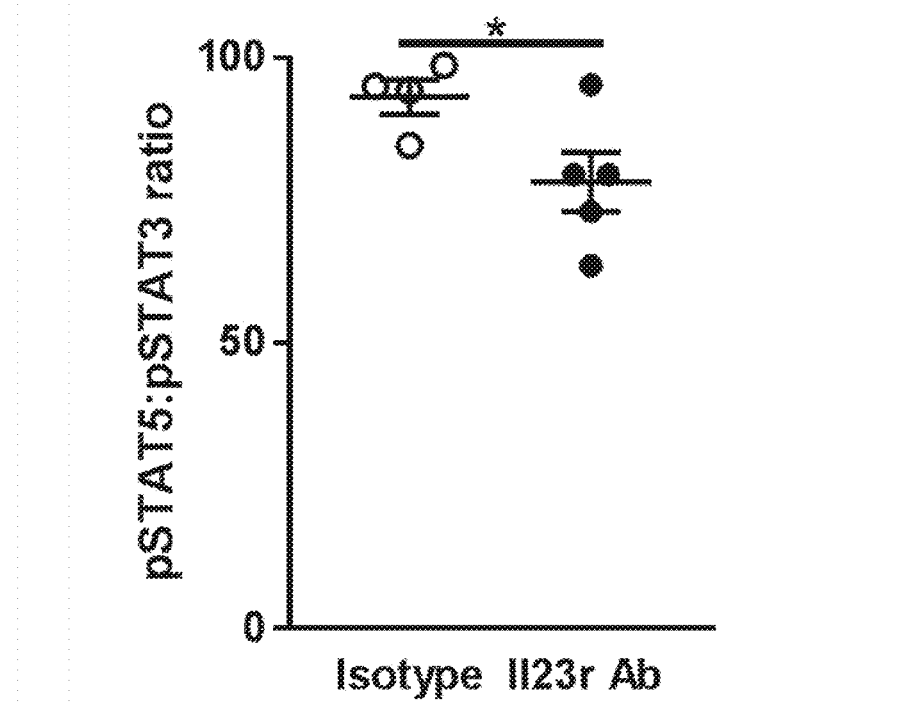

To corroborate the effectiveness of anti-IL-23R antibodies to enhance conversion of Treg→Teff in tumor cells via STAT5 and STAT3 expression, a in vivo model was tested with anti-IL-23R antibody. Similar to previous experiments, mice were inoculated with MC38 cancer cells (0.2×10$^6$), treated with isotype or anti-IL-23R antibody (100 µg/mouse) three times (i.p 100 µL every third day after tumor formation), and FACS analysis was performed on Day 25 after inoculation. FIGS. 44A-44C show that treatment of mice with MC38 tumors with anti-IL-23R antibody provided a significant reduction in the pSTAT5:pSTAT3 ratio compared to mice treated with isotype, as anti-IL-23R antibody-treated mice had a reduction in pSTAT5 expression and an increase in pSTAT3 expression compared to isotype-treated mice. Mice treated with anti-IL-23R antibody also had increased IFN-γ expression and decreased IL-23R expression levels compared to isotype-treated mice, as shown in FIGS. 44E-44F. FIG. 44D demonstrates that anti-IL-23R antibody treatment decreases the numbers of CD25$^+$FoxP3$^+$ Tregs, compared to isotype treatment. In a similar experiment, mice were inoculated with EL4 cancer cells (0.4×10$^6$), treated with isotype or anti-IL-23R antibody (100 µg/mouse) three times (i.p 100 µL every third day after tumor formation), and FACs analysis was completed 21 days after inoculation. As shown in FIGS. 45A-45B, treatment of mice with anti-IL-23R antibody decreased pSTAT5 expression and provided a reduction in the pSTAT5:pSTAT3 ratio, compared to isotype-treated mice.

Figure 46A:
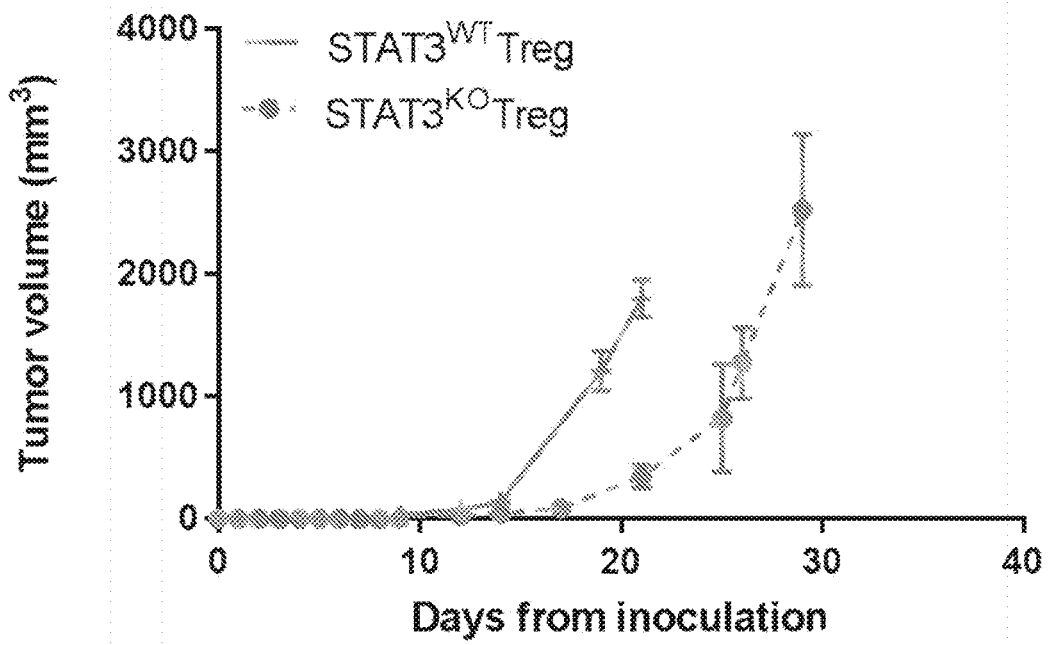
FIGS. 46A-46C show the effect of STAT3 expression by Treg on tumor growth CD69 and IFN-γ expression.
Figure 46B:
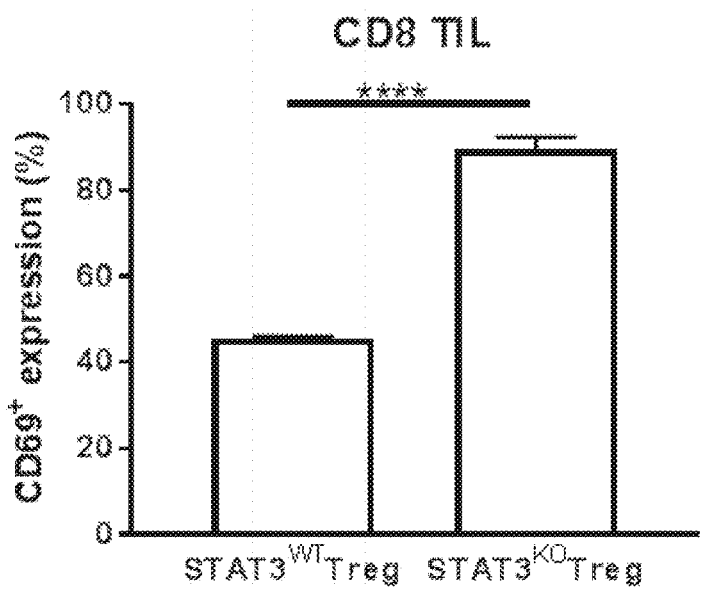
Figure 46C:
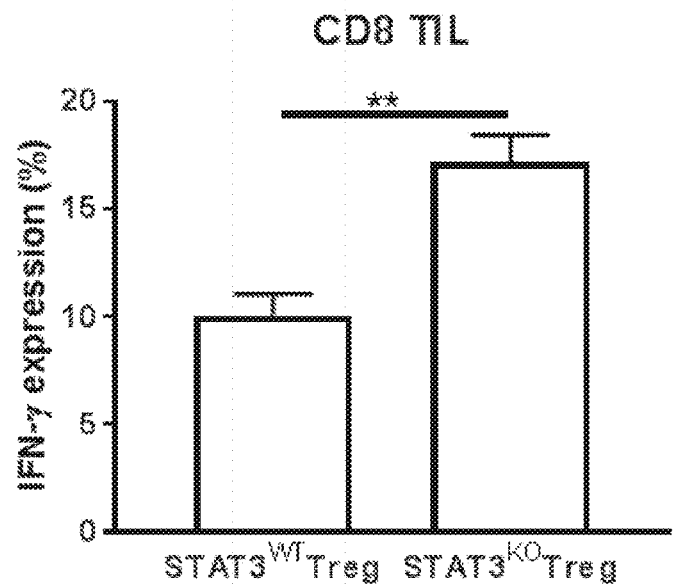

The role of STAT3 in tumor growth was further investigated. STAT3$^{WT}$Treg mice and STAT3$^{KO}$Treg mice were inoculated with MC38 cancer cells ($0.2 \times 10^6$). STAT3$^{KO}$Treg mice have been genetically engineered for knockout of STAT3 in Tregs (STAT3$^{fl/fl}$FoxP3$^{cre}$). FIG. 46A shows that tumor growth, as assessed by tumor volume, progresses more slowly in STAT3$^{KO}$Treg mice then it does in STAT3$^{WT}$Treg mice. Additionally, STAT3$^{KO}$Treg mice have increased expression levels of CD69 and IFN-γ compared to STAT3$^{WT}$Treg mice in CD8 TIL (FIGS. 46B-46C).

Figure 47A:
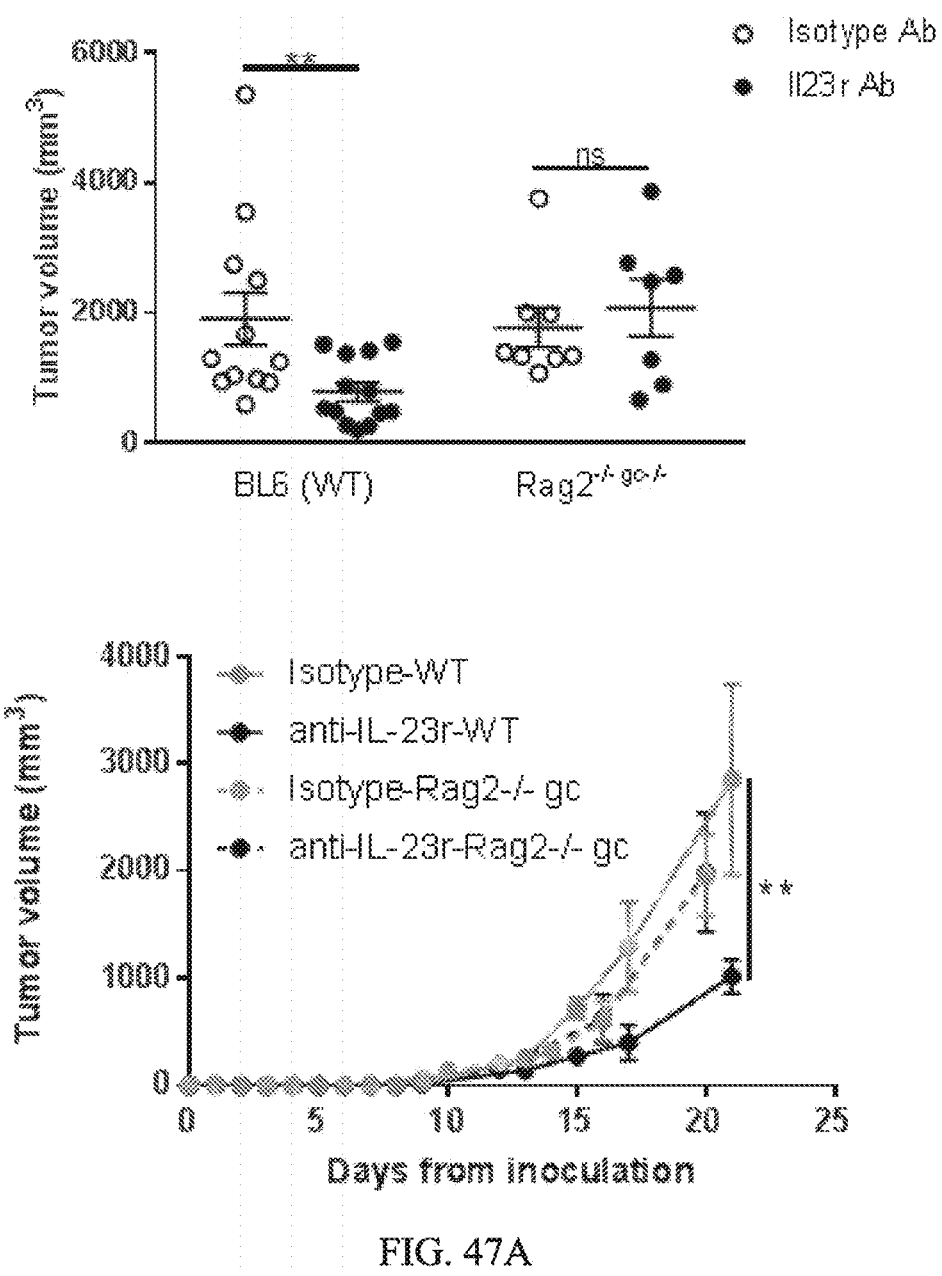
FIGS. 47A-47B show that anti-IL23-R antibody interacts with Tregs.

It was next investigated whether the anti-IL23R antibody directly interacts with IL23-R Treg. This was first investigated by looking at tumor volume in C57BL/6 and Rag2$^{-/-}$ mice inoculated with MC38 cancer cells ($0.2 \times 10^6$) for nine days before being treated with isotype or anti-IL-23R antibody (100 μg/mouse) three times (i.p 100 μL every third day after tumor formation). FIG. 47A shows that C57BL/6 mice treated with anti-IL-23R antibody had a reduction in tumor volume at the end of the treatment period compared to C57BL/6 mice treated with isotype. There was no difference observed for Rag2$^{-/-}$ mice.

Figure 47B:
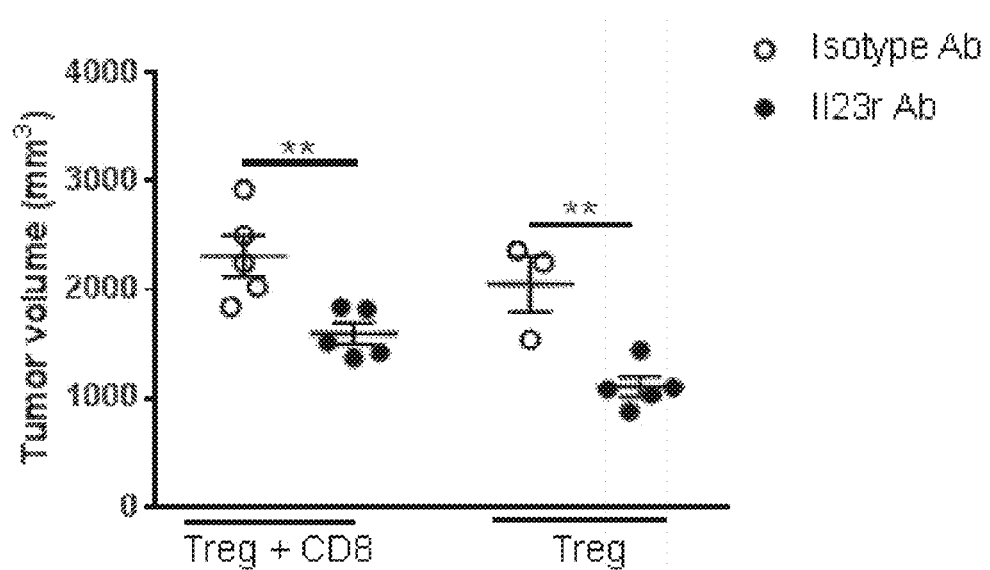
Figure 47B:
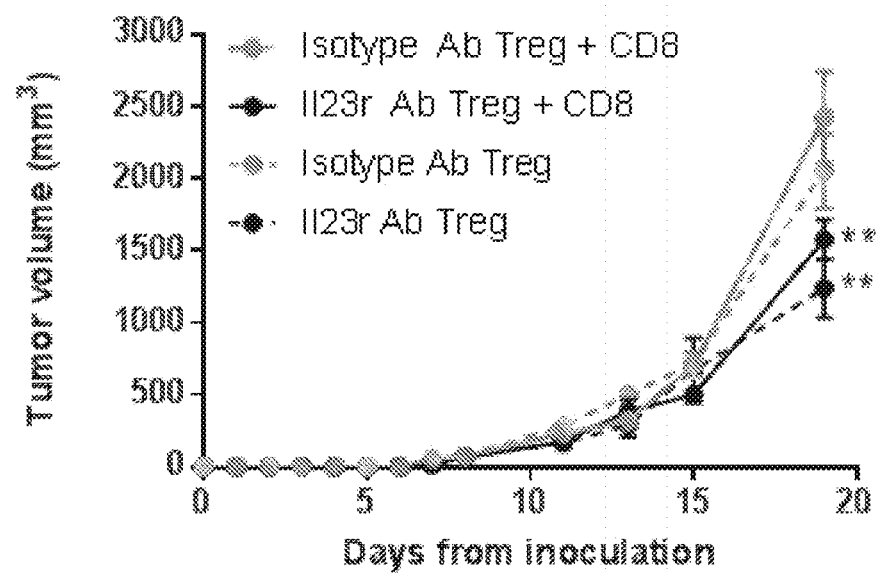

Whether the anti-IL23R antibody directly interacts with IL23-R Treg was next investigated by looking at tumor volume in mice in which isolated Tregs alone or in conjunction with CD8$^+$ T cells were injected into the tail veins of Rag2$^{-/-}$ mice. The mice were then inoculated with MC38 cancer cells ($0.2 \times 10^6$) for nine days before being treated with isotype or anti-IL-23R antibody (100 μg/mouse) three times (i.p 100 μL every third day after tumor formation). FIG. 47B demonstrates that anti-IL-23R antibody decreases tumor volume, compared to isotype, in Rag2$^{-/-}$ mice that have been injected with Tregs alone or in conjunction with CD8$^+$ T cells.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating cancer in a human subject, the method comprising:
    administering to a human subject in need thereof an agent that decreases IL-23R activity and does not decrease IL-12Rβ activity, in an amount effective to treat the cancer;
    wherein the agent is a human or humanized antibody derived from mouse monoclonal antibody 12B2B64;
    wherein the antibody binds IL-23R and does not bind IL-12Rβ; and
    wherein the antibody binds to an epitope of IL-23R on regulatory T (Treg) cells, comprising the amino acid sequence of SEQ ID NO: 3 or SEQ ID NO: 4.

2. The method of claim 1, wherein the agent decreases IL-23R activity and does not decrease IL-12Rβ activity in the Treg cells.

3. The method of claim 1, wherein the antibody has 100-fold, 1,000-fold, or 10,000-fold greater binding affinity for IL-23R than for IL-12Rβ.

4. The method of claim 1, wherein the antibody binds the extracellular domain of IL-23R.

5. The method of claim 1, wherein binding of the antibody to the epitope of IL-23R converts the Treg cells to effector T (Teff) cells.

6. The method of claim 1, wherein the antibody is free of antibody dependent cellular cytotoxicity (ADCC) activity.

7. The method of claim 1, wherein the human or humanized antibody has an IgG4 heavy chain immunoglobulin constant domain.

8. The method of claim 1, wherein the antibody is administered to the subject in an amount of about 0.1 to 300 mg/kg of the body weight of the subject divided into one or more doses.

9. The method of claim 1, further comprising administering to the human subject an immunomodulatory agent.

10. The method of claim 9, wherein the immunomodulatory agent is an immune checkpoint inhibitor.

11. The method of claim 10, wherein the immune checkpoint inhibitor is an antagonist of a molecule selected from the group consisting of PD-1, TIM-3, TIGIT, VISTA, A2AR, B7-H3, B7-H4, BTLA, CTLA-4, IDO, KIR and LAG3.

12. The method of claim 1, further comprising administering to the human subject an agent that inhibits cancer cell growth.

13. The method of claim 1, further comprising measuring activation of STAT3, STAT5, and/or IFN-□ in the human subject following administration of the agent.

14. The method of claim 13, wherein STAT3 expression is increased, STAT5 expression is decreased, and/or IFN-γ expression is increased, relative to a control subject.

15. The method of claim 1, wherein the cancer is a melanoma or colorectal cancer.

* * * * *